United States Patent
Costella

(10) Patent No.: US 11,559,723 B2
(45) Date of Patent: Jan. 24, 2023

(54) COMBINED OSCILLATING POSITIVE EXPIRATORY PRESSURE THERAPY AND HUFF COUGH SIMULATION DEVICE

(71) Applicant: Trudell Medical International, London (CA)

(72) Inventor: Stephen Costella, London (CA)

(73) Assignee: Trudell Medical International, London (CA)

(*) Notice: Subject to any disclaimer, the term of this patent is extended or adjusted under 35 U.S.C. 154(b) by 562 days.

(21) Appl. No.: 16/604,499

(22) PCT Filed: Apr. 26, 2018

(86) PCT No.: PCT/IB2018/052899
§ 371 (c)(1),
(2) Date: Oct. 10, 2019

(87) PCT Pub. No.: WO2018/203188
PCT Pub. Date: Nov. 8, 2018

(65) Prior Publication Data
US 2020/0054921 A1     Feb. 20, 2020

Related U.S. Application Data

(60) Provisional application No. 62/500,707, filed on May 3, 2017.

(51) Int. Cl.
A63B 23/18      (2006.01)
A61M 16/00      (2006.01)
A61M 16/20      (2006.01)

(52) U.S. Cl.
CPC .......... *A63B 23/18* (2013.01); *A61M 16/0006* (2014.02); *A61M 16/205* (2014.02); *A61M 16/208* (2013.01)

(58) Field of Classification Search
CPC .............. A63B 23/18; A63B 21/00196; A63B 2071/0694; A63B 23/185; A61B 5/0875;
(Continued)

(56) References Cited

U.S. PATENT DOCUMENTS

| 393,869 A | 12/1888 | Warren |
| 938,808 A | 11/1909 | Yount |

(Continued)

FOREIGN PATENT DOCUMENTS

| CA | 3005796 A1 | 6/2017 |
| EP | 0 372 148 A1 | 6/1990 |

(Continued)

OTHER PUBLICATIONS

U.S. Appl. No. 14/674,494, filed Mar. 31, 2015, Meyer et al.
(Continued)

*Primary Examiner* — Elliot S Ruddie
(74) *Attorney, Agent, or Firm* — Crowell & Moring LLP

(57) ABSTRACT

A respiratory treatment device including an OPEP (oscillating positive expiratory pressure) mechanism, a Huff Cough mechanism, a user interface, and a conduit leading from the user interface to the OPEP mechanism and the Huff Cough mechanism, wherein air flow through the conduit is selectively directed to the OPEP mechanism and the Huff Cough mechanism.

25 Claims, 63 Drawing Sheets

(58) Field of Classification Search
CPC .... A61B 5/0876; A61B 5/09; A61M 16/0006; A61M 16/20–205; A61M 16/208; A61M 16/0866; A61M 15/00
USPC ............... 128/203.12, 204.25; 600/538, 539
See application file for complete search history.

(56) References Cited

U.S. PATENT DOCUMENTS

| | | |
|---|---|---|
| 2,670,739 A | 3/1954 | NcNeill |
| 2,918,917 A | 12/1959 | Emerson |
| 3,486,502 A | 12/1969 | Wilson |
| 3,710,780 A | 1/1973 | Milch |
| 3,908,987 A | 9/1975 | Boehringer |
| 4,054,134 A | 10/1977 | Kritzer |
| 4,062,358 A | 12/1977 | Kritzer |
| 4,182,366 A | 1/1980 | Boehringer |
| 4,198,969 A | 4/1980 | Virag |
| 4,210,174 A | 7/1980 | Eross |
| 4,221,381 A | 9/1980 | Ericson |
| 4,226,233 A | 10/1980 | Kritzer |
| 4,231,375 A | 11/1980 | Boehringer et al. |
| 4,267,832 A | 5/1981 | Hakkinen |
| 4,275,722 A | 6/1981 | Sorensen |
| 4,298,023 A | 11/1981 | McGinnis |
| 4,327,740 A | 5/1982 | Shuman |
| 4,403,616 A | 9/1983 | King |
| 4,436,090 A | 3/1984 | Darling |
| 4,470,412 A | 9/1984 | Nowacki et al. |
| 4,473,082 A | 9/1984 | Gereg |
| 4,487,207 A | 12/1984 | Fitz |
| 4,533,137 A | 8/1985 | Sonne |
| 4,601,465 A | 7/1986 | Roy |
| 4,611,591 A | 9/1986 | Inui et al. |
| 4,635,631 A | 1/1987 | Izumi |
| 4,651,731 A | 3/1987 | Vicenzi et al. |
| 4,739,987 A | 4/1988 | Nicholson |
| 4,770,413 A | 9/1988 | Green |
| 4,854,574 A | 8/1989 | Larson |
| 4,951,661 A | 8/1990 | Sladek |
| 4,973,047 A | 11/1990 | Norell |
| 4,981,295 A | 1/1991 | Belman et al. |
| 5,018,517 A | 5/1991 | Liardet |
| 5,042,467 A | 8/1991 | Foley |
| 5,065,746 A | 11/1991 | Steen |
| 5,190,036 A | 3/1993 | Linder |
| 5,193,529 A | 3/1993 | Labaere |
| 5,345,930 A | 9/1994 | Cardinal et al. |
| 5,372,128 A | 12/1994 | Haber et al. |
| 5,381,789 A | 1/1995 | Marquardt |
| 5,397,337 A | 3/1995 | Jaeger et al. |
| 5,451,190 A | 9/1995 | Liardet |
| 5,479,920 A | 1/1996 | Piper et al. |
| 5,540,220 A | 7/1996 | Gropper et al. |
| 5,569,122 A | 10/1996 | Cegla |
| 5,570,682 A | 11/1996 | Johnson |
| 5,598,839 A | 2/1997 | Niles et al. |
| 5,613,489 A | 3/1997 | Miller |
| 5,645,049 A | 7/1997 | Foley et al. |
| 5,647,345 A | 7/1997 | Saul |
| 5,655,520 A | 8/1997 | Howe |
| 5,658,221 A | 8/1997 | Hougen |
| 5,727,546 A | 3/1998 | Clarke et al. |
| 5,791,339 A | 8/1998 | Winter |
| 5,829,429 A | 11/1998 | Hughes |
| 5,848,588 A | 12/1998 | Foley et al. |
| 5,857,957 A | 1/1999 | Lin |
| 5,862,802 A | 1/1999 | Bird |
| 5,890,998 A | 4/1999 | Hougen |
| 5,893,361 A | 4/1999 | Hughes |
| 5,896,857 A | 4/1999 | Hely |
| 5,899,832 A | 5/1999 | Hougen |
| 5,910,071 A | 6/1999 | Hougen |
| 5,925,831 A | 7/1999 | Storsved |
| 5,988,166 A | 11/1999 | Hayek |
| 6,026,807 A | 2/2000 | Puderbaugh et al. |
| 6,029,661 A | 2/2000 | Whaley et al. |
| 6,044,841 A | 4/2000 | Verdun et al. |
| 6,058,932 A | 5/2000 | Hughes |
| 6,066,101 A | 5/2000 | Johnson |
| 6,067,984 A | 5/2000 | Piper |
| 6,083,141 A | 7/2000 | Hougen |
| 6,089,105 A | 7/2000 | Ricciardelli |
| 6,102,038 A | 8/2000 | DeVries |
| 6,167,881 B1 | 1/2001 | Hughes |
| 6,176,235 B1 | 1/2001 | Benarrouch et al. |
| 6,182,657 B1 | 2/2001 | Brydon et al. |
| D440,651 S | 4/2001 | Foran |
| 6,240,917 B1 | 6/2001 | Andrade |
| 6,253,766 B1 | 7/2001 | Niles |
| 6,269,839 B1 | 8/2001 | Wickham et al. |
| 6,293,279 B1 | 9/2001 | Schmidt et al. |
| 6,340,025 B1 | 1/2002 | Van Brunt |
| 6,345,617 B1 | 2/2002 | Engelbreth et al. |
| 6,412,481 B1 | 7/2002 | Bienvenu et al. |
| 6,446,629 B1 | 9/2002 | Takaki et al. |
| 6,447,459 B1 | 9/2002 | Larom |
| 6,500,095 B1 | 12/2002 | Hougen |
| 6,539,938 B2 | 4/2003 | Weinstein et al. |
| 6,557,549 B2 | 5/2003 | Schmidt et al. |
| 6,581,595 B1 | 6/2003 | Murdock et al. |
| 6,581,596 B1 | 6/2003 | Truitt |
| 6,581,598 B1 | 6/2003 | Foran et al. |
| 6,581,600 B2 | 6/2003 | Bird |
| 6,595,203 B1 | 7/2003 | Bird |
| 6,606,989 B1 | 8/2003 | Brand |
| 6,607,008 B1 | 8/2003 | Yoshimoto et al. |
| 6,615,831 B1 | 9/2003 | Truitt |
| 6,631,721 B1 | 10/2003 | Salter et al. |
| 6,659,100 B2 | 12/2003 | O'Rourke |
| 6,681,768 B2 | 1/2004 | Haaije de Boer et al. |
| 6,702,769 B1 | 3/2004 | Fowler-Hawkins |
| 6,708,690 B1 | 3/2004 | Hete et al. |
| 6,708,691 B1 | 3/2004 | Hayek |
| 6,726,598 B1 | 4/2004 | Jarvis |
| D490,519 S | 5/2004 | Pelerossi et al. |
| 6,776,159 B2 | 8/2004 | Pelerossi et al. |
| 6,848,443 B2 | 2/2005 | Schmidt et al. |
| 6,851,425 B2 | 2/2005 | Jaffre |
| 6,860,265 B1 | 3/2005 | Emerson |
| 6,889,687 B1 | 5/2005 | Olsson |
| 6,904,906 B2 | 6/2005 | Salter |
| 6,923,181 B2 | 8/2005 | Tuck |
| 6,929,007 B2 | 8/2005 | Emerson |
| 6,984,214 B2 | 1/2006 | Fowler-Hawkins |
| 6,986,349 B2 | 1/2006 | Lurie |
| 7,059,324 B2 | 6/2006 | Pelerossi et al. |
| 7,096,866 B2 | 8/2006 | Be'eri et al. |
| 7,134,434 B2 | 11/2006 | Truitt et al. |
| 7,165,547 B2 | 1/2007 | Truitt et al. |
| 7,188,621 B2 | 3/2007 | DeVries |
| 7,191,776 B2 | 3/2007 | Niles |
| 7,191,780 B2 | 3/2007 | Faram |
| 7,214,170 B2 | 5/2007 | Summers et al. |
| 7,338,515 B2 | 3/2008 | Duren |
| 7,383,740 B2 | 6/2008 | Krasilchikov et al. |
| 7,617,821 B2 | 11/2009 | Hughes |
| 7,699,054 B2 | 4/2010 | Pelerossi et al. |
| 7,717,847 B2 | 5/2010 | Smith |
| 7,771,472 B2 | 8/2010 | Hendricksen |
| 7,779,841 B2 | 8/2010 | Dunsmore et al. |
| 7,798,148 B2 | 9/2010 | Doshi |
| 7,856,979 B2 | 12/2010 | Doshi |
| 7,909,033 B2 | 3/2011 | Faram |
| 7,927,293 B1 | 4/2011 | Ignagni et al. |
| 8,006,922 B2 | 8/2011 | Katzer |
| 8,025,051 B2 | 9/2011 | Dagsland |
| 8,025,054 B2 | 9/2011 | Dunsmore et al. |
| 8,043,236 B2 | 10/2011 | Goldshtein et al. |
| 8,051,854 B2 | 11/2011 | Faram |
| RE43,174 E | 2/2012 | Schmidt et al. |
| 8,118,024 B2 | 2/2012 | DeVries et al. |
| 8,118,713 B2 | 2/2012 | Foley et al. |
| 8,225,785 B2 | 7/2012 | Richards et al. |
| 8,251,876 B2 | 8/2012 | Boerst |

(56) References Cited

U.S. PATENT DOCUMENTS

| | | | |
|---|---|---|---|
| 8,327,849 | B2 | 12/2012 | Grychowski et al. |
| 8,360,061 | B2 | 1/2013 | Brown |
| 8,460,223 | B2 | 6/2013 | Huster et al. |
| 8,469,029 | B2 | 6/2013 | Brown et al. |
| 8,485,179 | B1 | 7/2013 | Meyer |
| 8,528,547 | B2 | 9/2013 | Dunsmore |
| 8,539,951 | B1 | 9/2013 | Meyer et al. |
| 8,539,952 | B2 | 9/2013 | Ikei et al. |
| 8,783,247 | B2 | 7/2014 | Newman |
| 8,985,111 | B2 | 3/2015 | Grychowski et al. |
| 8,993,774 | B2 | 3/2015 | Kanbara et al. |
| D731,050 | S | 6/2015 | Meyer |
| 9,149,589 | B2 | 10/2015 | Meyer et al. |
| 9,220,855 | B2 | 12/2015 | Meyer |
| 9,358,417 | B2 | 6/2016 | Meyer |
| 9,517,315 | B2 | 12/2016 | Meyer |
| D776,804 | S | 1/2017 | Meyer |
| D778,429 | S | 2/2017 | Engelbreth et al. |
| D780,906 | S | 3/2017 | Engelbreth et al. |
| 9,636,473 | B2 | 5/2017 | Meyer |
| 9,737,677 | B2 | 8/2017 | Grychowski et al. |
| 9,808,588 | B1 | 11/2017 | Meyer et al. |
| 9,849,257 | B2 | 12/2017 | Meyer et al. |
| 9,913,955 | B2 | 3/2018 | Grychowski et al. |
| 9,950,128 | B2 | 4/2018 | Meyer et al. |
| 9,981,106 | B2 | 5/2018 | Meyer et al. |
| 10,039,691 | B2 | 8/2018 | Von Hollen |
| 10,076,616 | B2 | 9/2018 | Meyer et al. |
| 10,272,222 | B2 | 4/2019 | Davis |
| 10,272,224 | B2 | 4/2019 | Costella et al. |
| 10,363,383 | B2 | 7/2019 | Alizoti et al. |
| 10,413,698 | B2 | 9/2019 | Meyer et al. |
| 2006/0032607 | A1 | 2/2006 | Wisniewski |
| 2007/0089740 | A1 | 4/2007 | Baumert et al. |
| 2007/0259759 | A1 | 11/2007 | Sumners et al. |
| 2008/0096728 | A1 | 4/2008 | Foley |
| 2008/0257348 | A1 | 10/2008 | Piper |
| 2009/0241949 | A1 | 10/2009 | Smutney et al. |
| 2010/0139655 | A1 | 6/2010 | Genosar |
| 2010/0307487 | A1 | 12/2010 | Dunsmore et al. |
| 2012/0097164 | A1 | 4/2012 | Rozario et al. |
| 2012/0111329 | A1 | 5/2012 | Brand et al. |
| 2014/0150790 | A1* | 6/2014 | Meyer ............... A61M 16/0006 128/204.18 |
| 2015/0013671 | A1* | 1/2015 | Costella ............. A61M 16/201 128/204.19 |
| 2015/0374939 | A1 | 12/2015 | Meyer et al. |
| 2016/0129213 | A1 | 5/2016 | Zhu et al. |
| 2016/0279375 | A1 | 9/2016 | Devries et al. |
| 2017/0028161 | A1 | 2/2017 | Meyer et al. |
| 2017/0049979 | A1 | 2/2017 | Meyer et al. |
| 2017/0128683 | A1 | 5/2017 | Meyer et al. |
| 2017/0312461 | A1 | 11/2017 | Grychowski et al. |
| 2017/0325735 | A1 | 11/2017 | Brand et al. |
| 2018/0008790 | A1 | 1/2018 | Costella et al. |
| 2018/0154093 | A1 | 6/2018 | Meyer et al. |
| 2018/0214662 | A1 | 8/2018 | Meyer et al. |
| 2018/0256839 | A1 | 9/2018 | Meyer et al. |
| 2019/0240533 | A1 | 8/2019 | Alizoti |

FOREIGN PATENT DOCUMENTS

| | | |
|---|---|---|
| EP | 0 678 306 A2 | 10/1995 |
| EP | 1 464 357 A1 | 10/2004 |
| EP | 1 435 251 B1 | 6/2006 |
| EP | 1 103 287 B1 | 6/2007 |
| EP | 1 897 576 A1 | 3/2008 |
| EP | 1 908 489 A1 | 4/2008 |
| EP | 2444114 A1 | 4/2012 |
| EP | 2455137 A2 | 5/2012 |
| GB | 2 425 488 A | 11/2006 |
| WO | WO 1989/03707 A1 | 5/1989 |
| WO | WO 1996/40376 A1 | 12/1996 |
| WO | WO 1999/16490 A1 | 4/1999 |
| WO | WO 2000/27455 A1 | 5/2000 |
| WO | WO 01/89618 A1 | 11/2001 |
| WO | WO 2007/061648 A3 | 5/2007 |
| WO | WO 2007/119104 A3 | 10/2007 |
| WO | WO 2008/063966 A1 | 5/2008 |
| WO | WO 2008/122045 A1 | 10/2008 |
| WO | WO 2009/131965 | 10/2009 |
| WO | WO 2011/010279 A1 | 1/2011 |
| WO | WO 2011/058470 | 5/2011 |
| WO | WO 2012/038864 A2 | 3/2012 |
| WO | WO 2012/042255 A1 | 4/2012 |
| WO | WO 2013/001398 A1 | 1/2013 |
| WO | WO 2014/202923 | 12/2014 |
| WO | WO 2014/202924 | 12/2014 |
| WO | WO 2014/203115 | 12/2014 |
| WO | WO 2016/012740 | 1/2016 |

OTHER PUBLICATIONS

Web page entitled Bronchial Hygiene, acapella Vibratory PEP Therapy System accessed from http://www.smiths-medical.com/catalog/bronchial-hygiene/acapella/acapella.html on Jul. 7, 2009.

Web page entitled Thayer Quake accessed from http://www.thayermedical.com/quake.htm on Jul. 7, 2009.

Human growth hormone, cortisol, and acid-base balance changes after hyperventilation and breath-holding; PubMed—indexed for MEDLINE; Int J Sports Med., Dec. 1986; 7(6):311-5, Djarova T.

Bosco C, Cardinale M. & Tsarpela O (1999). Influence of vibration on mechanical power and electromyogram activity in human arm flexor muscles. Eur J Appl Physiol 79, 306-311.

David Sumners; Power Breathing and Strength; http://EzineArticles.com/972576 Published: Feb. 7, 2008.

Good Vibrations blog; http://vibrotraining.blogspot.com, Earliest posting Jan. 17, 2008.

Breathtaking News; More Youbreathe; Aug. 10, 2007.

PCT International Search Report for PCT/IB2012/001089, dated Oct. 5, 2012.

PCT International Written Opinion for PCT/IB2012/001089, dated Oct. 5, 2012.

Preliminary Report on Patentability, PCT/IB2012/001089, dated Dec. 10, 2013.

PCT/IB2012001089 European Search Report dated Nov. 6, 2014.

PCT International Search Report for PCT/CA2014/000562 dated Oct. 16, 2014.

PCT Written Opinion for PCT/CA2014/000562 dated Oct. 16, 2014.

Supplemental European Search Report for related Application No. 14822301.9 dated Feb. 21, 2017 (8 pgs).

PCT International Search Report for PCT/IB2018/052899, dated Jul. 19, 2018; 5 pages.

PCT International Written Opinion for PCT/IB2018/052899, dated Jul. 19, 2018; 5 pages.

* cited by examiner

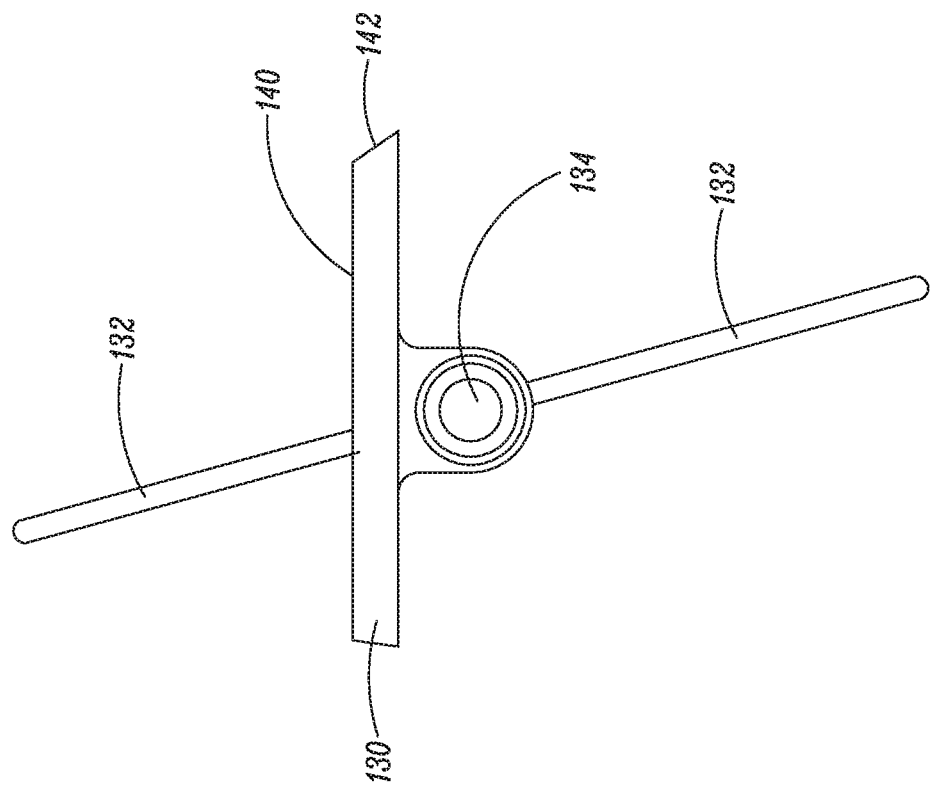
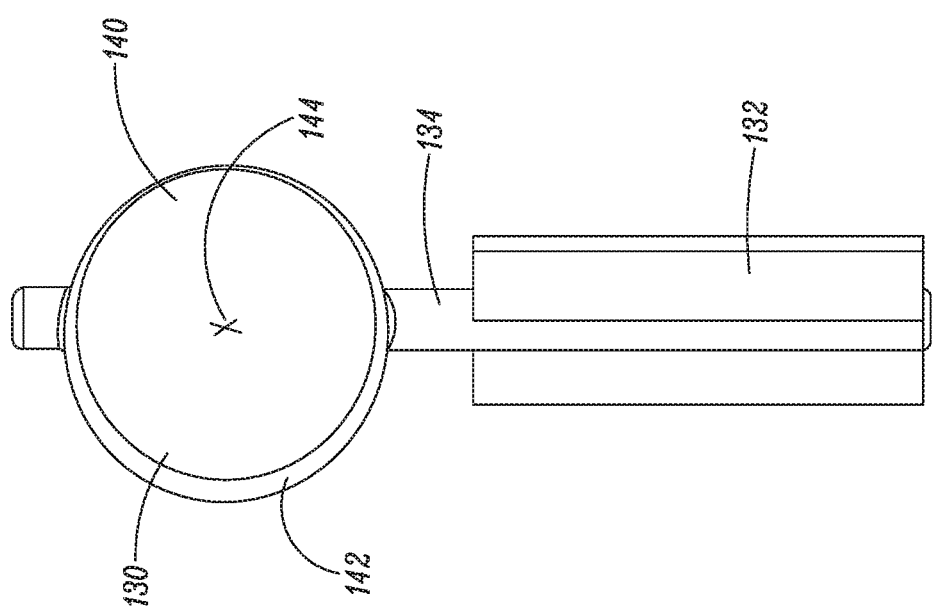

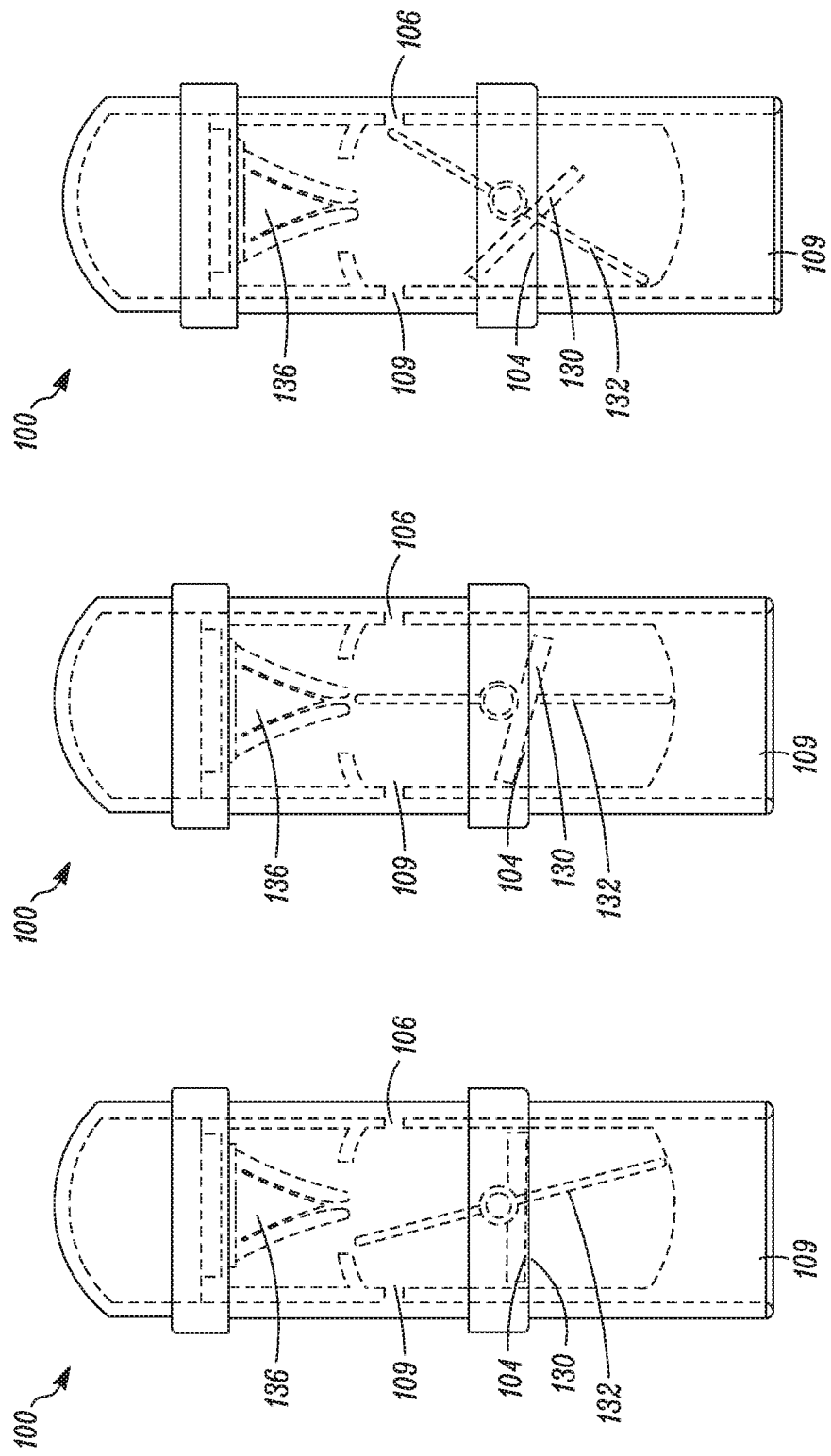

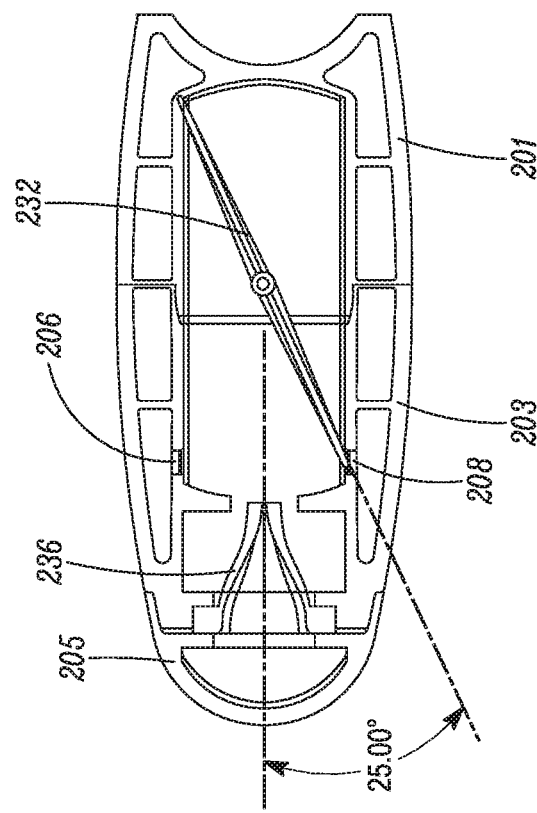
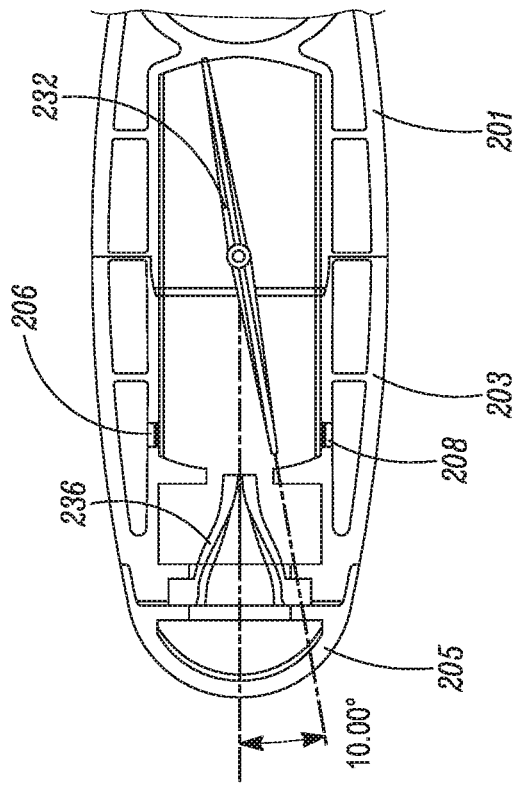
FIG. 32B
FIG. 32A

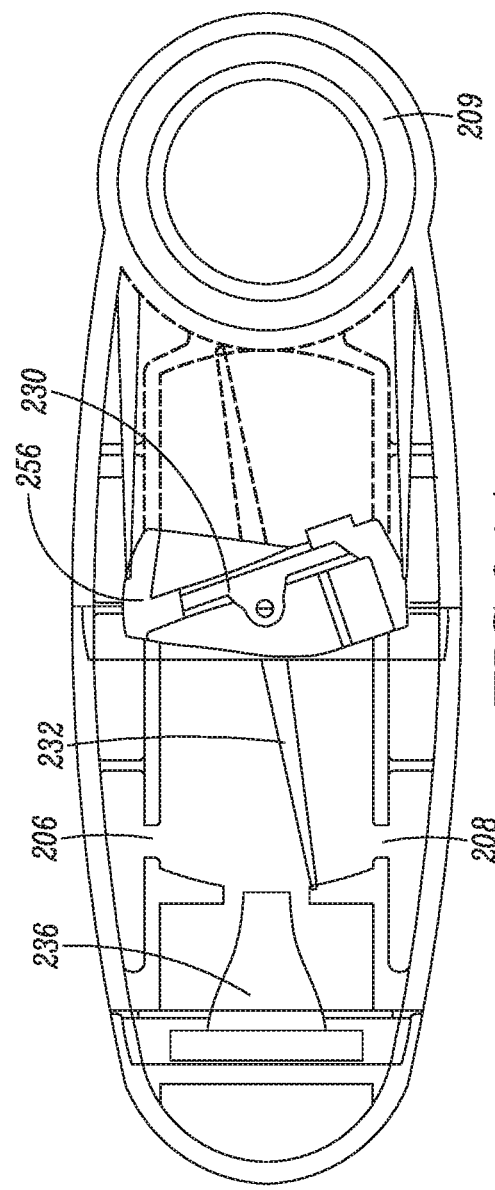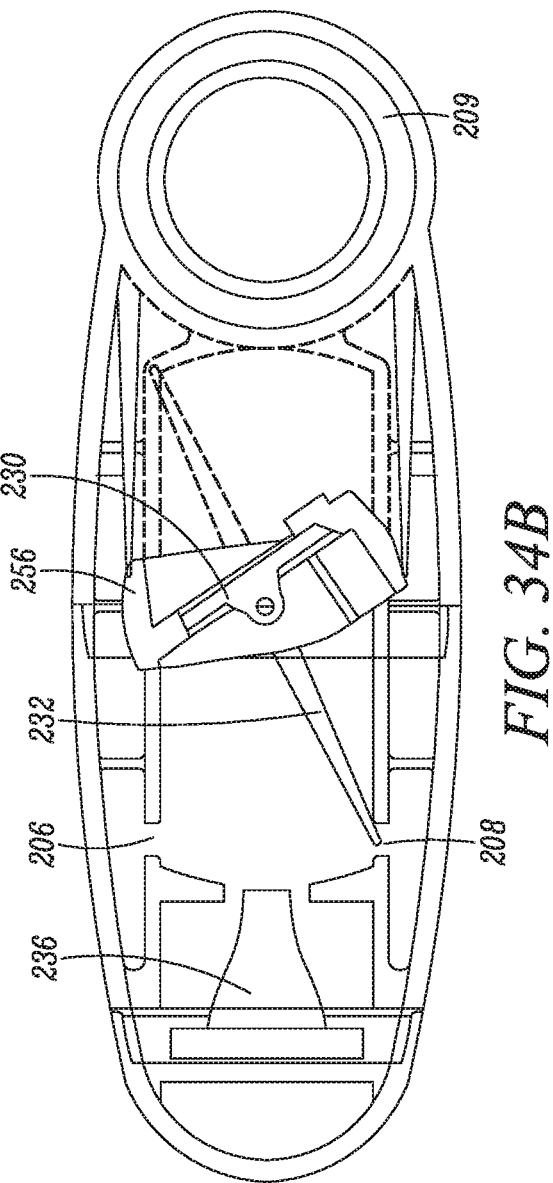

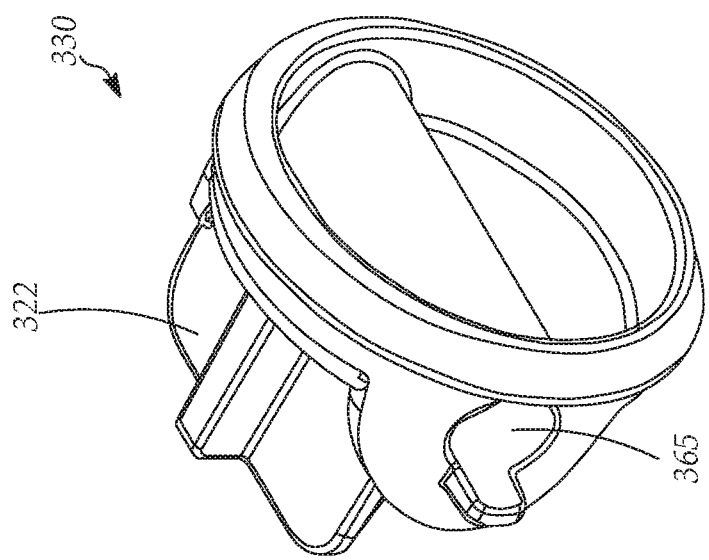
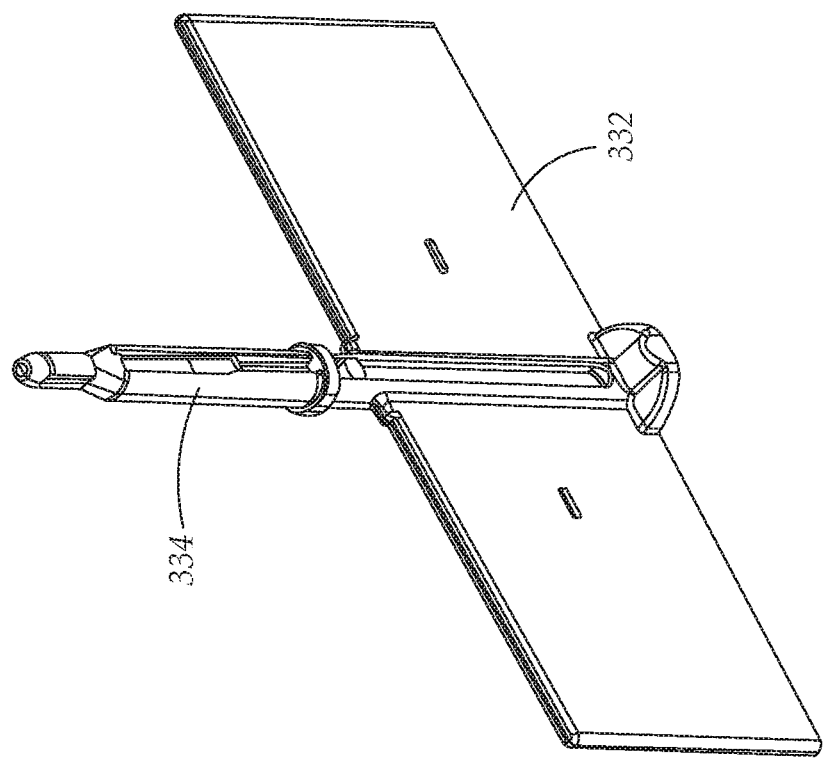
FIG. 44
FIG. 43

COMBINED OSCILLATING POSITIVE EXPIRATORY PRESSURE THERAPY AND HUFF COUGH SIMULATION DEVICE

TECHNICAL FIELD

The present disclosure relates to respiratory treatment devices, and in particular, to combined oscillating positive expiratory pressure ("OPEP") therapy and huff cough simulation devices.

BACKGROUND

Each day, humans may produce upwards of 30 milliliters of sputum, which is a type of bronchial secretion. Normally, an effective cough is sufficient to loosen secretions and clear them from the body's airways. However, for individuals suffering from more significant bronchial obstructions, such as collapsed airways, a single cough may be insufficient to clear the obstructions.

OPEP therapy represents an effective bronchial hygiene technique for the removal of bronchial secretions in the human body and is an important aspect in the treatment and continuing care of patients with bronchial obstructions, such as those suffering from chronic obstructive lung disease. It is believed that OPEP therapy, or the oscillation of exhalation pressure at the mouth during exhalation, effectively transmits an oscillating back pressure to the lungs, thereby splitting open obstructed airways and loosening the secretions contributing to bronchial obstructions.

OPEP therapy is an attractive form of treatment because it can be easily taught to most patients, and such patients can assume responsibility for the administration of OPEP therapy throughout a hospitalization and also from home. To that end, a number of portable OPEP devices have been developed.

The Huff Cough is also an effective technique for clearance of pulmonary secretions from the airways. It is often utilized in the treatment of COPD, or Chronic Obstructive Pulmonary Disease, although it may also be useful in other respiratory treatments. In general, the Huff Cough involves a patient using his or her diaphragm to breathe in slowly, holding the breath for two to three seconds, and forcing the breath out of his or her mouth in one quick burst of air, making sure the back of the throat is kept open. This technique is typically repeated multiple times during a single treatment. The length and force of the breath may be varied in order to treat different portions of a patient's airways. Despite its efficacy, the Huff Cough may be difficult for some populations to effectively perform, requiring coaching from respiratory professionals. To that end, a number of portable Huff Cough simulation devices have been developed.

As both OPEP therapy and Huff Cough simulation devices may be used to treat similar conditions or ailments, a portable, user friendly device capable of performing both OPEP therapy and simulating a Huff Cough is desirable.

BRIEF SUMMARY

In one aspect, a respiratory treatment device includes: an OPEP (oscillating positive expiratory pressure) mechanism having a restrictor member repeatedly moveable in response to air flow between a closed position where air flow through the OPEP mechanism is restricted, and an open position where air flow through the OPEP mechanism is less restricted; a Huff Cough mechanism having a valve moveable in response to a threshold exhalation pressure from a closed position where air flow through the Huff Cough mechanism is restricted, to an open position where air flow through the Huff Cough mechanism is less restricted; a user interface; and, a conduit leading from the user interface to the OPEP mechanism and the Huff Cough mechanism.

Air flow through the conduit may be selectively directed to the OPEP mechanism and the Huff Cough mechanism. Or, air flow through the conduit may be selectively directed to the OPEP mechanism, the Huff Cough mechanism, or both the OPEP mechanism and the Huff Cough mechanism. Airflow through the conduit may pass through the Huff Cough mechanism, followed by the OPEP mechanism. A valve may be positioned in the conduit to selectively direct air flow to the OPEP mechanism and the Huff Cough mechanism.

The OPEP mechanism may be positioned along a first segment of the conduit and the Huff Cough mechanism may positioned along a second segment of the conduit, such that air flow through the first segment does not traverse the second segment, and air flow through the second segment does not traverse the first segment.

A valve may be positioned in the first segment. The valve may be selectively moveable between an open position where air flow through the first segment to the OPEP device is permitted, and a closed position where air flow through the first segment to the OPEP device is not permitted. The valve may be selectively moveable between the open position to provide OPEP therapy, and the closed position to provide a Huff Cough simulation.

The valve of the Huff Cough mechanism may be configured to open in response to inhalation at the user interface.

The user interface may be moveable relative to the conduit between a first position, where the flow of air through the conduit to the OPEP mechanism is permitted, and a second position where the flow of air to the OPEP device is not permitted.

The valve may be positioned along a first segment of the conduit and the Huff Cough mechanism may be positioned along a second segment of the conduit, where airflow along the first segment does not traverse the second segment, and airflow along the second segment does not traverse the first segment. The OPEP mechanism may be positioned along a third segment of the conduit where the first segment and the second segment are joined. Again, the valve may be selectively moveable between an open position where air flow along the first segment is permitted, and a closed position where airflow along the first segment is not permitted. The valve may be selectively moveable between the open position to provide OPEP therapy, and the closed position to provide a Huff Cough simulation followed by OPEP therapy.

The Huff Cough mechanism and a finger within the device may be selectively moveable relative to one another to open the valve of the Huff Cough mechanism.

The OPEP mechanism may be positioned along a third segment of the conduit where the first segment and the second segment are joined, with a second valve positioned along a fourth segment of the conduit where the first segment and the second segment are joined, such that airflow along the third segment does not traverse the fourth segment, and airflow along the fourth segment does not traverse the third segment. The valve may be selectively moveable between an open position where air flow along the first segment is permitted, and a closed position where airflow along the first segment is not permitted. The second valve may be selectively moveable between an open position where air flow along the fourth segment is permitted, and a closed position where airflow along the fourth segment is not permitted.

The device may be selectively configured to provide a Huff Cough simulation without OPEP therapy when the valve is in the closed position and the second valve is in the open position. Alternatively, the device may be selectively configured to provide OPEP therapy without any Huff Cough simulation when the valve is in the open position and the second valve is in the closed position. Alternatively, the device may be selectively configured to provide a Huff Cough simulation followed by OPEP therapy when the valve is in the closed position and the second valve is in the closed position.

An inhalation valve may be positioned along the conduit. Airflow between the inhalation valve and the user interface may not pass through the OPEP mechanism or the Huff Cough mechanism. A switch may be moveable relative to the inhalation valve between a first position where the switch engages and maintains the inhalation valve in an open position, and a second position where the switch is not engaged with the inhalation valve.

BRIEF DESCRIPTION OF THE DRAWINGS

FIG. 10 is a front view of the restrictor member operatively connected to the vane shown in FIG. 8;

FIG. 11 is a top view of the restrictor member operatively connected to the vane shown in FIG. 8;

FIGS. 15A-C are top phantom views of the OPEP device of FIG. 1 showing an exemplary illustration of the operation of the OPEP device of FIG. 1;

FIGS. 32A-B are partial cross-sectional views taken along line III in FIG. 18 of the OPEP device, illustrating possible configurations of the OPEP device;

FIGS. 34A-B are top phantom views of the OPEP device of FIG. 18, illustrating the adjustability of the OPEP device;

FIG. 43 is a perspective view of a vane of the OPEP device of FIG. 35;

FIG. 44 is a front perspective view of a restrictor member of the OPEP device of FIG. 35;

DETAILED DESCRIPTION

Figure 1:
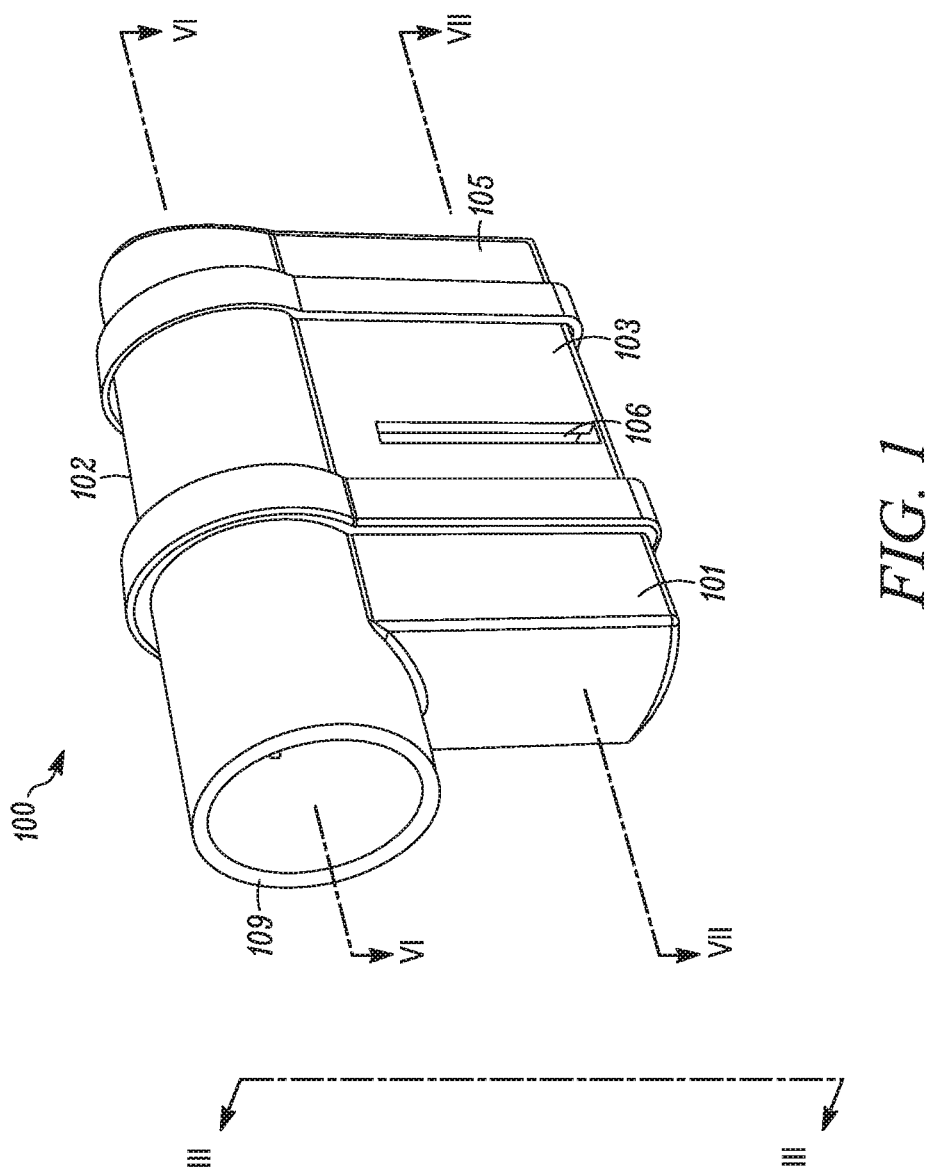
FIG. 1 is a front perspective view of an OPEP device.
Figure 2:
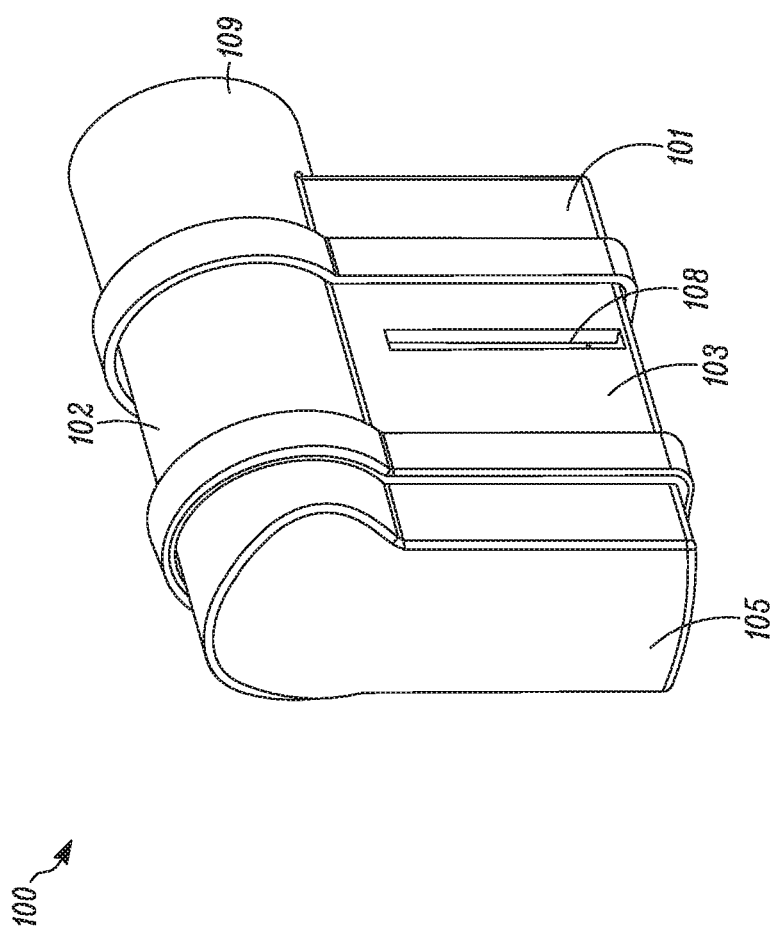
FIG. 2 is a rear perspective view of the OPEP device of FIG. 1.

Described herein are various embodiments and configurations of devices capable of selectively administering OPEP therapy and simulating a Huff Cough, both individually and in combination. It should be appreciated that existing OPEP devices and Huff Cough simulation devices may be used and/or modified for use in a combined OPEP and Huff Cough simulation device, as described herein. Exemplary OPEP devices and Huff Cough simulation devices suitable for use and/or modified for use in a combined OPEP and Huff Cough simulation device according to the present disclosure are described below.

Solely by way of example, suitable OPEP device include those shown and described in U.S. Pat. Nos. 5,018,517; 6,581,598; 6,776,159; 7,059,324; 8,327,849; 8,539,951; 8,485,179; 9,358,417; and, U.S. patent application Ser. No. 14/092,091, the entireties of which are herein incorporated by reference. Suitable commercially available OPEP devices include AEROBIKA® from Trudell Medical International of London, Canada, ACAPELLA® from Smiths Medical of St. Paul, Minn., FLUTTER® from Axcan Scandipharm Inc. of Birmingham, Ala., and RC-CORONET® from Curaplex of Dublin, Ohio.

Similarly, and solely by way of example, suitable Huff Cough simulation devices include those shown and described in U.S. patent application Ser. No. 14/329,011 and International Appl. No. PCT/IB2016/057311, the entireties of which are herein incorporated by reference.

Opep Device—Embodiment One

Referring first to FIGS. 1-4, a front perspective view, a rear perspective view, a cross-sectional front perspective view, and an exploded view of an OPEP device 100 are shown. For purposes of illustration, the internal components of the OPEP device 100 are omitted in FIG. 3. The OPEP device 100 generally comprises a housing 102, a chamber inlet 104, a first chamber outlet 106, a second chamber outlet 108 (best seen in FIGS. 2 and 7), and a mouthpiece 109 in fluid communication with the chamber inlet 104. While the mouthpiece 109 is shown in FIGS. 1-4 as being integrally formed with the housing 102, it is envisioned that the mouthpiece 109 may be removable and replaceable with a mouthpiece 109 of a different size or shape, as required to maintain ideal operating conditions. In general, the housing 102 and the mouthpiece 109 may be constructed of any durable material, such as a polymer. One such material is Polypropylene. Alternatively, acrylonitrile butadiene styrene (ABS) may be used.

Alternatively, other or additional interfaces, such as breathing tubes or gas masks (not shown) may be attached in fluid communication with the mouthpiece 109 and/or associated with the housing 102. For example, the housing 102 may include an inhalation port (not shown) having a separate one-way inhalation valve (not shown) in fluid communication with the mouthpiece 109 to permit a user of the OPEP device 100 both to inhale the surrounding air through the one-way valve, and to exhale through the chamber inlet 104 without withdrawing the mouthpiece 109 of the OPEP device 100 between periods of inhalation and exhalation. In addition, any number of aerosol delivery devices may be connected to the OPEP device 100, for example, through the inhalation port mentioned above, for the simultaneous administration of aerosol and OPEP therapies. As such, the inhalation port may include, for example, an elastomeric adapter, or other flexible adapter, capable of accommodating the different mouthpieces or outlets of the particular aerosol delivery device that a user intends to use with the OPEP device 100.

In FIGS. 1-4, the housing 102 is generally box-shaped. However, a housing 102 of any shape may be used. Furthermore, the chamber inlet 104, the first chamber outlet 106, and the second chamber outlet 108 could be any shape or series of shapes, such as a plurality (i.e., more than one) of circular passages or linear slots. More importantly, it should be appreciated that the cross-sectional area of the chamber inlet 104, the first chamber outlet 106, and the second chamber outlet 108 are only a few of the factors influencing the ideal operating conditions described above.

Preferably, the housing 102 is openable so that the components contained therein can be periodically accessed, cleaned, replaced, or reconfigured, as required to maintain the ideal operating conditions. As such, the housing 102 is shown in FIGS. 1-4 as comprising a front section 101, a middle section 103, and a rear section 105. The front section 101, the middle section 103, and the rear section 105 may be removably connected to one another by any suitable means, such as a snap-fit, a compression fit, etc., such that a seal forms between the relative sections sufficient to permit the OPEP device 100 to properly administer OPEP therapy.

Figure 3:
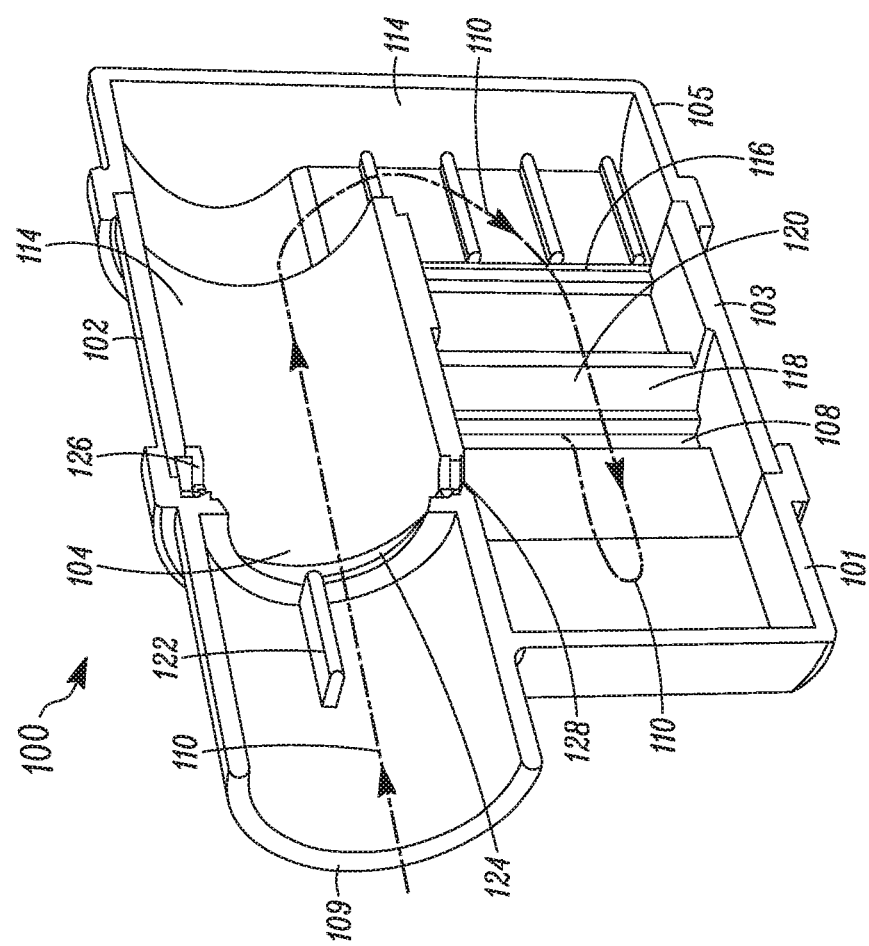
FIG. 3 is a cross-sectional perspective view taken along line III in FIG. 1 of the OPEP device shown without the internal components of the OPEP device.
Figure 7:
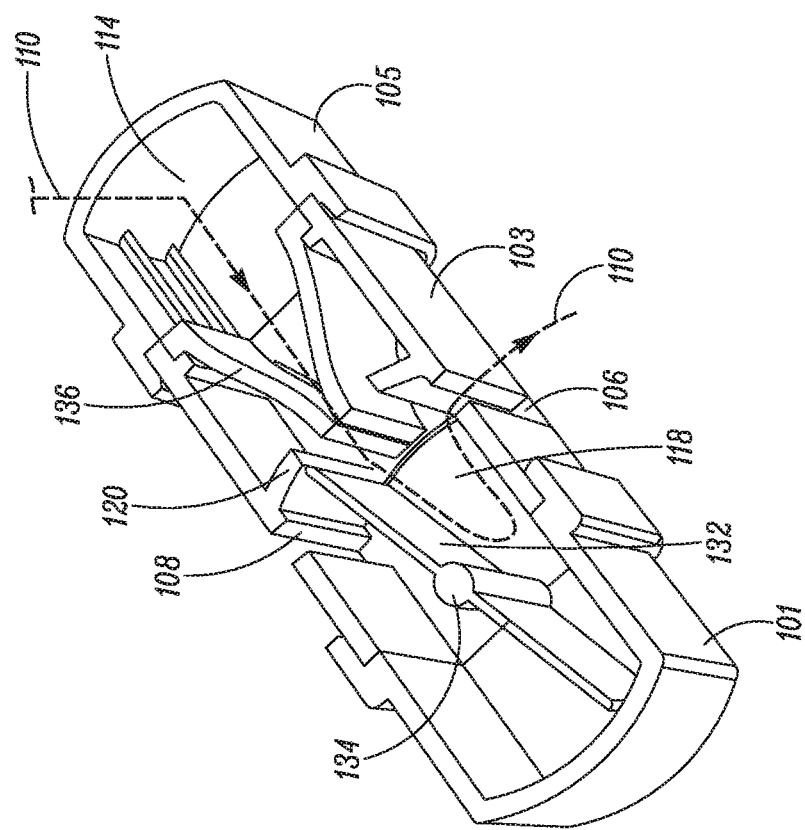
FIG. 7 is a different cross-sectional perspective view taken along line VII in FIG. 1 of the OPEP device shown with the internal components of the OPEP device.

As shown in FIG. 3, an exhalation flow path 110, identified by a dashed line, is defined between the mouthpiece 109 and at least one of the first chamber outlet 106 and the second chamber outlet 108 (best seen in FIG. 7). More specifically, the exhalation flow path 110 begins at the mouthpiece 109, passes through the chamber inlet 104, and enters into a first chamber 114, or an entry chamber. In the first chamber 114, the exhalation flow path makes a 180-degree turn, passes through a chamber passage 116, and enters into a second chamber 118, or an exit chamber. In the second chamber 118, the exhalation flow path 110 may exit the OPEP device 100 through at least one of the first chamber outlet 106 and the second chamber outlet 108. In this way, the exhalation flow path 110 is "folded" upon itself, i.e., it reverses longitudinal directions between the chamber inlet 104 and one of the first chamber outlet 106 or the second chamber outlet 108. However, those skilled in the art will appreciate that the exhalation flow path 110 identified by the dashed line is exemplary, and that air exhaled into the OPEP device 100 may flow in any number of directions or paths as it traverses from the mouthpiece 109 or chamber inlet 104 and the first chamber outlet 106 or the second chamber outlet 108.

FIG. 3 also shows various other features of the OPEP device 100 associated with the housing 102. For example, a stop 122 prevents a restrictor member 130 (see FIG. 5), described below, from opening in a wrong direction; a seat 124 shaped to accommodate the restrictor member 130 is formed about the chamber inlet 104; and, an upper bearing 126 and a lower bearing 128 are formed within the housing 102 and configured to accommodate a shaft rotatably mounted therebetween. One or more guide walls 120 are positioned in the second chamber 118 to direct exhaled air along the exhalation flow path 110.

Figure 5:
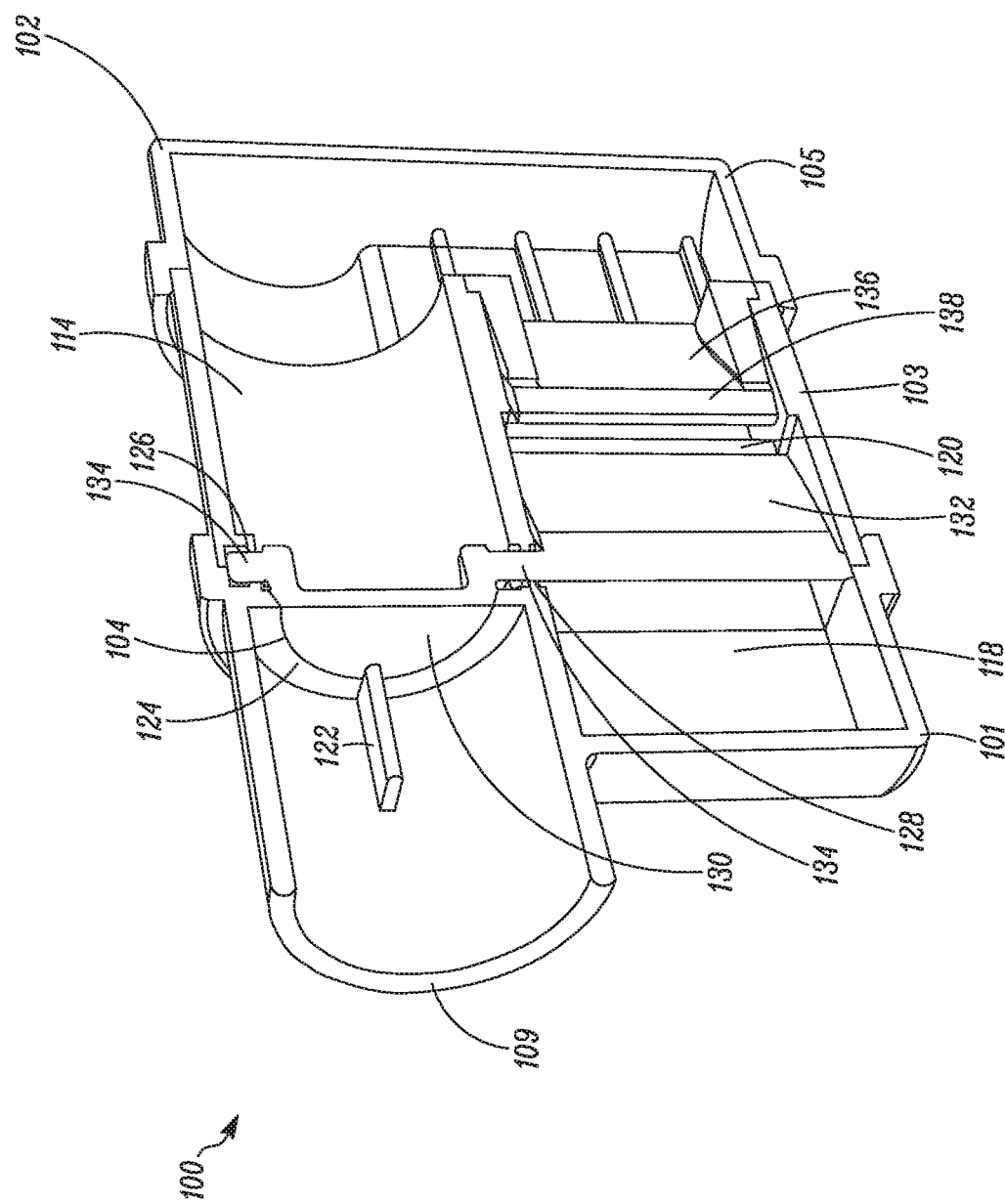
FIG. 5 is a cross-sectional perspective view taken along line III in FIG. 1 of the OPEP device shown with the internal components of the OPEP device.
Figure 6:
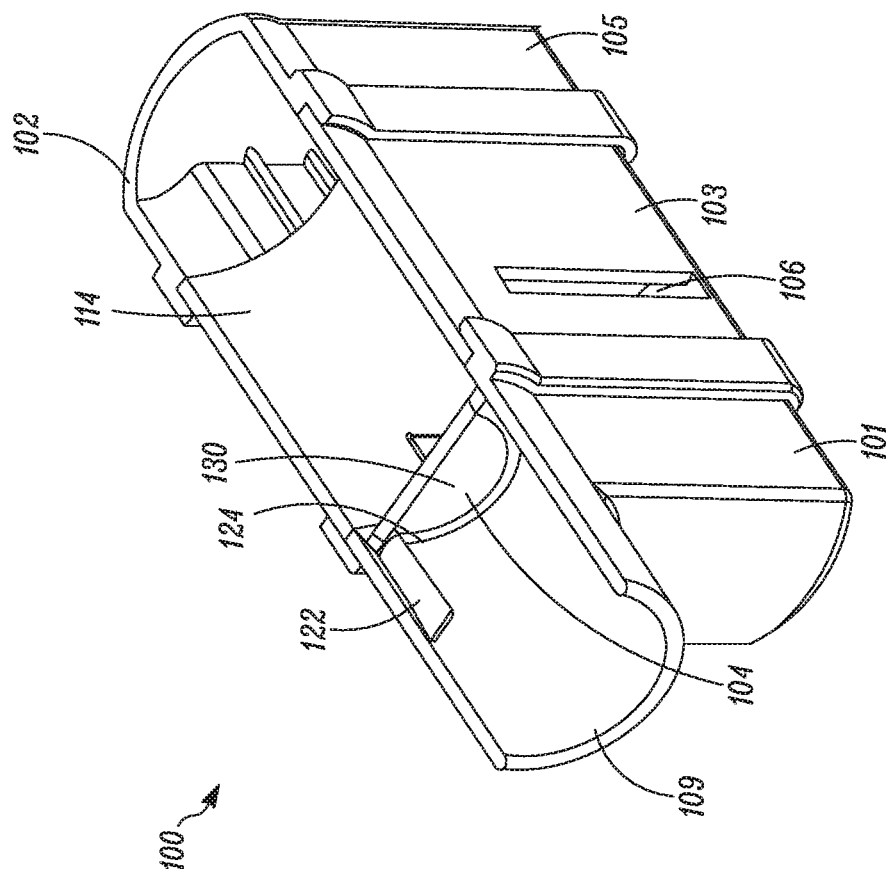
FIG. 6 is a different cross-sectional perspective view taken along line VI in FIG. 1 of the OPEP device shown with the internal components of the OPEP device.

Turning to FIGS. 5-7, various cross-sectional perspective views of the OPEP device 100 are shown with its internal components. The internal components of the OPEP device 100 comprise a restrictor member 130, a vane 132, and an optional variable nozzle 136. As shown, the restrictor member 130 and the vane 132 are operatively connected by means of a shaft 134 rotatably mounted between the upper bearing 126 and the lower bearing 128, such that the restrictor member 130 and the vane 132 are rotatable in unison about the shaft 134. As described below in further detail, the variable nozzle 136 includes an orifice 138 configured to increase in size in response to the flow of exhaled air therethrough.

Figure 4:
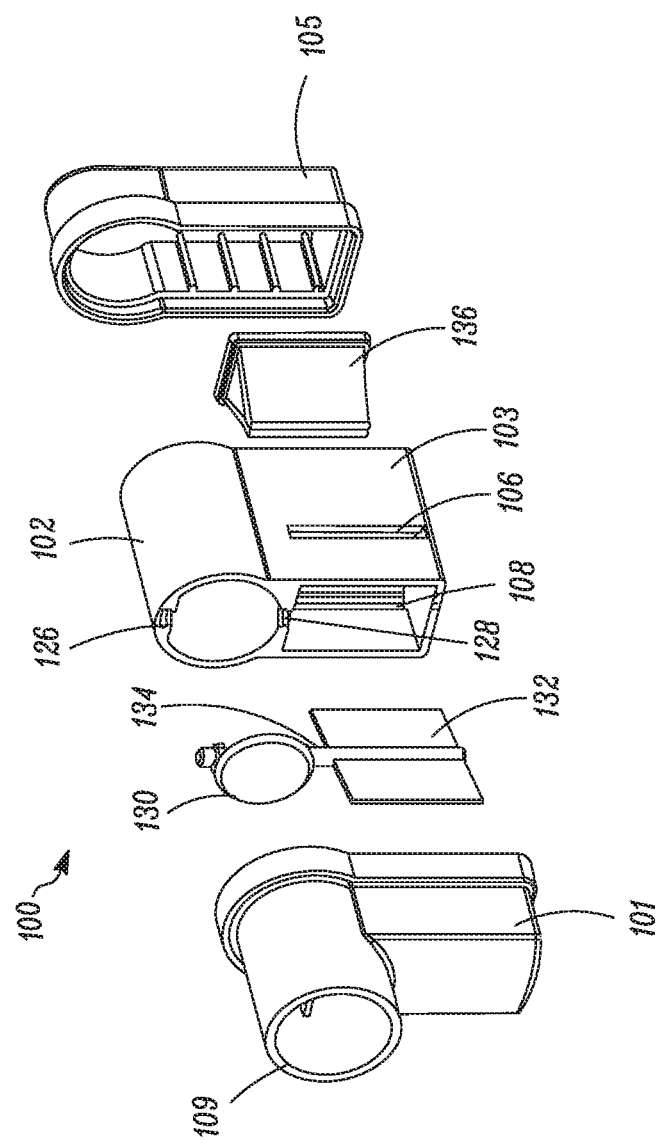
FIG. 4 is an exploded view of the OPEP device of FIG. 1, shown with the internal components of the OPEP device.

FIGS. 4-6 further illustrate the division of the first chamber 114 and the second chamber 118 within the housing 102. As previously described, the chamber inlet 104 defines an entrance to the first chamber 114. The restrictor member 130 is positioned in the first chamber 114 relative to a seat 124 about the chamber inlet 104 such that it is moveable between a closed position, where a flow of exhaled air along the exhalation flow path 110 through the chamber inlet 104 is restricted, and an open position, where the flow of exhaled air through the chamber inlet 104 is less restricted. Likewise, the variable nozzle 136, which is optional, is mounted about or positioned in the chamber passage 116, such that the flow of exhaled air entering the first chamber 114 exits the first chamber 114 through the orifice 138 of the variable nozzle 136. Exhaled air exiting the first chamber 114 through the orifice 138 of the variable nozzle 136 enters the second chamber, which is defined by the space within the housing 102 occupied by the vane 132 and the guide walls 120. Depending on the position of the vane 132, the exhaled air is then able to exit the second chamber 118 through at least one of the first chamber outlet 106 and the second chamber outlet 108.

Figure 9:
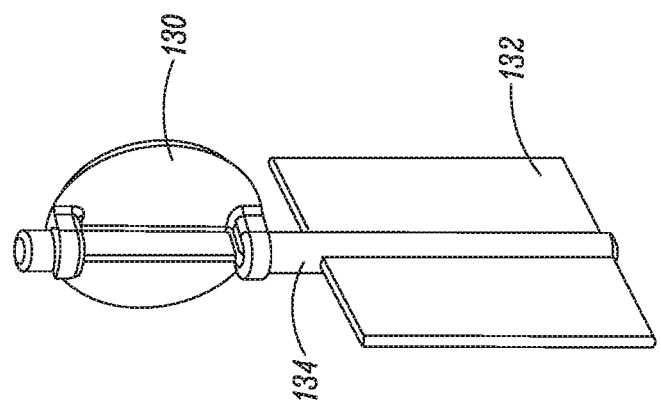
FIG. 9 is a rear perspective view of the restrictor member operatively connected to the vane shown in FIG. 8.
Figure 8:
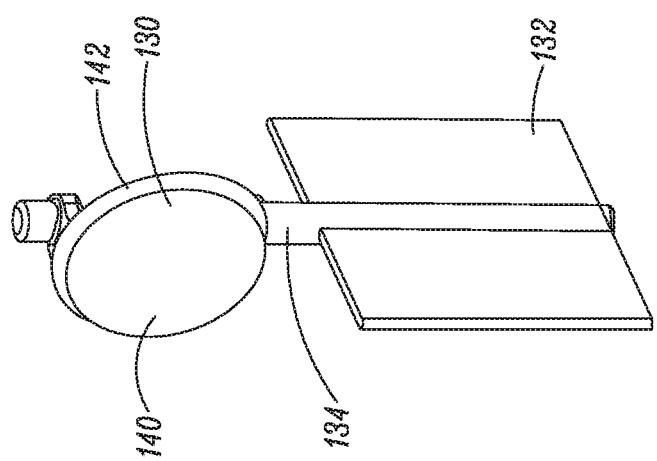
FIG. 8 is a front perspective view of a restrictor member operatively connected to a vane.

FIGS. 8-14 show the internal components of the OPEP device 100 in greater detail. Turning first to FIGS. 8-9, a front perspective view and a rear perspective view shows the restrictor member 130 operatively connected to the vane 132 by the shaft 134. As such, the restrictor member 130 and the vane 132 are rotatable about the shaft 134 such that rotation of the restrictor member 130 results in a corresponding rotation of the vane 132, and vice-versa. Like the housing 102, the restrictor member 130 and the vane 132 may be made of constructed of any durable material, such as a polymer. Preferably, they are constructed of a low shrink, low friction plastic. One such material is acetal.

As shown, the restrictor member 130, the vane 132, and the shaft 134 are formed as a unitary component. The restrictor member 130 is generally disk-shaped, and the vane 132 is planar. The restrictor member 130 includes a generally circular face 140 axially offset from the shaft 134 and a beveled or chamfered edge 142 shaped to engage the seat 124 formed about the chamber inlet 104. In this way, the restrictor member 130 is adapted to move relative to the chamber inlet 104 about an axis of rotation defined by the shaft 134 such that the restrictor member 130 may engage the seat 124 in a closed position to substantially seal and restrict the flow of exhaled air through the chamber inlet 104. However, it is envisioned that the restrictor member 130 and the vane 132 may be formed as separate components connectable by any suitable means such that they remain independently replaceable with a restrictor member 130 or a vane 132 of a different shape, size, or weight, as selected to maintain ideal operating conditions. For example, the restrictor member 130 and/or the vane 132 may include one or more contoured surfaces. Alternatively, the restrictor member 130 may be configured as a butterfly valve.

Turning to FIG. 10, a front view of the restrictor member 130 and the vane 132 is shown. As previously described, the restrictor member 130 comprises a generally circular face 140 axially offset from the shaft 134. The restrictor member 130 further comprises a second offset designed to facilitate movement of the restrictor member 130 between a closed position and an open position. More specifically, a center 144 of the face 140 of the restrictor member 130 is offset from the plane defined by the radial offset and the shaft 134, or the axis of rotation. In other words, a greater surface area of the face 140 of the restrictor member 130 is positioned on one side of the shaft 134 than on the other side of the shaft 134. Pressure at the chamber inlet 104 derived from exhaled air produces a force acting on the face 140 of the restrictor member 130. Because the center 144 of the face 140 of the restrictor member 130 is offset as described above, a resulting force differential creates a torque about the shaft 134. As further explained below, this torque facilitates movement of the restrictor member 130 between a closed position and an open position.

Turning to FIG. 11, a top view of the restrictor member 130 and the vane 132 is shown. As illustrated, the vane 132 is connected to the shaft 134 at a 75° angle relative to the face 140 of restrictor member 130. Preferably, the angle will remain between 60° and 80°, although it is envisioned that the angle of the vane 132 may be selectively adjusted to maintain the ideal operating conditions, as previously discussed. It is also preferable that the vane 132 and the restrictor member 130 are configured such that when the OPEP device 100 is fully assembled, the angle between a centerline of the variable nozzle 136 and the vane 132 is between 10° and 25° when the restrictor member 130 is in a closed position. Moreover, regardless of the configuration, it is preferable that the combination of the restrictor member 130 and the vane 132 have a center of gravity aligned with the shaft 134, or the axis of rotation. In full view of the present disclosure, it should be apparent to those skilled in the art that the angle of the vane 132 may be limited by the size or shape of the housing 102, and will generally be less than half the total rotation of the vane 132 and the restrictor member 130.

Figure 13:
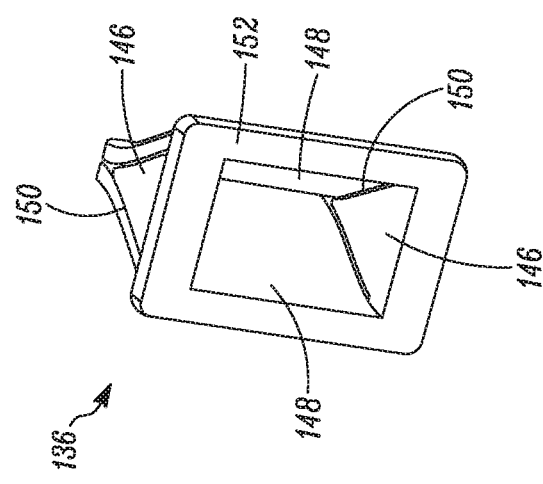
FIG. 13 is a rear perspective view of the variable nozzle of FIG. 12 shown without the flow of exhaled air therethrough.
Figure 12:
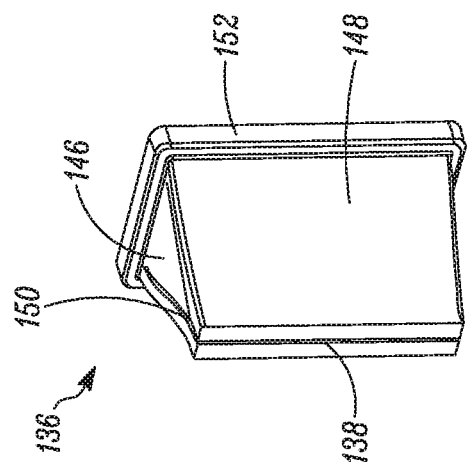
FIG. 12 is a front perspective view of a variable nozzle shown without the flow of exhaled air therethrough.

Turning to FIGS. 12 and 13, a front perspective view and a rear perspective view of the variable nozzle 136 is shown without the flow of exhaled air therethrough. In general, the variable nozzle 136 includes top and bottom walls 146, side walls 148, and V-shaped slits 150 formed therebetween. As shown, the variable nozzle is generally shaped like a duckbill type valve. However, it should be appreciated that nozzles or valves of other shapes and sizes may also be used. The variable nozzle 136 may also include a lip 152 configured to mount the variable nozzle 136 within the housing 102 between the first chamber 114 and the second chamber 118. The variable nozzle 136 may be constructed or molded of any material having a suitable flexibility, such as silicone, and preferably with a wall thickness of between 0.50 and 2.00 millimeters, and an orifice width between 0.25 to 1.00 millimeters, or smaller depending on manufacturing capabilities.

As previously described, the variable nozzle 136 is optional in the operation of the OPEP device 100. It should also be appreciated that the OPEP device 100 could alternatively omit both the chamber passage 116 and the variable nozzle 136, and thus comprise a single-chamber embodiment. Although functional without the variable nozzle 136, the performance of the OPEP device 100 over a wider range of exhalation flow rates is improved when the OPEP device 100 is operated with the variable nozzle 136. The chamber passage 116, when used without the variable nozzle 136, or the orifice 138 of the variable nozzle 136, when the variable nozzle 136 is included, serves to create a jet of exhaled air having an increased velocity. As explained in more detail below, the increased velocity of the exhaled air entering the second chamber 118 results in a proportional increase in the force applied by the exhaled air to the vane 132, and in turn, an increased torque about the shaft 134, all of which affect the ideal operating conditions.

Without the variable nozzle 136, the orifice between the first chamber 114 and the second chamber 118 is fixed according to the size, shape, and cross-sectional area of the chamber passage 116, which may be selectively adjusted by any suitable means, such as replacement of the middle section 103 or the rear section 105 of the housing. On the other hand, when the variable nozzle 136 is included in the OPEP device 100, the orifice between the first chamber 114 and the second chamber 118 is defined by the size, shape, and cross-sectional area of the orifice 138 of the variable nozzle 136, which may vary according to the flow rate of exhaled air and/or the pressure in the first chamber 114.

Figure 14:
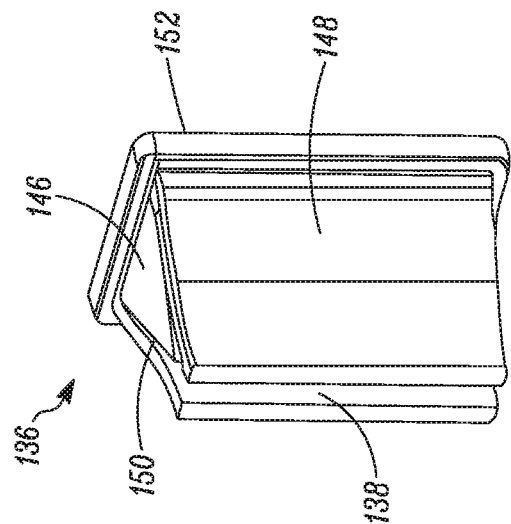
FIG. 14 is a front perspective view of the variable nozzle of FIG. 12 shown with a high flow of exhaled air therethrough.

Turning to FIG. 14, a front perspective view of the variable nozzle 136 is shown with a flow of exhaled air therethrough. One aspect of the variable nozzle 136 shown in FIG. 14 is that, as the orifice 138 opens in response to the flow of exhaled air therethrough, the cross-sectional shape of the orifice 138 remains generally rectangular, which during the administration of OPEP therapy results in a lower drop in pressure through the variable nozzle 136 from the first chamber 114 (See FIGS. 3 and 5) to the second chamber 118. The generally consistent rectangular shape of the orifice 138 of the variable nozzle 136 during increased flow rates is achieved by the V-shaped slits 150 formed between the top and bottom walls 146 and the side walls 148, which serve to permit the side walls 148 to flex without restriction. Preferably, the V-shaped slits 150 are as thin as possible to minimize the leakage of exhaled air therethrough. For example, the V-shaped slits 150 may be approximately 0.25 millimeters wide, but depending on manufacturing capabilities, could range between 0.10 and 0.50 millimeters. Exhaled air that does leak through the V-shaped slits 150 is ultimately directed along the exhalation flow path by the guide walls 120 in the second chamber 118 protruding from the housing 102.

It should be appreciated that numerous factors contribute to the impact the variable nozzle 136 has on the performance of the OPEP device 100, including the geometry and material of the variable nozzle 136. By way of example only, in order to attain a target oscillating pressure frequency of between 10 to 13 Hz at an exhalation flow rate of 15 liters per minute, in one embodiment, a 1.0 by 20.0 millimeter passage or orifice may be utilized. However, as the exhalation flow rate increases, the frequency of the oscillating pressure in that embodiment also increases, though at a rate too quickly in comparison to the target frequency. In order to attain a target oscillating pressure frequency of between 18 to 20 Hz at an exhalation flow rate of 45 liters per minute, the same embodiment may utilize a 3.0 by 20.0 millimeter passage or orifice. Such a relationship demonstrates the desirability of a passage or orifice that expands in cross-sectional area as the exhalation flow rate increases in order to limit the drop in pressure across the variable nozzle 136.

Turning to FIGS. 15A-C, top phantom views of the OPEP device 100 show an exemplary illustration of the operation of the OPEP device 100. Specifically, FIG. 15A shows the restrictor member 130 in an initial, or closed position, where the flow of exhaled air through the chamber inlet 104 is restricted, and the vane 132 is in a first position, directing the flow of exhaled air toward the first chamber outlet 106. FIG. 15B shows this restrictor member 130 in a partially open position, where the flow of exhaled air through the chamber inlet 104 is less restricted, and the vane 132 is directly aligned with the jet of exhaled air exiting the variable nozzle 136. FIG. 15C shows the restrictor member 130 in an open position, where the flow of exhaled air through the chamber inlet 104 is even less restricted, and the vane 132 is in a second position, directing the flow of exhaled air toward the second chamber outlet 108. It should be appreciated that the cycle described below is merely exemplary of the operation of the OPEP device 100, and that numerous factors may affect operation of the OPEP device 100 in a manner that results in a deviation from the described cycle. However, during the operation of the OPEP device 100, the restrictor member 130 and the vane 132 will generally reciprocate between the positions shown in FIGS. 15A and 15C.

During the administration of OPEP therapy, the restrictor member 130 and the vane 132 may be initially positioned as shown in FIG. 15A. In this position, the restrictor member 130 is in a closed position, where the flow of exhaled air along the exhalation path through the chamber inlet 104 is substantially restricted. As such, an exhalation pressure at the chamber inlet 104 begins to increase when a user exhales into the mouthpiece 108. As the exhalation pressure at the chamber inlet 104 increases, a corresponding force acting on the face 140 of the restrictor member 130 increases. As previously explained, because the center 144 of the face 140 is offset from the plane defined by the radial offset and the shaft 134, a resulting net force creates a negative or opening torque about the shaft. In turn, the opening torque biases the restrictor member 130 to rotate open, letting exhaled air enter the first chamber 114, and biases the vane 132 away from its first position. As the restrictor member 130 opens and exhaled air is let into the first chamber 114, the pressure at the chamber inlet 104 begins to decrease, the force acting on the face 140 of the restrictor member begins to decrease, and the torque biasing the restrictor member 130 open begins to decrease.

As exhaled air continues to enter the first chamber 114 through the chamber inlet 104, it is directed along the exhalation flow path 110 by the housing 102 until it reaches the chamber passage 116 disposed between the first chamber 114 and the second chamber 118. If the OPEP device 100 is being operated without the variable nozzle 136, the exhaled air accelerates through the chamber passage 116 due to the decrease in cross-sectional area to form a jet of exhaled air. Likewise, if the OPEP device 100 is being operated with the variable nozzle 136, the exhaled air accelerates through the orifice 138 of the variable nozzle 136, where the pressure through the orifice 138 causes the side walls 148 of the variable nozzle 136 to flex outward, thereby increasing the size of the orifice 138, as well as the resulting flow of exhaled air therethrough. To the extent some exhaled air leaks out of the V-shaped slits 150 of the variable nozzle 136, it is directed back toward the jet of exhaled air and along the exhalation flow path by the guide walls 120 protruding into the housing 102.

Then, as the exhaled air exits the first chamber 114 through the variable nozzle 136 and/or chamber passage 116 and enters the second chamber 118, it is directed by the vane 132 toward the front section 101 of the housing 102, where it is forced to reverse directions before exiting the OPEP device 100 through the open first chamber exit 106. As a result of the change in direction of the exhaled air toward the front section 101 of the housing 102, a pressure accumulates in the second chamber 118 near the front section 101 of the housing 102, thereby resulting in a force on the adjacent vane 132, and creating an additional negative or opening torque about the shaft 134. The combined opening torques created about the shaft 134 from the forces acting on the face 140 of the restrictor member 130 and the vane 132 cause the restrictor member 130 and the vane 132 to rotate about the shaft 134 from the position shown in FIG. 15A toward the position shown in FIG. 15B.

When the restrictor member 130 and the vane 132 rotate to the position shown in FIG. 15B, the vane 132 crosses the jet of exhaled air exiting the variable nozzle 136 or the chamber passage 116. Initially, the jet of exhaled air exiting the variable nozzle 136 or chamber passage 116 provides a force on the vane 132 that, along with the momentum of the vane 132, the shaft 134, and the restrictor member 130, propels the vane 132 and the restrictor member 130 to the position shown in FIG. 15C. However, around the position shown in FIG. 15B, the force acting on the vane 132 from the exhaled air exiting the variable nozzle 136 also switches from a negative or opening torque to a positive or closing torque. More specifically, as the exhaled air exits the first chamber 114 through the variable nozzle 136 and enters the second chamber 118, it is directed by the vane 132 toward the front section 101 of the housing 102, where it is forced to reverse directions before exiting the OPEP device 100 through the open second chamber exit 108. As a result of the change in direction of the exhaled air toward the front section 101 of the housing 102, a pressure accumulates in the second chamber 118 near the front section 101 of the housing 102, thereby resulting in a force on the adjacent vane 132, and creating a positive or closing torque about the shaft 134. As the vane 132 and the restrictor member 130 continue to move closer to the position shown in FIG. 15C, the pressure accumulating in the section chamber 118 near the front section 101 of the housing 102, and in turn, the positive or closing torque about the shaft 134, continues to increase, as the flow of exhaled air along the exhalation flow path 110 and through the chamber inlet 104 is even less restricted. Meanwhile, although the torque about the shaft 134 from the force acting on the restrictor member 130 also switches from a negative or opening torque to a positive or closing torque around the position shown in FIG. 15B, its magnitude is essentially negligible as the restrictor member 130 and the vane 132 rotate from the position shown in FIG. 15B to the position shown in FIG. 15C.

After reaching the position shown in FIG. 15C, and due to the increased positive or closing torque about the shaft 134, the vane 132 and the restrictor member 130 reverse directions and begin to rotate back toward the position shown in FIG. 15B. As the vane 132 and the restrictor member 130 approach the position shown in FIG. 15B, and the flow of exhaled through the chamber inlet 104 is increasingly restricted, the positive or closing torque about the shaft 134 begins to decrease. When the restrictor member 130 and the vane 132 reach the position 130 shown in FIG. 15B, the vane 132 crosses the jet of exhaled air exiting the variable nozzle 136 or the chamber passage 116, thereby creating a force on the vane 132 that, along with the momentum of the vane 132, the shaft 134, and the restrictor member 130, propels the vane 132 and the restrictor member 130 back to the position shown in FIG. 15A. After the restrictor member 130 and the vane 132 return to the position shown in FIG. 15A, the flow of exhaled air through the chamber inlet 104 is restricted, and the cycle described above repeats itself.

It should be appreciated that, during a single period of exhalation, the cycle described above will repeat numerous times. Thus, by repeatedly moving the restrictor member 130 between a closed position, where the flow of exhaled air through the chamber inlet 104 is restricted, and an open position, where the flow of exhaled air through the chamber inlet 104 is less restricted, an oscillating back pressure is transmitted to the user of the OPEP device 100 and OPEP therapy is administered.

Figure 16:
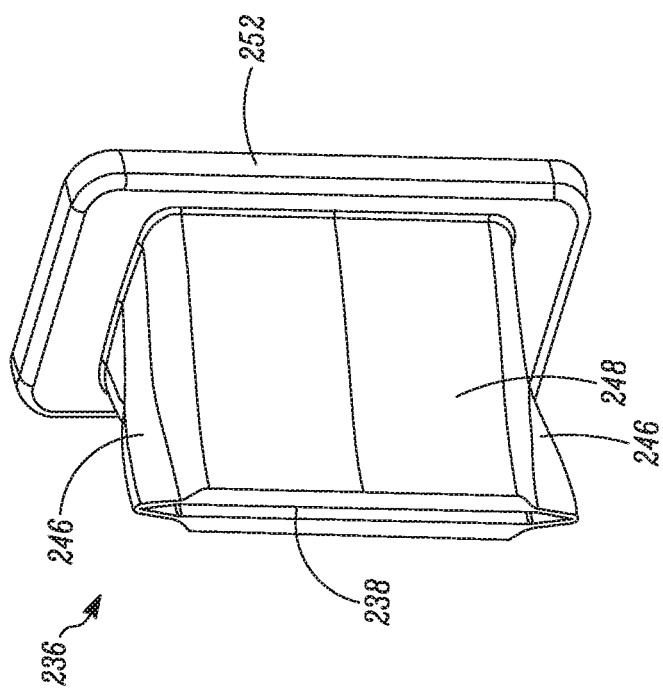
FIG. 16 is a front perspective view of a different embodiment of a variable nozzle shown without the flow of exhaled air therethrough.
Figure 17:
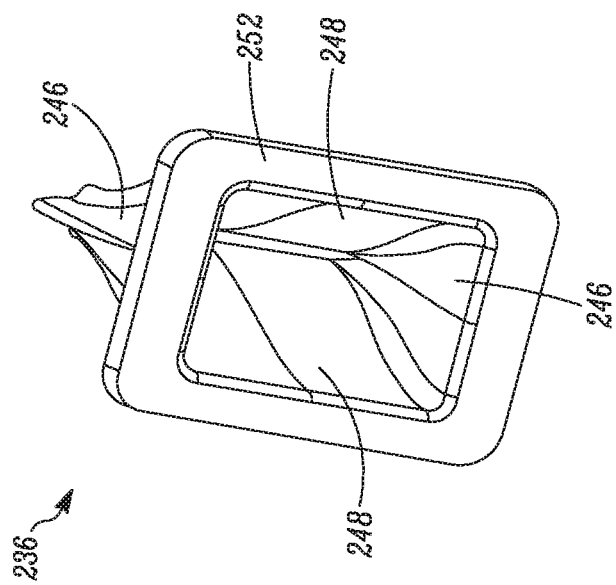
FIG. 17 is a rear perspective view of the variable nozzle of FIG. 16 shown without the flow of exhaled air therethrough.

Turning now to FIGS. 16-17, an alternative embodiment of a variable nozzle 236 is shown. The variable nozzle 236 may be used in the OPEP device 100 as an alternative to the variable nozzle 136 described above. As shown in FIGS. 16-17, the variable nozzle 236 includes an orifice 238, top and bottom walls 246, side walls 248, and a lip 252 configured to mount the variable nozzle 236 within the housing of the OPEP device 100 between the first chamber 114 and the second chamber 118 in the same manner as the variable nozzle 136. Similar to the variable nozzle 136 shown in FIGS. 12-13, the variable nozzle 236 may be constructed or molded of any material having a suitable flexibility, such as silicone.

During the administration of OPEP therapy, as the orifice 238 of the variable nozzle 236 opens in response to the flow of exhaled air therethrough, the cross-sectional shape of the orifice 238 remains generally rectangular, which results in a lower drop in pressure through the variable nozzle 236 from the first chamber 114 to the second chamber 118. The generally consistent rectangular shape of the orifice 238 of the variable nozzle 236 during increased flow rates is achieved by thin, creased walls formed in the top and bottom walls 246, which allow the side walls 248 to flex easier and with less resistance. A further advantage of this embodiment is that there is no leakage out of the top and bottom walls 246 while exhaled air flows through the orifice 238 of the variable nozzle 236, such as for example, through the V-shaped slits 150 of the variable nozzle 136 shown in FIGS. 12-13.

Those skilled in the art will also appreciate that, in some applications, only positive expiratory pressure (without oscillation) may be desired, in which case the OPEP device 100 may be operated without the restrictor member 130, but with a fixed orifice or manually adjustable orifice instead. The positive expiratory pressure embodiment may also comprise the variable nozzle 136, or the variable nozzle 236, in order to maintain a relatively consistent back pressure within a desired range.

OPEP Device—Embodiment Two

Figure 18:
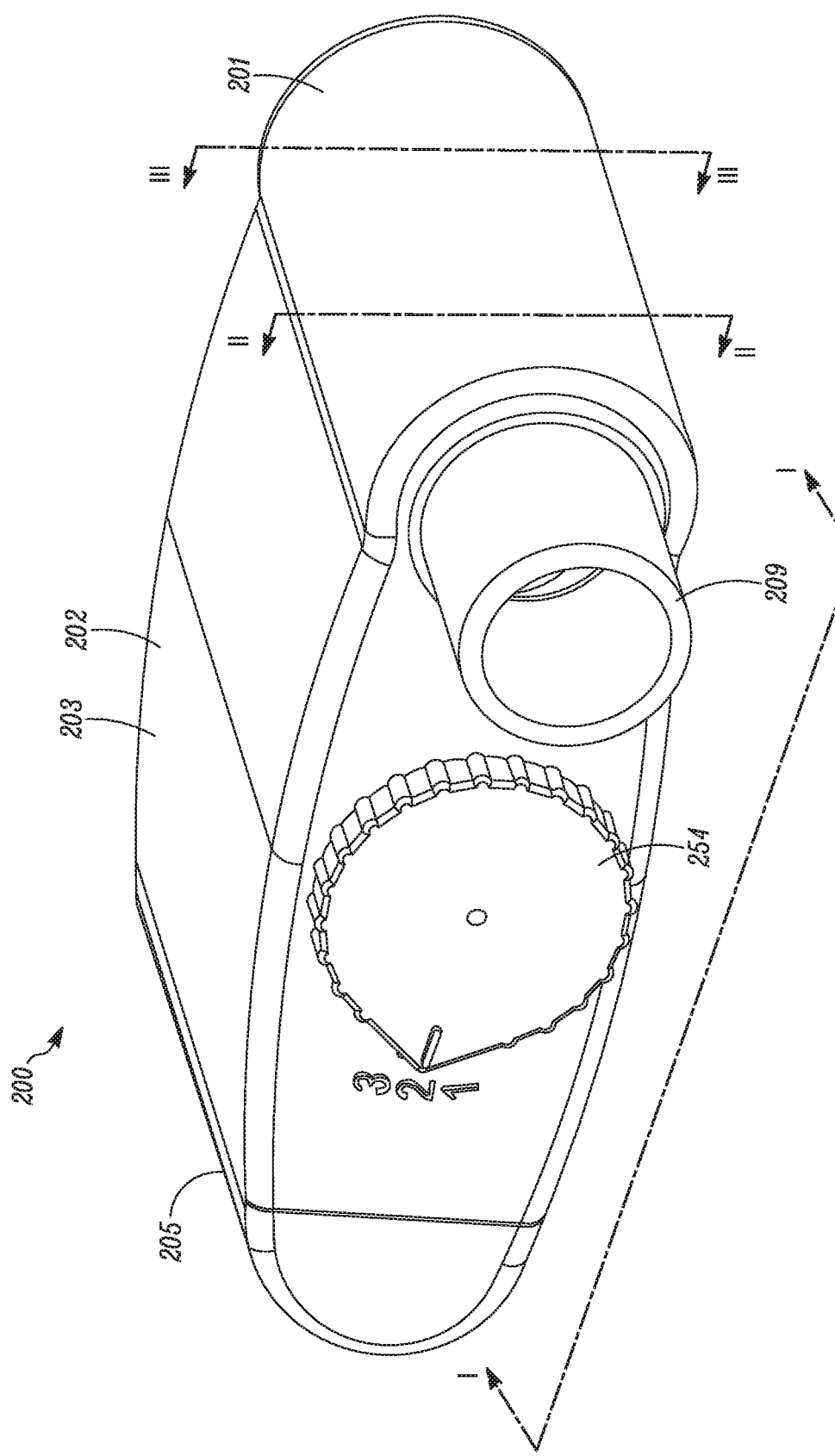
FIG. 18 is a front perspective view of a second embodiment of an OPEP device.
Figure 19:
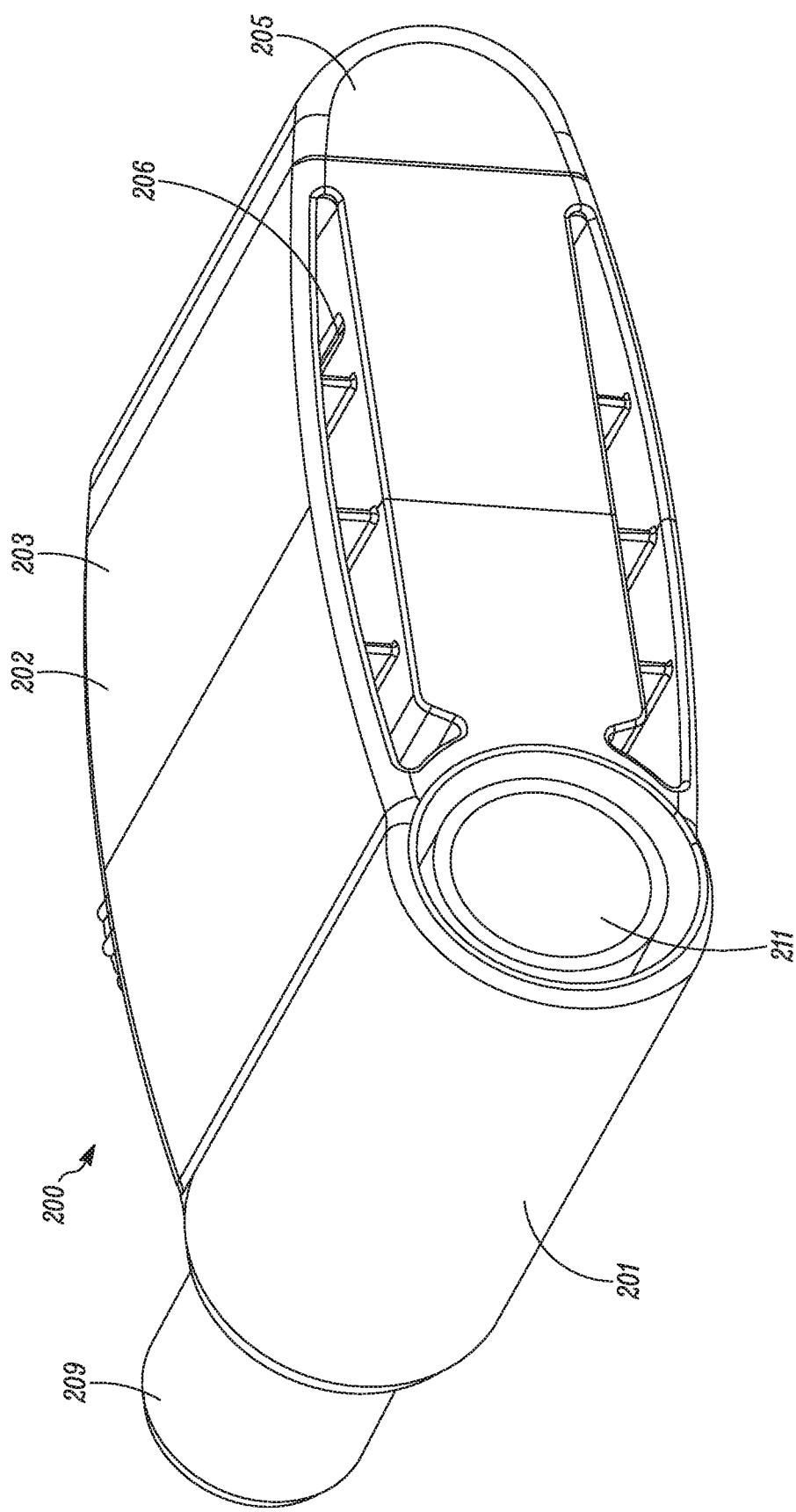
FIG. 19 is a rear perspective view of the OPEP device of FIG. 18.

Turning now to FIGS. 18-19, a front perspective view and a rear perspective view of a second embodiment of an OPEP device 200 is shown. The configuration and operation of the OPEP device 200 is similar to that of the OPEP device 100. However, as best shown in FIGS. 20-24, the OPEP device 200 further includes an adjustment mechanism 253 adapted to change the relative position of the chamber inlet 204 with respect to the housing 202 and the restrictor member 230, which in turn changes the range of rotation of the vane 232 operatively connected thereto. As explained below, a user is therefore able to conveniently adjust both the frequency and the amplitude of the OPEP therapy administered by the OPEP device 200 without opening the housing 202 and disassembling the components of the OPEP device 200.

The OPEP device 200 generally comprises a housing 202, a chamber inlet 204, a first chamber outlet 206 (best seen in FIGS. 23 and 32), a second chamber outlet 208 (best seen in FIGS. 23 and 32), and a mouthpiece 209 in fluid communication with the chamber inlet 204. As with the OPEP device 100, a front section 201, a middle section 203, and a rear section 205 of the housing 202 are separable so that the components contained therein can be periodically accessed, cleaned, replaced, or reconfigured, as required to maintain the ideal operating conditions. The OPEP device also includes an adjustment dial 254, as described below.

As discussed above in relation to the OPEP device 100, the OPEP device 200 may be adapted for use with other or additional interfaces, such as an aerosol delivery device. In this regard, the OPEP device 200 is equipped with an inhalation port 211 (best seen in FIGS. 19, 21, and 23) in fluid communication with the mouthpiece 209 and the chamber inlet 204. As noted above, the inhalation port may include a separate one-way valve (not shown) to permit a user of the OPEP device 200 both to inhale the surrounding air through the one-way valve and to exhale through the chamber inlet 204 without withdrawing the mouthpiece 209 of the OPEP device 200 between periods of inhalation and exhalation. In addition, the aforementioned aerosol delivery devices may be connected to the inhalation port 211 for the simultaneous administration of aerosol and OPEP therapies.

Figure 20:
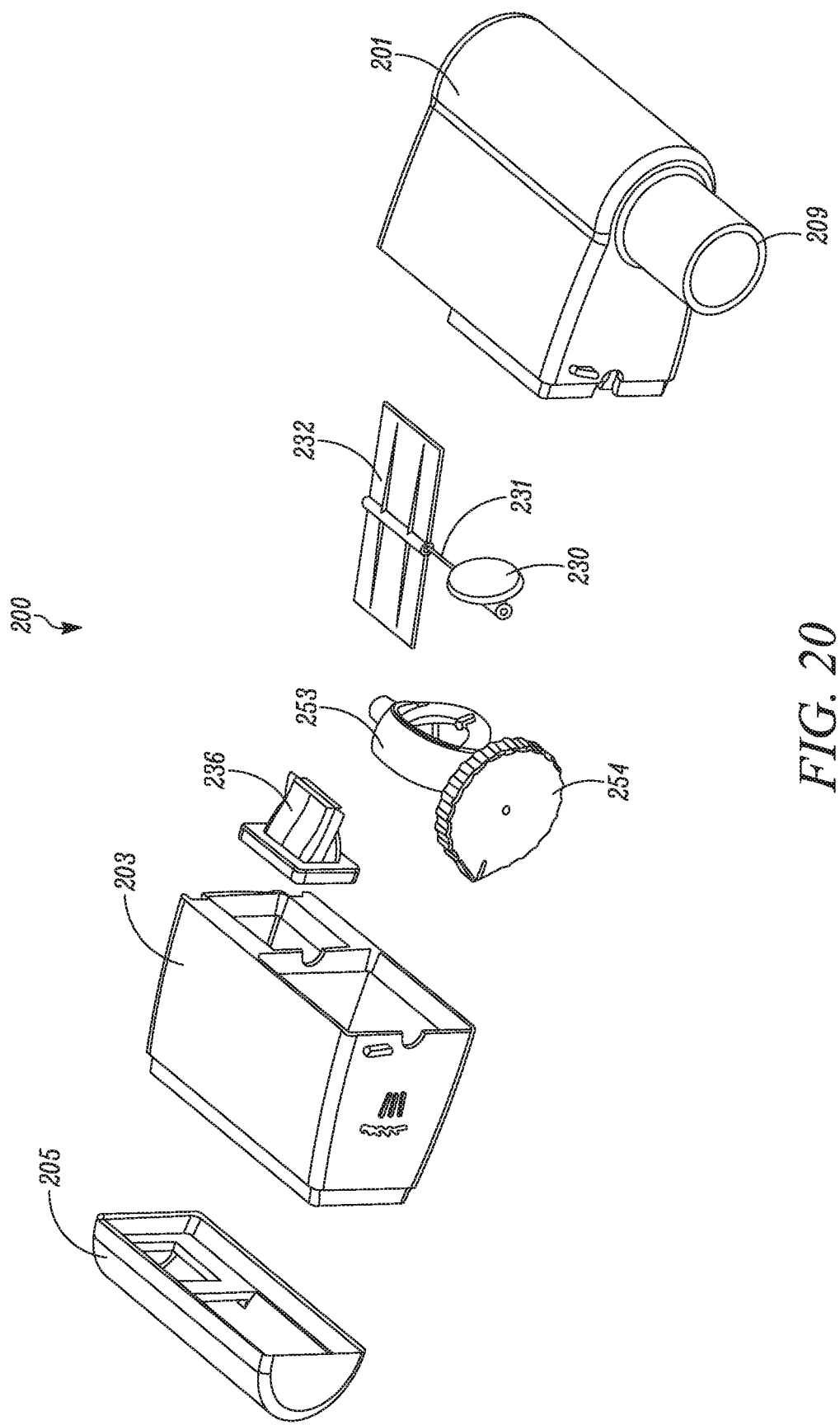
FIG. 20 is an exploded view of the OPEP device of FIG. 18, shown with the internal components of the OPEP device.

An exploded view of the OPEP device 200 is shown in FIG. 20. In addition to the components of the housing described above, the OPEP device 200 includes a restrictor member 230 operatively connected to a vane 232 by a pin 231, an adjustment mechanism 253, and a variable nozzle 236. As shown in the cross-sectional view of FIG. 21, when the OPEP device 200 is in use, the variable nozzle 236 is positioned between the middle section 203 and the rear section 205 of the housing 202, and the adjustment mechanism 253, the restrictor member 230, and the vane 232 form an assembly.

Figure 21:
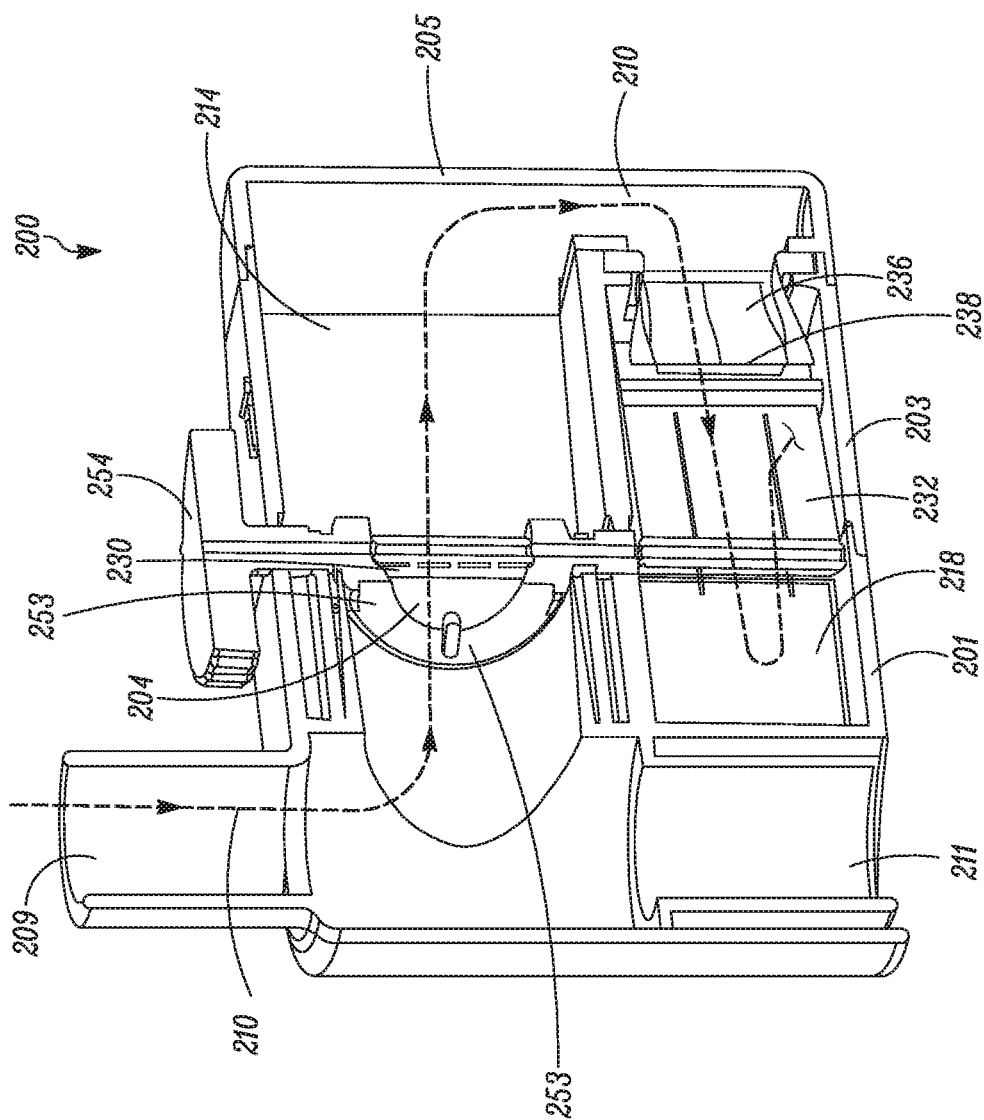
FIG. 21 is a cross-sectional view taken along line I in FIG. 18 of the OPEP device, shown with the internal components of the OPEP device.
Figure 22:
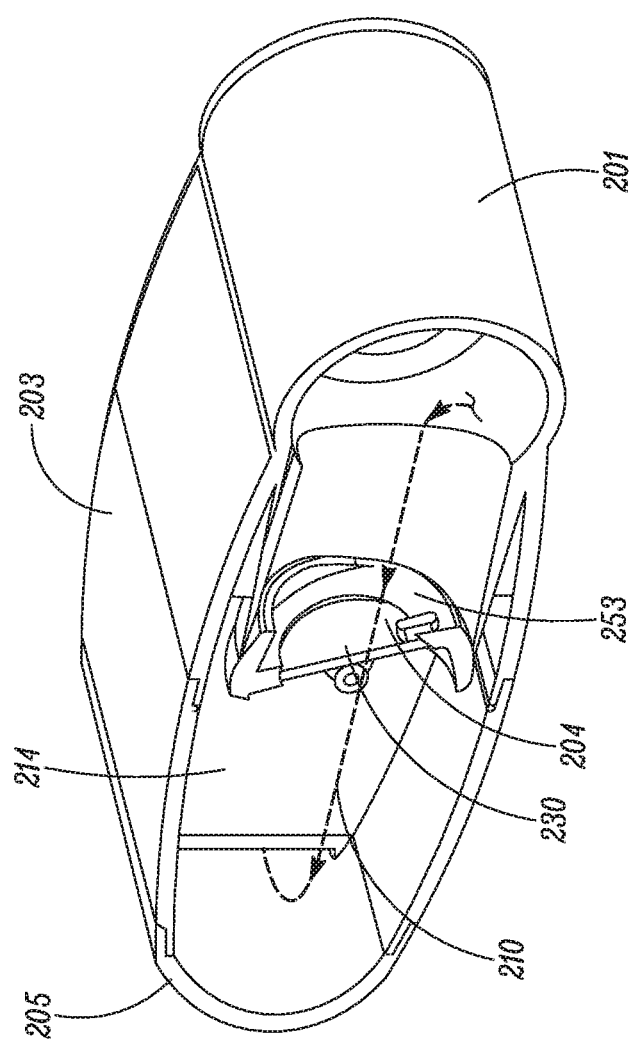
FIG. 22 is a cross-sectional view taken along line II in FIG. 18 of the OPEP device, shown with the internal components of the OPEP device.
Figure 23:
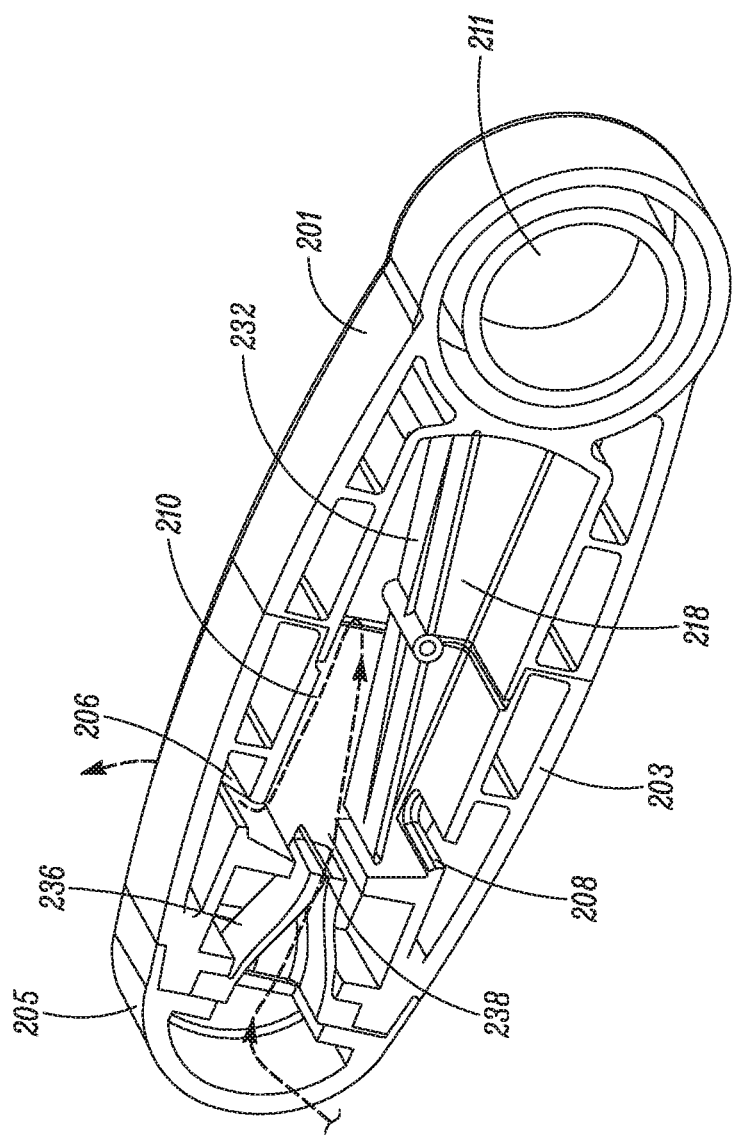
FIG. 23 is a cross-sectional view taken along line III in FIG. 18 of the OPEP device, shown with the internal components of the OPEP device.

Turning to FIGS. 21-23, various cross-sectional perspective views of the OPEP device 200 are shown. As with the OPEP device 100, an exhalation flow path 210, identified by a dashed line, is defined between the mouthpiece 209 and at least one of the first chamber outlet 206 and the second chamber outlet 208 (best seen in FIGS. 23 and 32). As a result of a one-way valve (not-shown) and/or an aerosol delivery device (not shown) attached to the inhalation port 211, the exhalation flow path 210 begins at the mouthpiece 209 and is directed toward the chamber inlet 204, which in operation may or may not be blocked by the restrictor member 230. After passing through the chamber inlet 204, the exhalation flow path 210 enters a first chamber 214 and makes a 180° turn toward the variable nozzle 236. After passing through the orifice 238 of the variable nozzle 236, the exhalation flow path 210 enters a second chamber 218. In the second chamber 218, the exhalation flow path 210 may exit the OPEP device 200 through at least one of the first chamber outlet 206 or the second chamber outlet 208. Those skilled in the art will appreciate that the exhalation flow path 210 identified by the dashed line is exemplary, and that air exhaled into the OPEP device 200 may flow in any number of directions or paths as it traverses from the mouthpiece 209 or chamber inlet 204 to the first chamber outlet 206 or the second chamber outlet 208.

Figure 25:
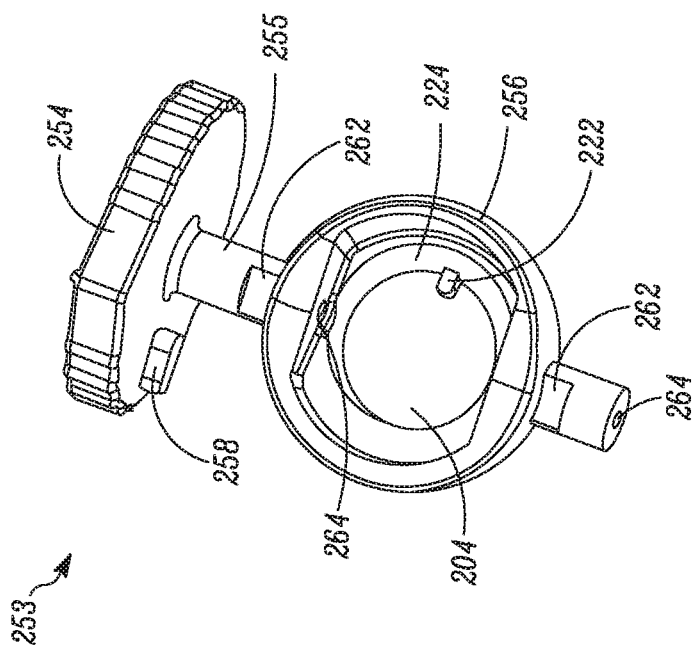
FIG. 25 is a rear perspective view of the adjustment mechanism of FIG. 24.
Figure 24:
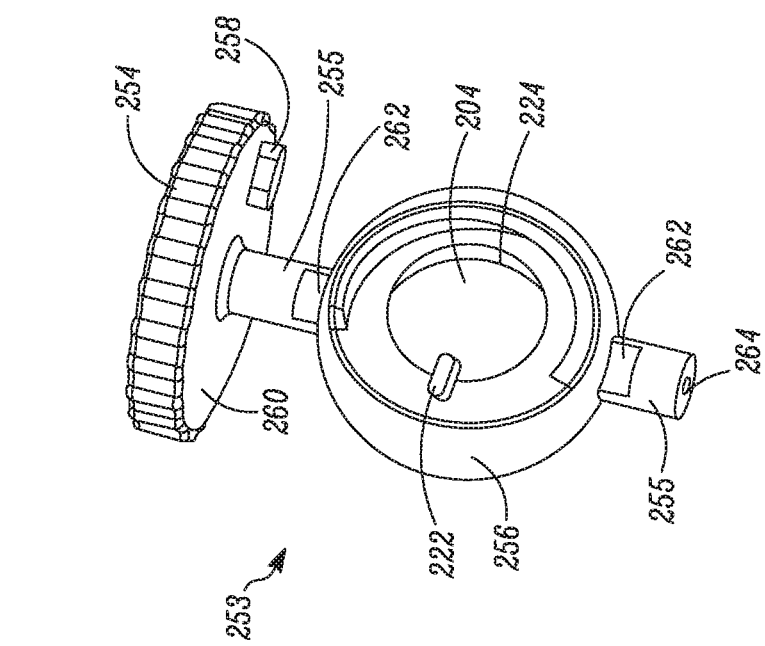
FIG. 24 is a front perspective view of an adjustment mechanism of the OPEP device of FIG. 18.

Referring to FIGS. 24-25, front and rear perspective views of the adjustment mechanism 253 of the OPEP device 200 are shown. In general, the adjustment mechanism 253 includes an adjustment dial 254, a shaft 255, and a frame 256. A protrusion 258 is positioned on a rear face 260 of the adjustment dial, and is adapted to limit the selective rotation of the adjustment mechanism 253 by a user, as further described below. The shaft 255 includes keyed portions 262 adapted to fit within upper and lower bearings 226, 228 formed in the housing 200 (see FIGS. 21 and 28-29). The shaft further includes an axial bore 264 configured to receive the pin 231 operatively connecting the restrictor member 230 and the vane 232. As shown, the frame 256 is spherical, and as explained below, is configured to rotate relative to the housing 202, while forming a seal between the housing 202 and the frame 256 sufficient to permit the administration of OPEP therapy. The frame 256 includes a circular opening defined by a seat 224 adapted to accommodate the restrictor member 230. In use, the circular opening functions as the chamber inlet 204. The frame 256 also includes a stop 222 for preventing the restrictor member 230 from opening in a wrong direction.

Figure 26:
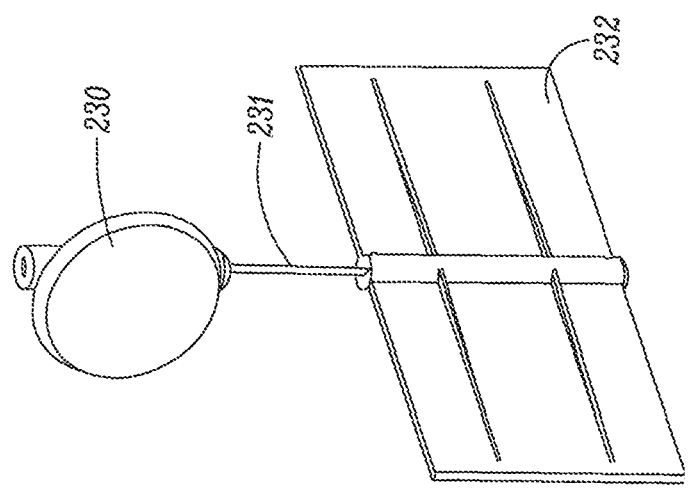
FIG. 26 is a front perspective view of a restrictor member operatively connected to a vane for use in the OPEP device of FIG. 18.

Turning to FIG. 26, a front perspective view of the restrictor member 230 and the vane 232 is shown. The design, materials, and configuration of the restrictor member 230 and the vane 232 may be the same as described above in regards to the OPEP device 100. However, the restrictor member 230 and the vane 232 in the OPEP device 200 are operatively connected by a pin 231 adapted for insertion through the axial bore 264 in the shaft 255 of the adjustment mechanism 253. The pin 231 may be constructed, for example, by stainless steel. In this way, rotation of the restrictor member 230 results in a corresponding rotation of the vane 232, and vice versa.

Figure 27:
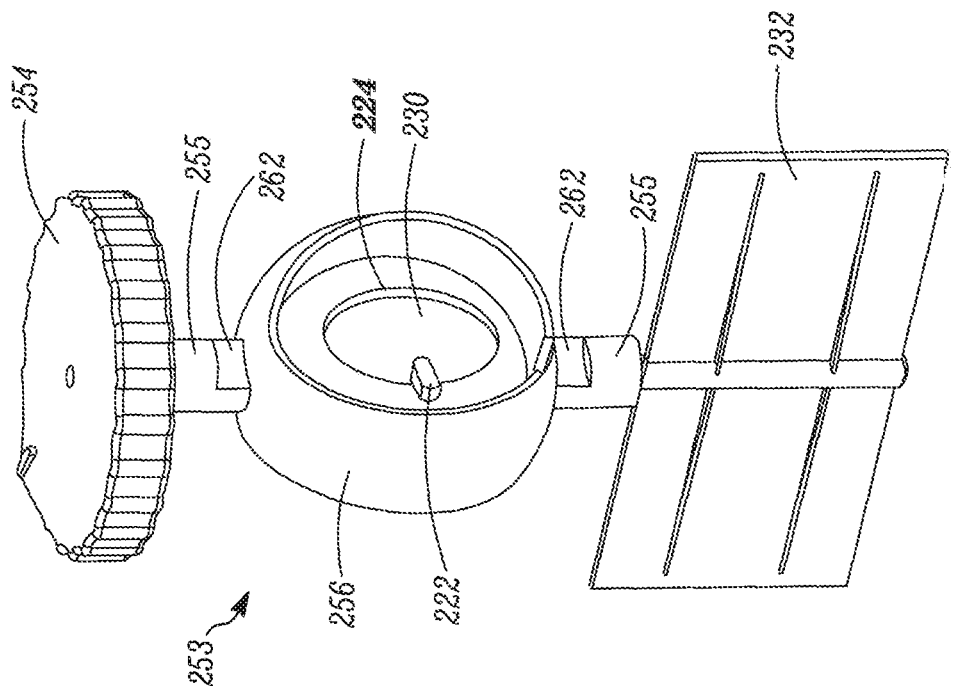
FIG. 27 is a front perspective view of the adjustment mechanism of FIG. 24 assembled with the restrictor member and the vane of FIG. 26.

Turning to FIG. 27, a front perspective view of the adjustment mechanism 253 assembled with the restrictor member 230 and the vane 232 is shown. In this configuration, it can be seen that the restrictor member 230 is positioned such that it is rotatable relative to the frame 256 and the seat 224 between a closed position (as shown), where a flow of exhaled air along the exhalation flow path 210 through the chamber inlet 204 is restricted, and an open position (not shown), where the flow of exhaled air through the chamber inlet 204 is less restricted. As previously mentioned the vane 232 is operatively connected to the restrictor member 230 by the pin 231 extending through shaft 255, and is adapted to move in unison with the restrictor member 230. It can further be seen that the restrictor member 230 and the vane 232 are supported by the adjustment mechanism 253, which itself is rotatable within the housing 202 of the OPEP device 200, as explained below.

Figure 28:
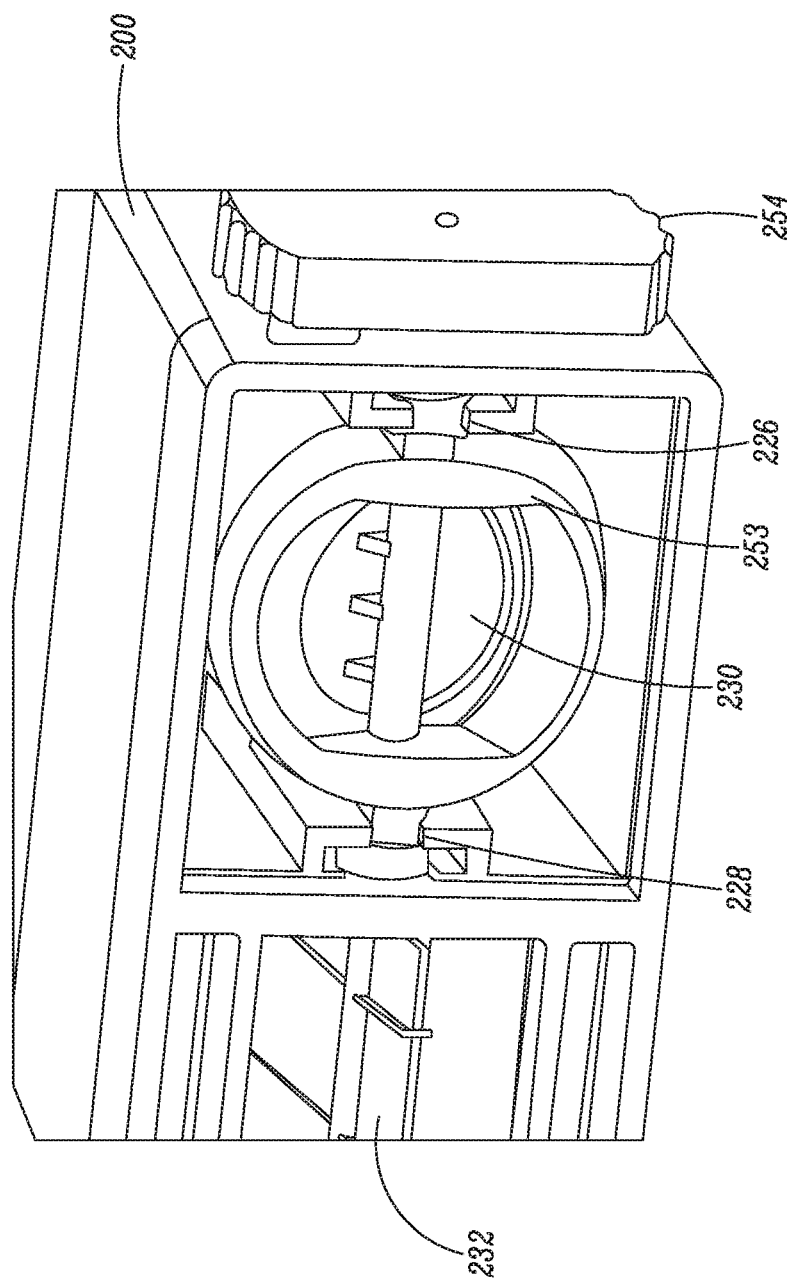
FIG. 28 is a partial cross-sectional view of the assembly of FIG. 27 within the OPEP device of FIG. 18.
Figure 29B:
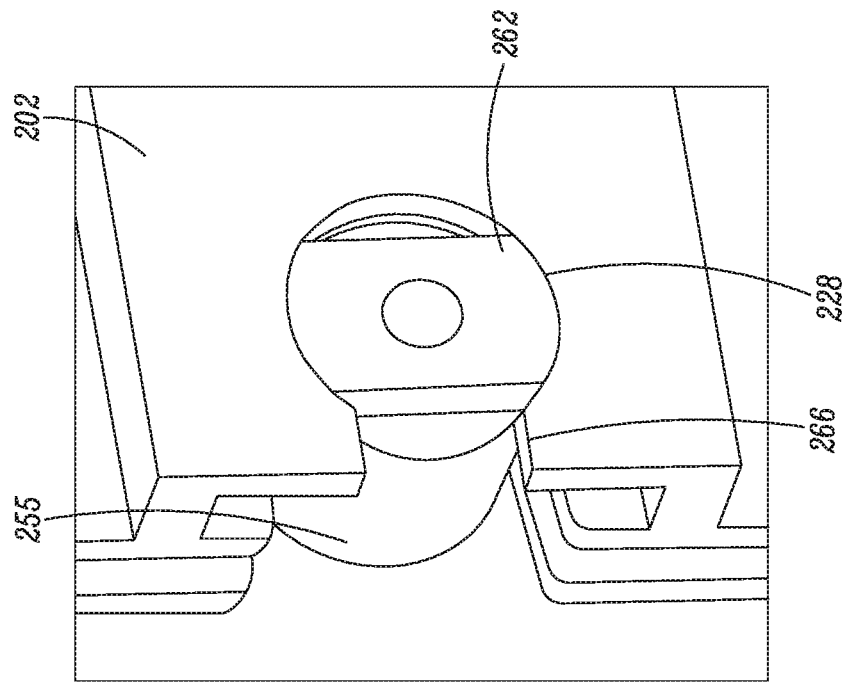
FIGS. 29A-B are partial cross-sectional views illustrating installation of the assembly of FIG. 27 within the OPEP device of FIG. 18.
Figure 29A:
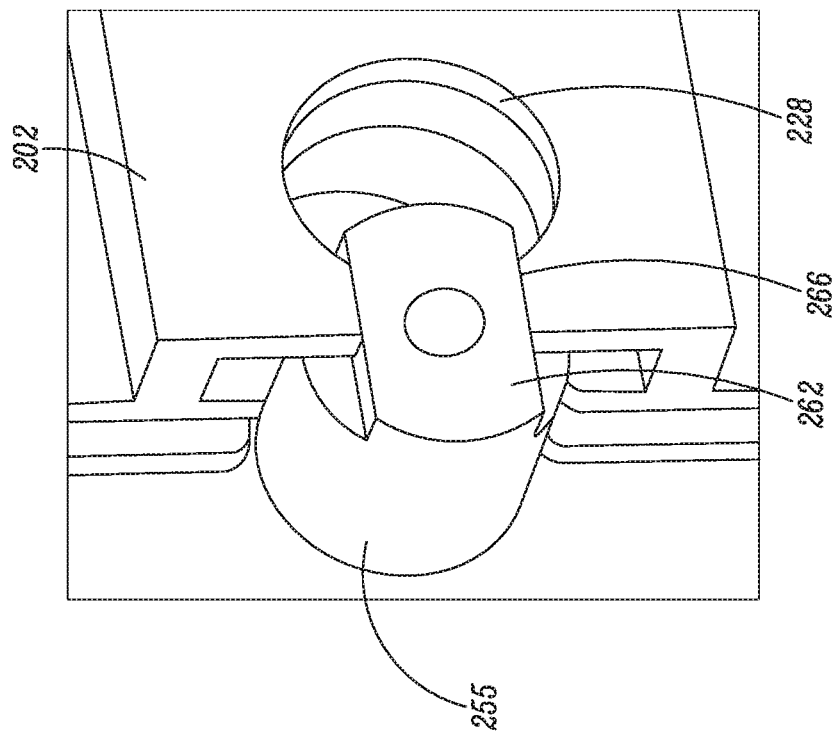

FIGS. 28 and 29A-B are partial cross-sectional views illustrating the adjustment mechanism 253 mounted within the housing 202 of the OPEP device 200. As shown in FIG. 28, the adjustment mechanism 253, as well as the restrictor member 230 and the vane 232, are rotatably mounted within the housing 200 about an upper and lower bearing 226, 228, such that a user is able to rotate the adjustment mechanism 253 using the adjustment dial 254. FIGS. 29A-29B further illustrates the process of mounting and locking the adjustment mechanism 253 within the lower bearing 228 of the housing 202. More specifically, the keyed portion 262 of the shaft 255 is aligned with and inserted through a rotational lock 166 formed in the housing 202, as shown in FIG. 29A. Once the keyed portion 262 of the shaft 255 is inserted through the rotational lock 266, the shaft 255 is rotated 90° to a locked position, but remains free to rotate. The adjustment mechanism 253 is mounted and locked within the upper bearing 226 in the same manner.

Figure 30:
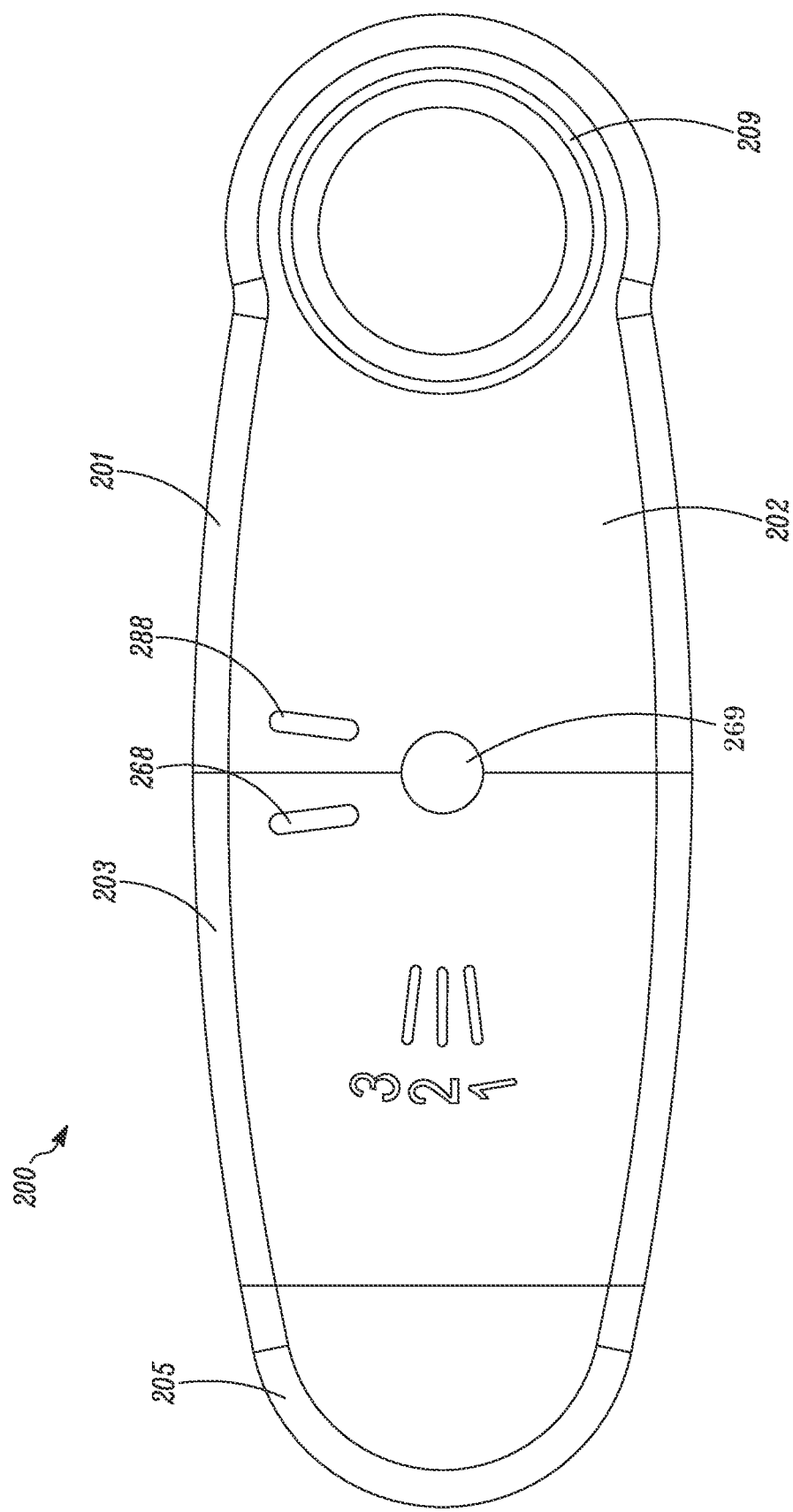
FIG. 30 is a front view of the OPEP device of FIG. 18 illustrating an aspect of the adjustability of the OPEP device.

Once the housing 200 and the internal components of the OPEP device 200 are assembled, the rotation of the shaft 255 is restricted to keep it within a locked position in the rotational lock 166. As shown in a front view of the OPEP device 200 in FIG. 30, two stops 268, 288 are positioned on the housing 202 such that they engage the protrusion 258 formed on the rear face 260 of the adjustment dial 254 when a user rotates the adjustment dial 254 to a predetermined position. For purposes of illustration, the OPEP device 200 is shown in FIG. 30 without the adjustment dial 254 or the adjustment mechanism 253, which would extend from the housing 202 through an opening 269. In this way, rotation of the adjustment dial 254, the adjustment mechanism 253, and the keyed portion 262 of the shaft 255 can be appropriately restricted.

Figure 31:
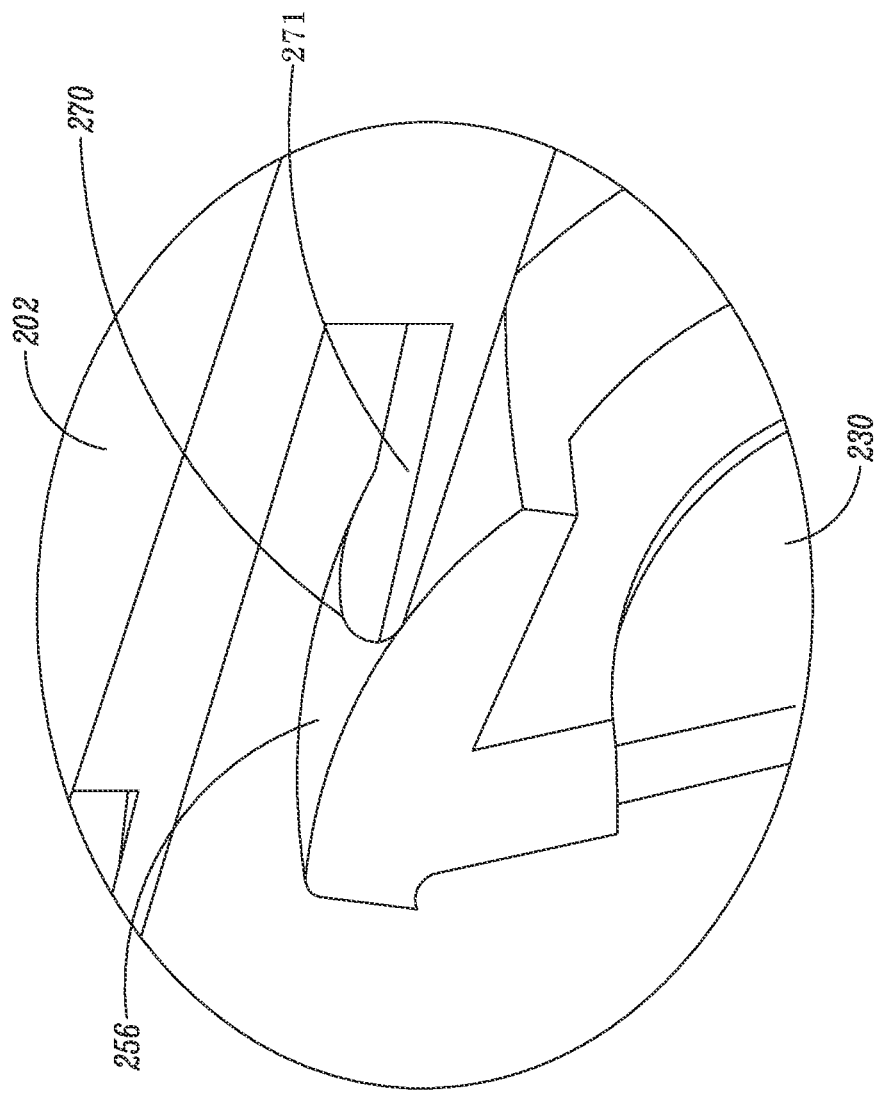
FIG. 31 is a partial cross-sectional view of the assembly of FIG. 27 within the OPEP device of FIG. 18.

Turning to FIG. 31, a partial cross-sectional view of the adjustment mechanism 253 mounted within the housing 200 is shown. As previously mentioned, the frame 256 of the adjustment mechanism 253 is spherical, and is configured to rotate relative to the housing 202, while forming a seal between the housing 202 and the frame 256 sufficient to permit the administration of OPEP therapy. As shown in FIG. 31, a flexible cylinder 271 extending from the housing 202 completely surrounds a portion of the frame 256 to form a sealing edge 270. Like the housing 202 and the restrictor member 230, the flexible cylinder 271 and the frame 256 may be constructed of a low shrink, low friction plastic. One such material is acetal. In this way, the sealing edge 270 contacts the frame 256 for a full 360° and forms a seal throughout the permissible rotation of the adjustment member 253.

Figure 33B:
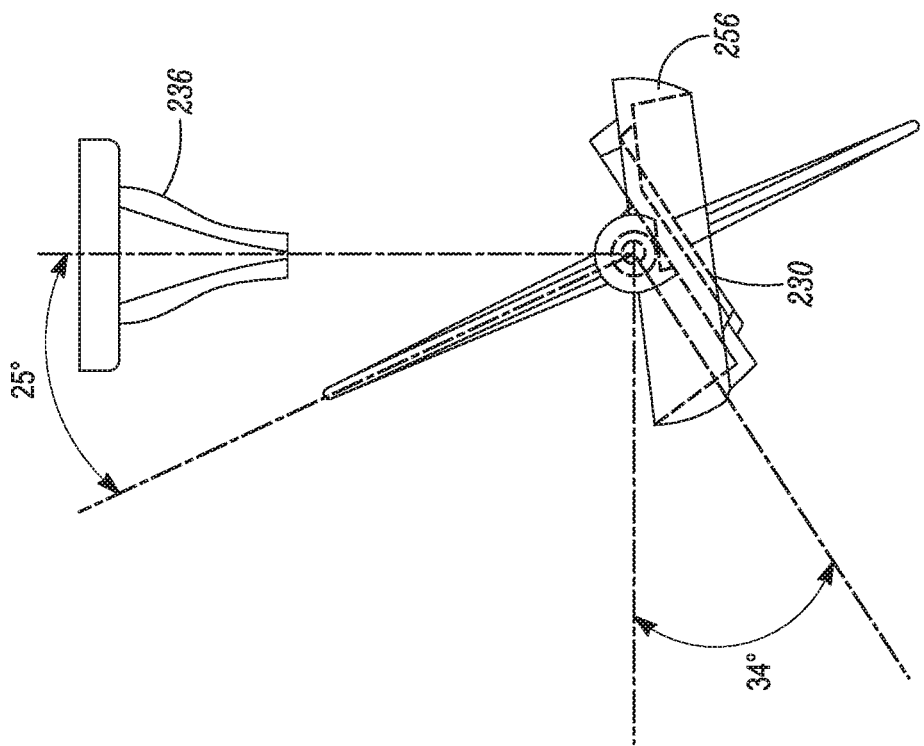
FIGS. 33A-B are top phantom views illustrating the adjustability of the OPEP device of FIG. 18.
Figure 33A:
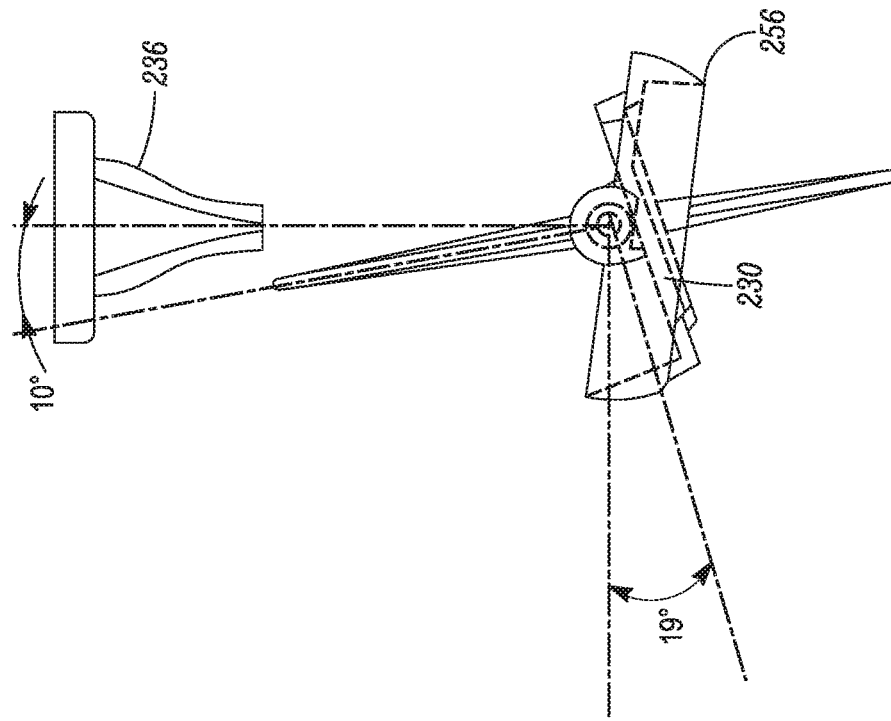

The selective adjustment of the OPEP device 200 will now be described with reference to FIGS. 32A-B, 33A-B, and 34A-B. FIGS. 32A-B are partial cross-sectional views of the OPEP device 200; FIGS. 33A-B are illustrations of the adjustability of the OPEP device 200; and, FIGS. 34A-B are top phantom views of the OPEP device 200. As previously mentioned with regards to the OPEP device 100, it is preferable that the vane 232 and the restrictor member 230 are configured such that when the OPEP device 200 is fully assembled, the angle between a centerline of the variable nozzle 236 and the vane 232 is between 10° and 25° when the restrictor member 230 is in a closed position. However, it should be appreciated that the adjustability of the OPEP device 200 is not limited to the parameters described herein, and that any number of configurations may be selected for purposes of administering OPEP therapy within the ideal operating conditions.

FIG. 32A shows the vane 232 at an angle of 10° from the centerline of the variable nozzle 236, whereas FIG. 32B shows the vane 232 at an angle of 25° from the centerline of the variable nozzle 236. FIG. 33A illustrates the necessary position of the frame 256 (shown in phantom) relative to the variable nozzle 236 such that the angle between a centerline of the variable nozzle 236 and the vane 232 is 10° when the restrictor member 230 is in the closed position. FIG. 33B, on the other hand, illustrates the necessary position of the frame 256 (shown in phantom) relative to the variable nozzle 236 such that the angle between a centerline of the variable nozzle 236 and the vane 232 is 25° when the restrictor member 230 is in the closed position.

Referring to FIGS. 34A-B, side phantom views of the OPEP device 200 are shown. The configuration shown in FIG. 34A corresponds to the illustrations shown in FIGS. 32A and 33A, wherein the angle between a centerline of the variable nozzle 236 and the vane 232 is 10° when the restrictor member 230 is in the closed position. FIG. 34B, on the other hand, corresponds to the illustrations shown in FIGS. 32B and 33B, wherein the angle between a centerline of the variable nozzle 236 and the vane 232 is 25° when the restrictor member 230 is in the closed position. In other words, the frame 256 of the adjustment member 253 has been rotated counter-clockwise 15°, from the position shown in FIG. 34A, to the position shown in FIG. 34B, thereby also increasing the permissible rotation of the vane 232.

In this way, a user is able to rotate the adjustment dial 254 to selectively adjust the orientation of the chamber inlet 204 relative to the restrictor member 230 and the housing 202. For example, a user may increase the frequency and amplitude of the OPEP therapy administered by the OPEP device 200 by rotating the adjustment dial 254, and therefore the frame 256, toward the position shown in FIG. 34A. Alternatively, a user may decrease the frequency and amplitude of the OPEP therapy administered by the OPEP device 200 by rotating the adjustment dial 254, and therefore the frame 256, toward the position shown in FIG. 34B. Furthermore, as shown for example in FIGS. 18 and 30, indicia may be provided to aid the user in the setting of the appropriate configuration of the OPEP device 200.

Operating conditions similar to those described below with reference to the OPEP device 800 may also be achievable for an OPEP device according to the OPEP device 200.

OPEP Device—Embodiment Three

Figure 35:
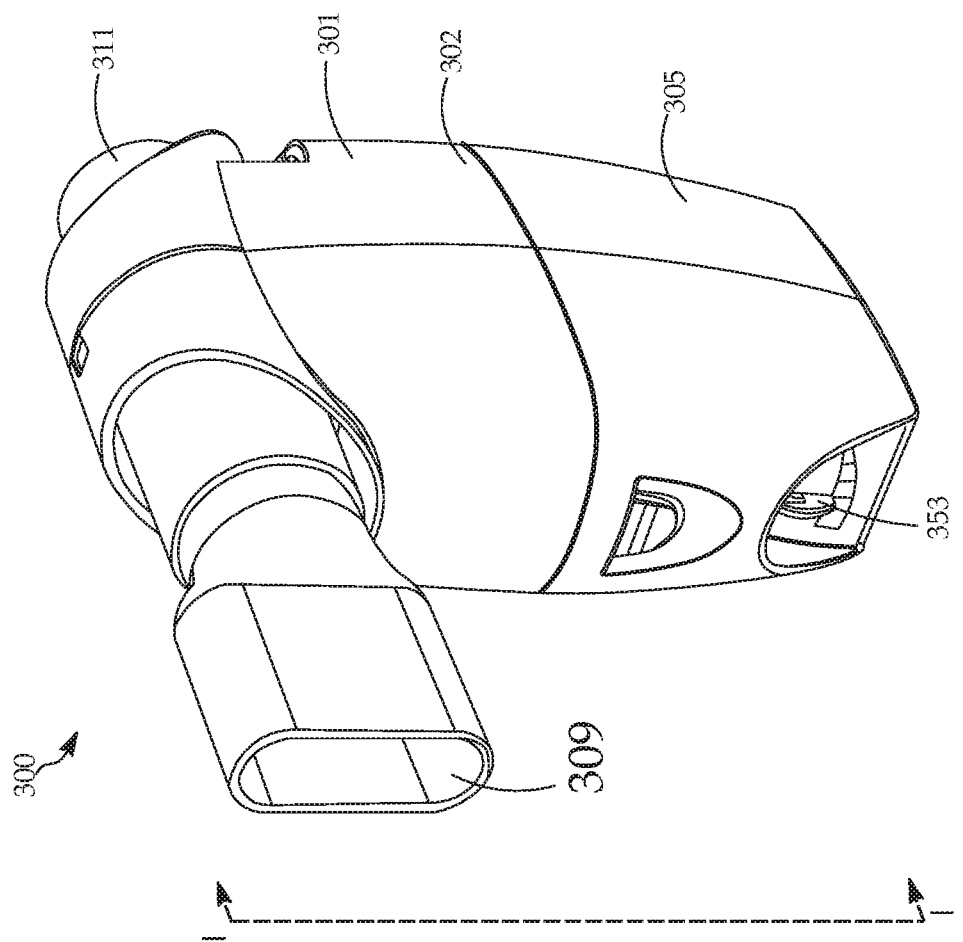
FIG. 35 is a front perspective view of another embodiment of an OPEP device.
Figure 36:
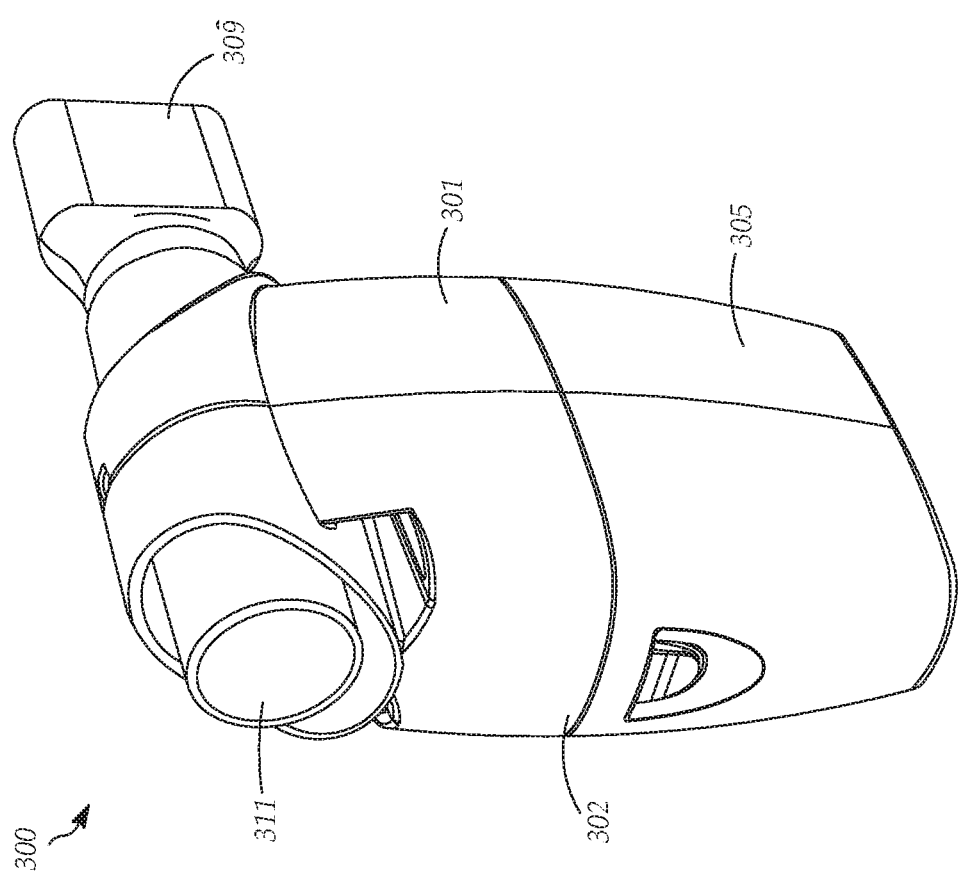
FIG. 36 is a rear perspective view of the OPEP device of FIG. 35.
Figure 37:
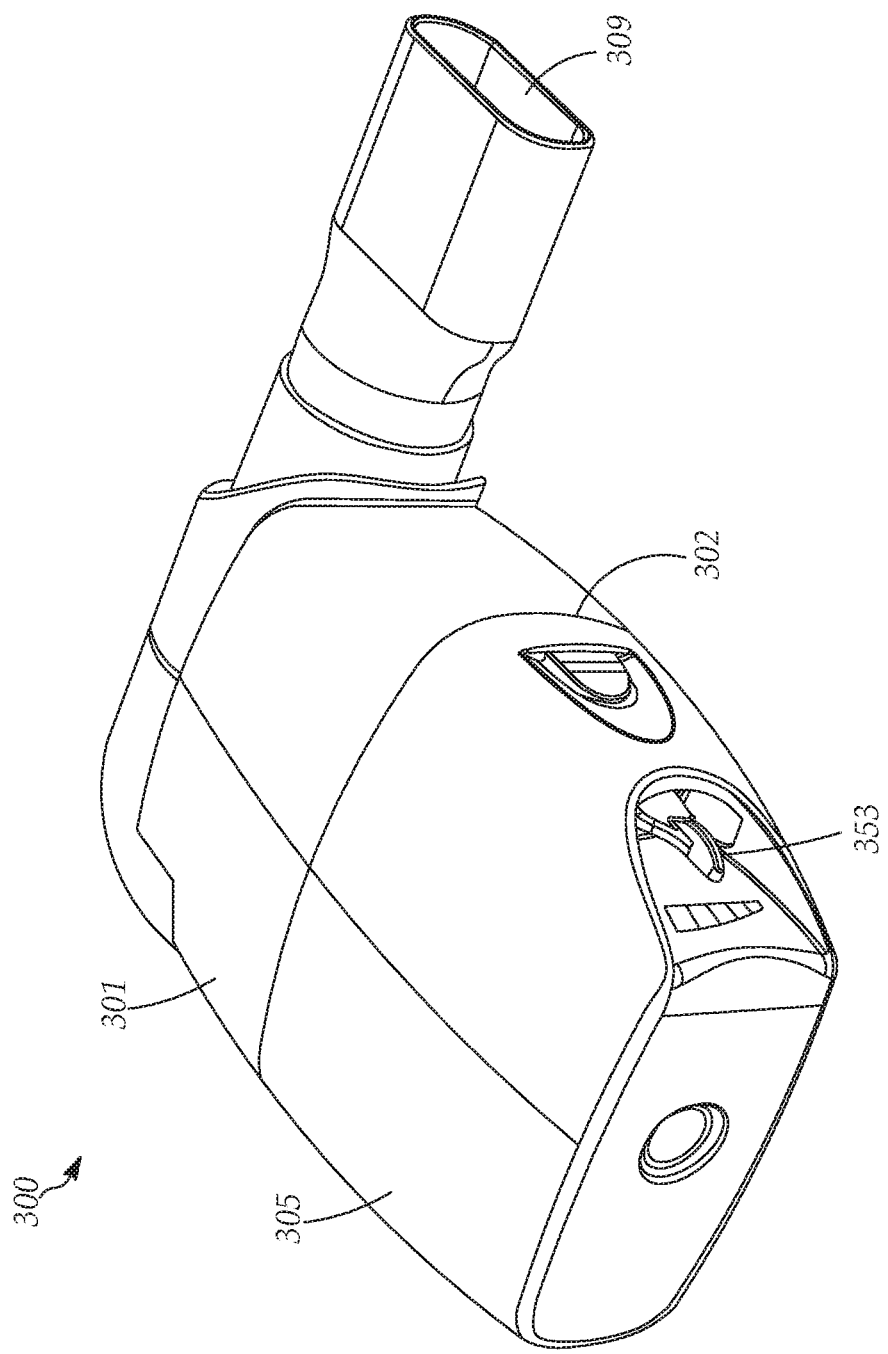
FIG. 37 is a perspective view of the bottom of the OPEP device of FIG. 35.

Turning to FIGS. 35-37, another embodiment of an OPEP device 300 is shown. The OPEP device 300 is similar to that of the OPEP device 200 in that is selectively adjustable. As best seen in FIGS. 35, 37, 40, and 49, the OPEP device 300, like the OPEP device 300, includes an adjustment mechanism 353 adapted to change the relative position of a chamber inlet 304 with respect to a housing 302 and a restrictor member 330, which in turn changes the range of rotation of a vane 332 operatively connected thereto. As previously explained with regards to the OPEP device 200, a user is therefore able to conveniently adjust both the frequency and the amplitude of the OPEP therapy administered by the OPEP device 300 without opening the housing 302 and disassembling the components of the OPEP device 300. The administration of OPEP therapy using the OPEP device 300 is otherwise the same as described above with regards to the OPEP device 100.

The OPEP device 300 comprises a housing 302 having a front section 301, a rear section 305, and an inner casing 303. As with the previously described OPEP devices, the front section 301, the rear section 305, and the inner casing 303 are separable so that the components contained therein can be periodically accessed, cleaned, replaced, or reconfigured, as required to maintain the ideal operating conditions. For example, as shown in FIGS. 35-37, the front section 301 and the rear section 305 of the housing 302 are removably connected via a snap fit engagement.

Figure 38:
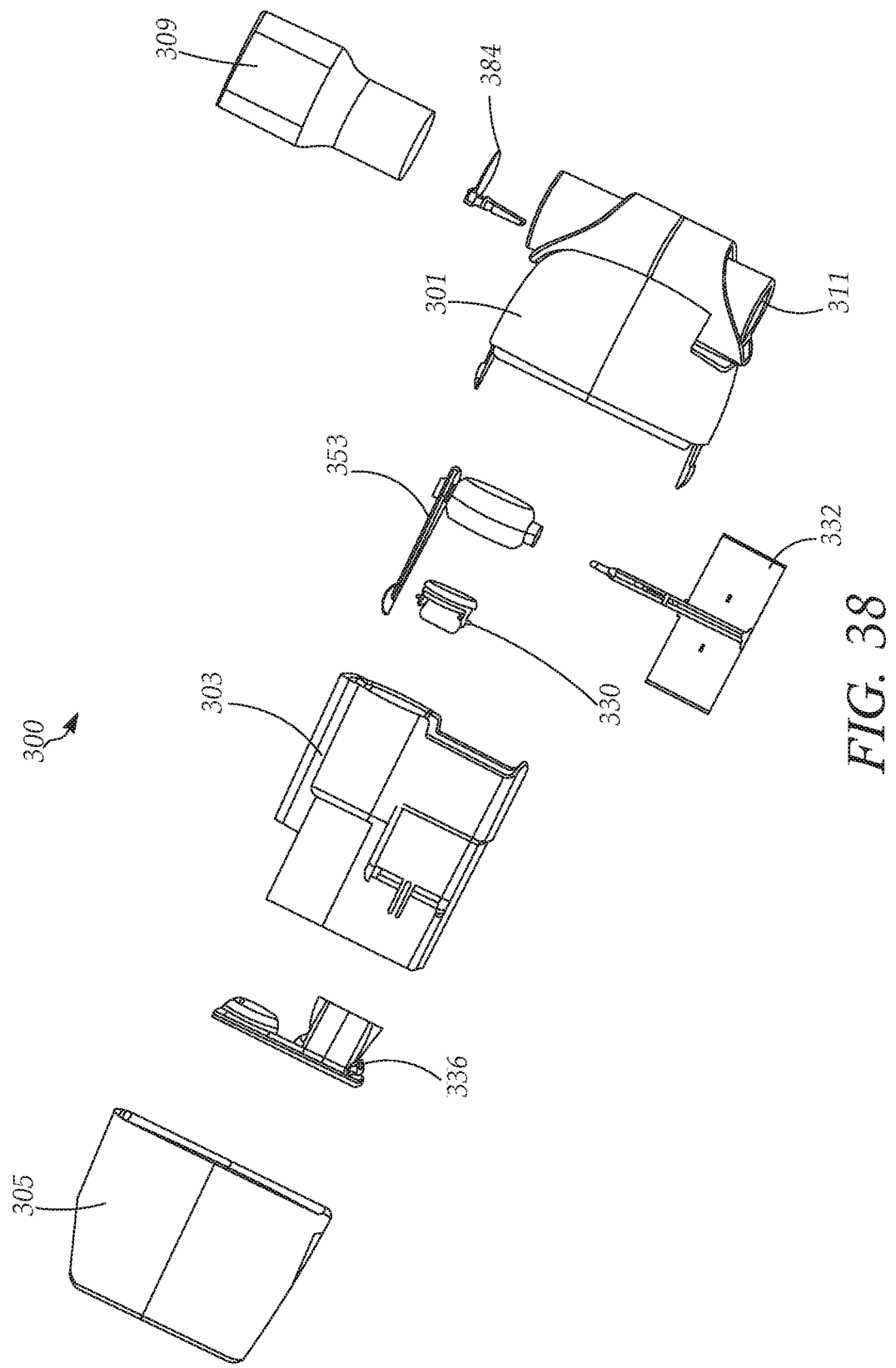
FIG. 38 is an exploded view of the OPEP device of FIG. 35.

The components of the OPEP device 300 are further illustrated in the exploded view of FIG. 38. In general, in addition to the front section 301, the rear section 305, and the inner casing 303, the OPEP device 300 further comprises a mouthpiece 309, an inhalation port 311, a one-way valve 384 disposed therebetween, an adjustment mechanism 353, a restrictor member 330, a vane 332, and a variable nozzle 336.

Figure 39:
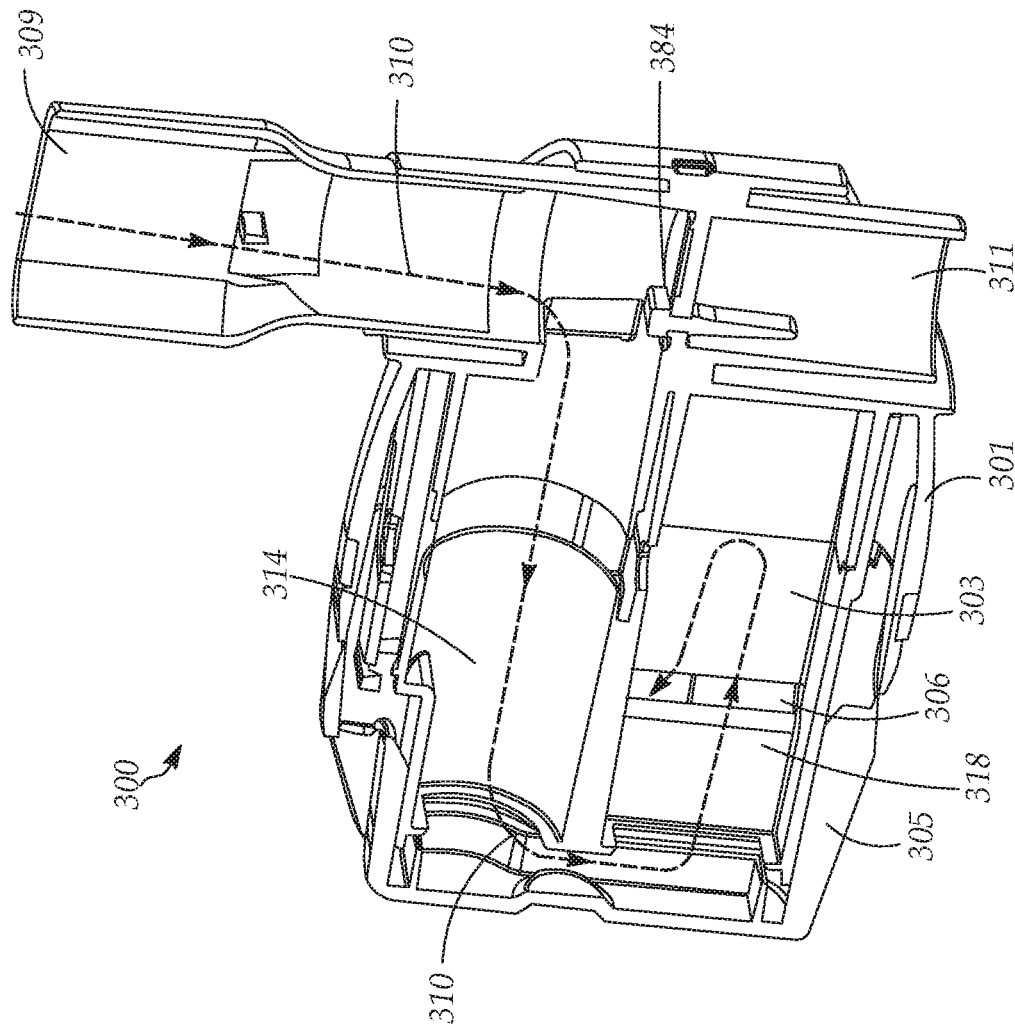
FIG. 39 is a cross-sectional view taken along line I in FIG. 35, shown without the internal components of the OPEP device.
Figure 40:
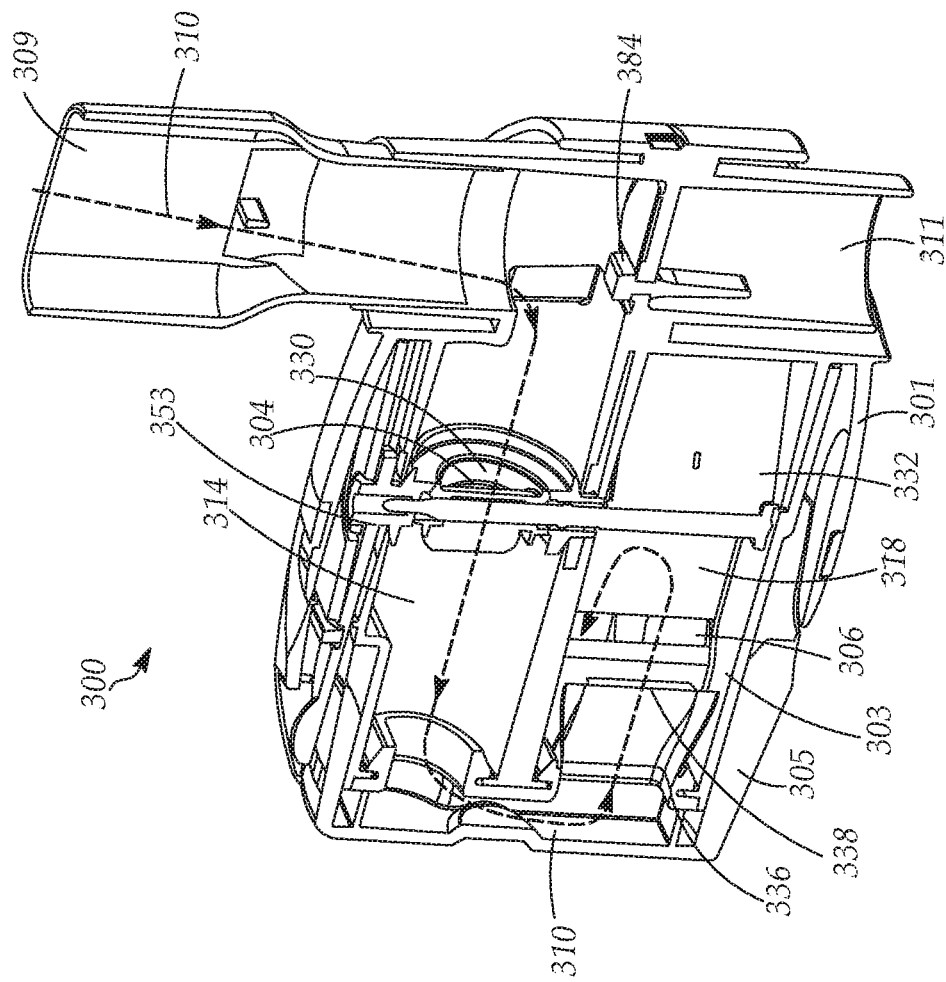
FIG. 40 is a cross-sectional view taken along line I in FIG. 35, shown with the internal components of the OPEP device.
Figure 41:
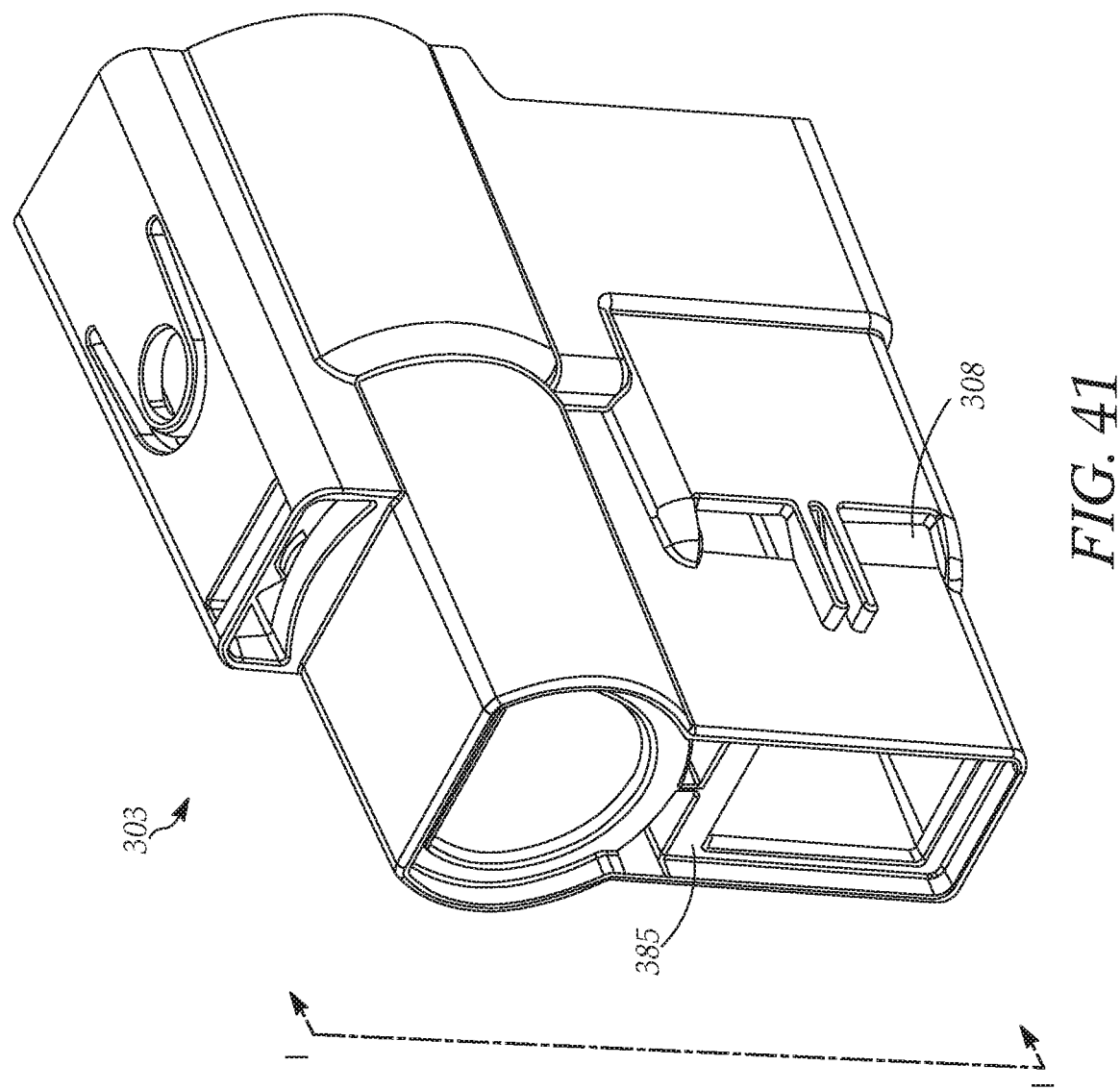
FIG. 41 is a front-perspective view of an inner casing of the OPEP device of FIG. 35.
Figure 42:
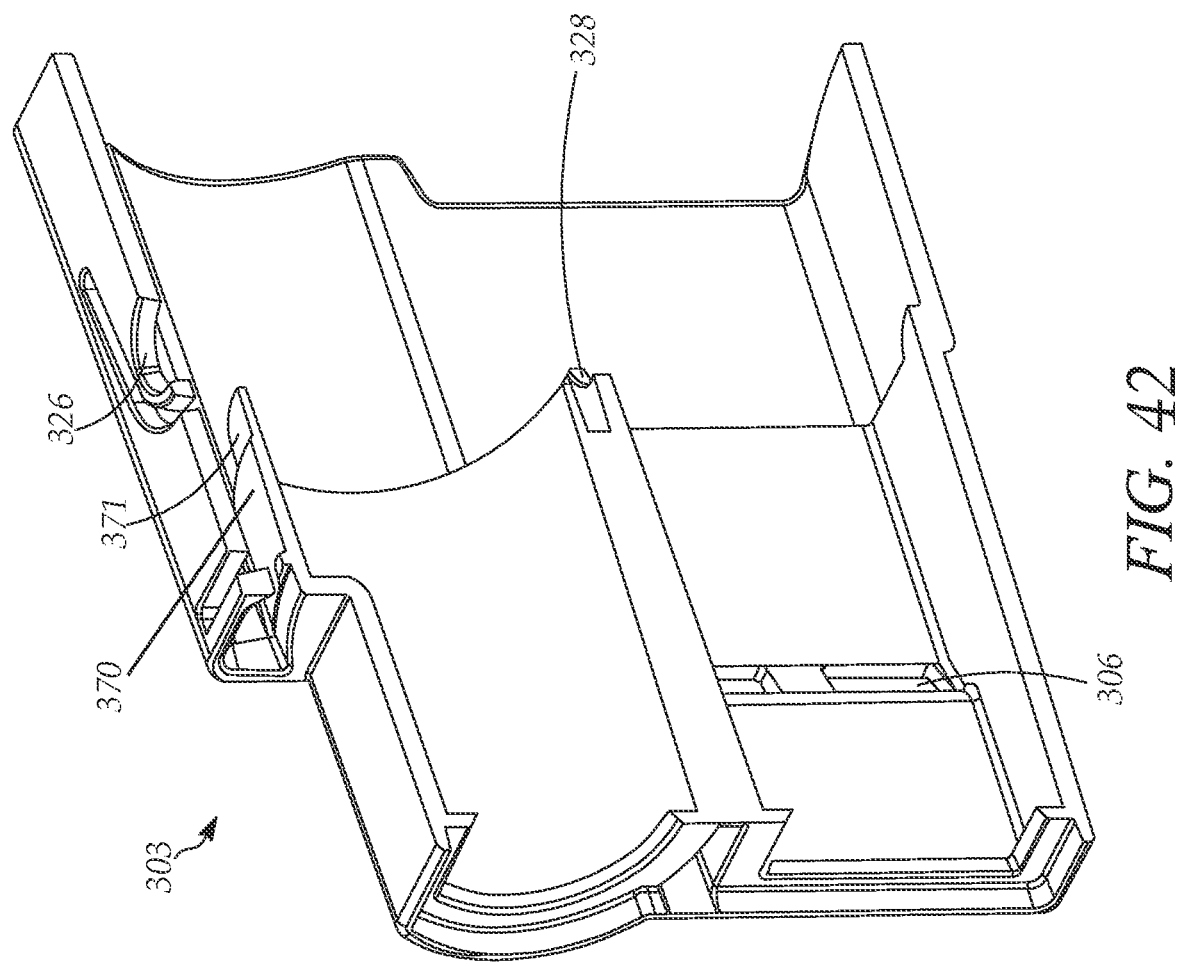
FIG. 42 is a cross-sectional view of the inner casing taken along line I of in FIG. 41.

As seen in FIGS. 39-40, the inner casing 303 is configured to fit within the housing 302 between the front section 301 and the rear section 305, and partially defines a first chamber 314 and a second chamber 318. The inner casing 303 is shown in further detail in the perspective and cross sectional views shown in FIGS. 41-42. A first chamber outlet 306 and a second chamber outlet 308 are formed within the inner casing 303. One end 385 of the inner casing 303 is adapted to receive the variable nozzle 336 and maintain the variable nozzle 336 between the rear section 305 and the inner casing 303. An upper bearing 326 and a lower bearing 328 for supporting the adjustment mechanism 353 is formed, at least in part, within the inner casing 303. Like the flexible cylinder 271 and sealing edge 270 described above with regards to the OPEP device 200, the inner casing 303 also includes a flexible cylinder 371 with a sealing edge 370 for engagement about a frame 356 of the adjustment mechanism 353.

The vane 332 is shown in further detail in the perspective view shown in FIG. 43. A shaft 334 extends from the vane 332 and is keyed to engage a corresponding keyed portion within a bore 365 of the restrictor member 330. In this way, the shaft 334 operatively connects the vane 332 with the restrictor member 330 such that the vane 332 and the restrictor member 330 rotate in unison.

Figure 46:
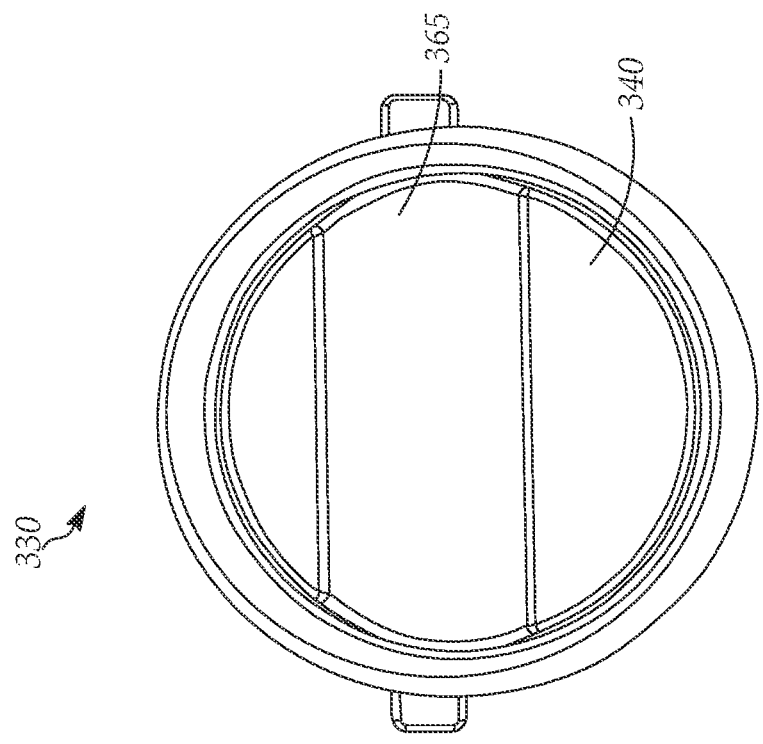
FIG. 46 is a front view of the restrictor member of FIG. 44.
Figure 45:
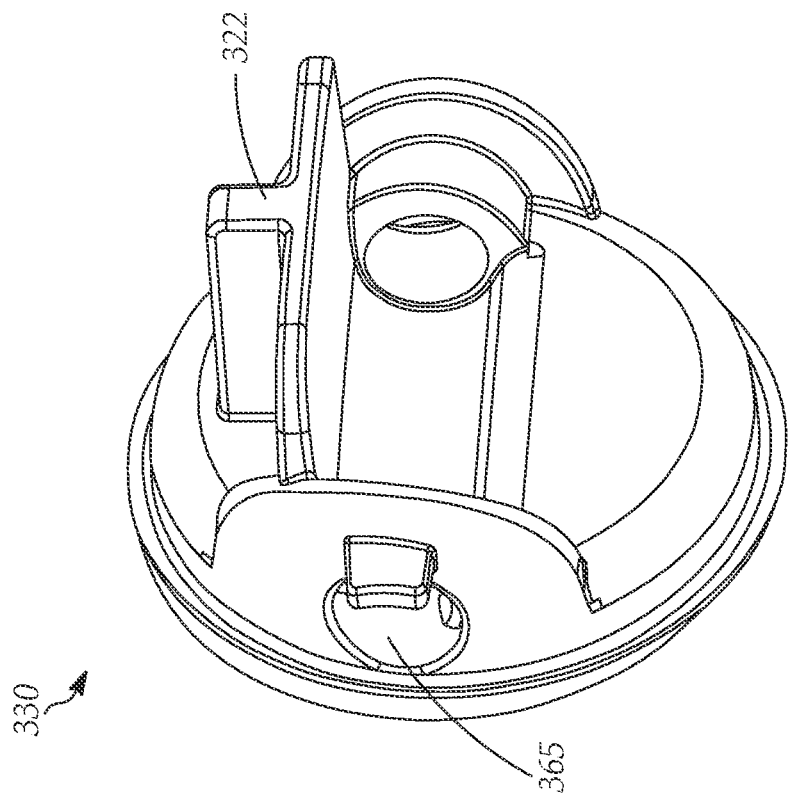
FIG. 45 is a rear perspective view of the restrictor member of the FIG. 44.

The restrictor member 330 is shown in further detail in the perspective views shown in FIGS. 44-45. The restrictor member 330 includes a keyed bore 365 for receiving the shaft 334 extending from the vane 332, and further includes a stop 322 that limits permissible rotation of the restrictor member 330 relative to a seat 324 of the adjustment member 353. As shown in the front view of FIG. 46, like the restrictor member 330, the restrictor member 330 further comprises an offset designed to facilitate movement of the restrictor member 330 between a closed position and an open position. More specifically, a greater surface area of the face 340 of the restrictor member 330 is positioned on one side of the bore 365 for receiving the shaft 334 than on the other side of the bore 365. As described above with regards to the restrictor member 130, this offset produces an opening torque about the shaft 334 during periods of exhalation.

Figure 47:
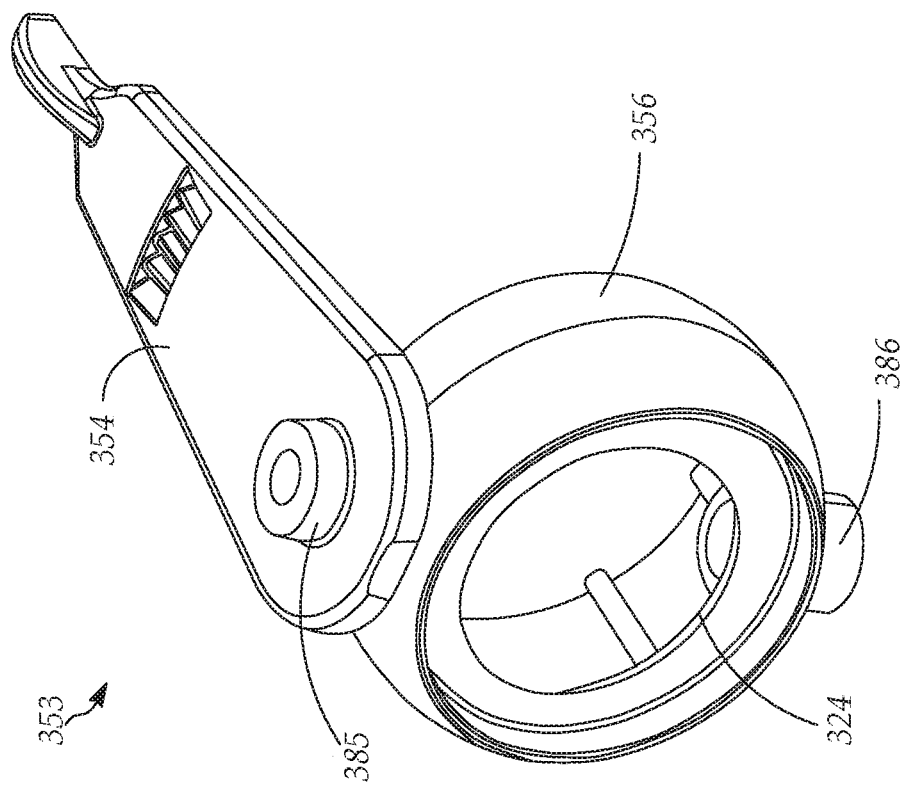
FIG. 47 is a front perspective view of an adjustment mechanism of the OPEP device of FIG. 35.
Figure 48:
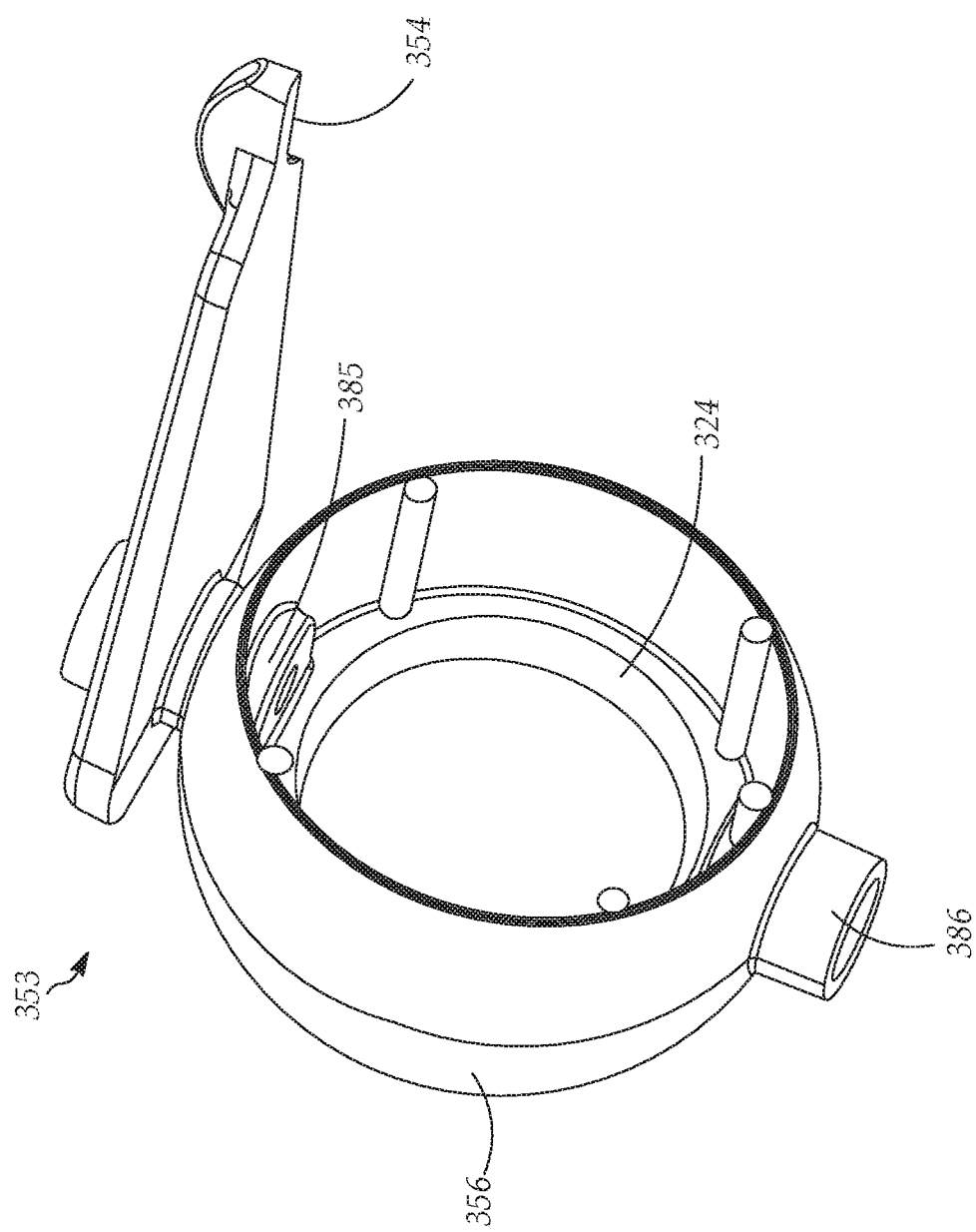
FIG. 48 is a rear perspective view of the adjustment mechanism of FIG. 47.

The adjustment mechanism 353 is shown in further detail in the front and rear perspective views of FIGS. 47 and 48. In general, the adjustment mechanism includes a frame 356 adapted to engage the sealing edge 370 of the flexible cylinder 371 formed on the inner casing 303. A circular opening in the frame 356 forms a seat 324 shaped to accommodate the restrictor member 330. In this embodiment, the seat 324 also defines the chamber inlet 304. The adjustment mechanism 353 further includes an arm 354 configured to extend from the frame 356 to a position beyond the housing 302 in order to permit a user to selectively adjust the orientation of the adjustment mechanism 353, and therefore the chamber inlet 304, when the OPEP device 300 is fully assembled. The adjustment mechanism 353 also includes an upper bearing 385 and a lower bearing 386 for receiving the shaft 334.

Figure 49:
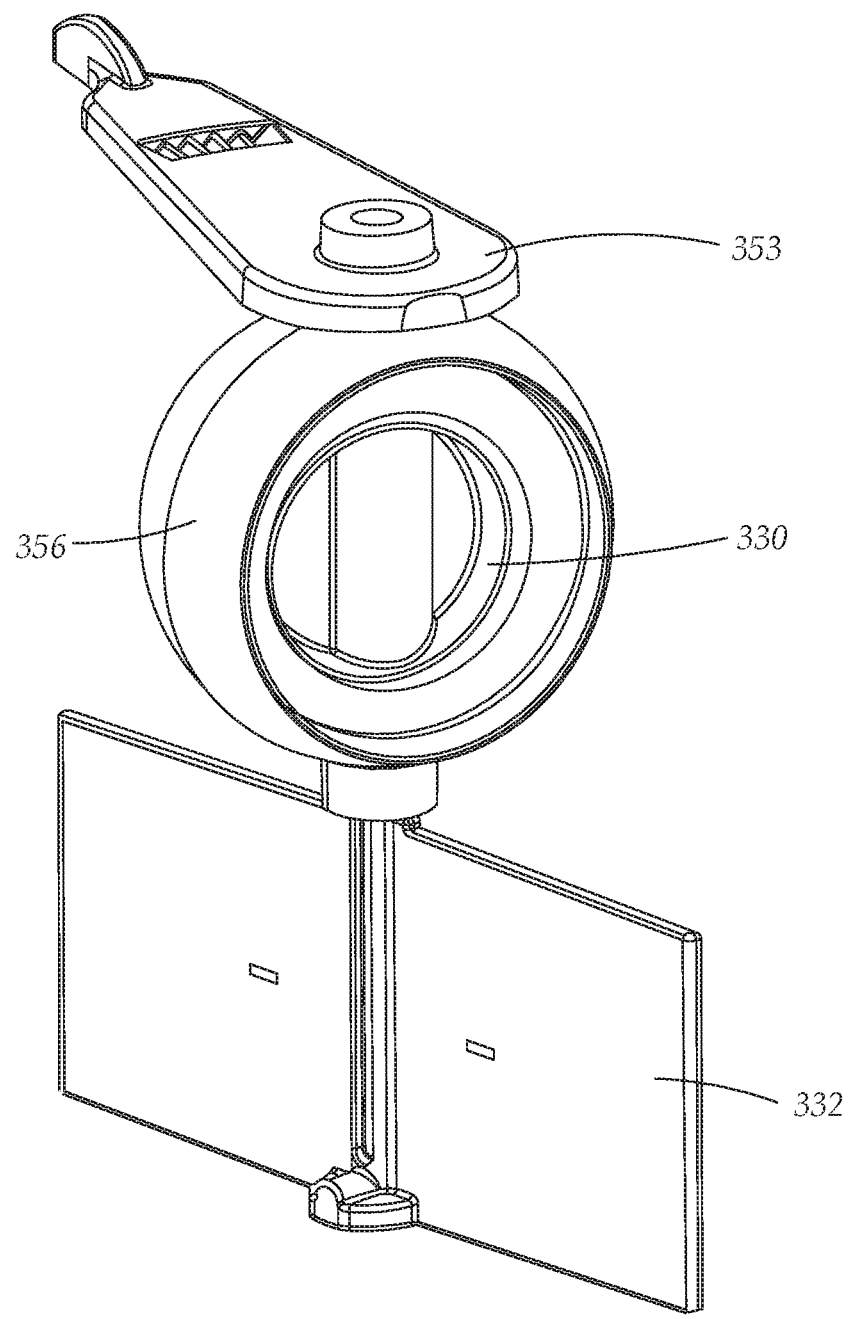
FIG. 49 is a front perspective view of the adjustment mechanism of FIGS. 47-48 assembled with the restrictor member of FIGS. 44-46 and the vane of FIG. 43.

An assembly of the vane 332, the adjustment mechanism 353, and the restrictor member 330 is shown in the perspective view of FIG. 49. As previously explained, the vane 332 and the restrictor member 330 are operatively connected by the shaft 334 such that rotation of the vane 332 results in rotation of the restrictor member 330, and vice versa. In contrast, the adjustment mechanism 353, and therefore the seat 324 defining the chamber inlet 304, is configured to rotate relative to the vane 332 and the restrictor member 330 about the shaft 334. In this way, a user is able to rotate the arm 354 to selectively adjust the orientation of the chamber inlet 304 relative to the restrictor member 330 and the housing 302. For example, a user may increase the frequency and amplitude of the OPEP therapy administered by the OPEP device 800 by rotating the arm 354, and therefore the frame 356, in a clockwise direction. Alternatively, a user may decrease the frequency and amplitude of the OPEP therapy administered by the OPEP device 300 by rotating the adjustment arm 354, and therefore the frame 356, in a counter-clockwise direction. Furthermore, as shown for example in FIGS. 35 and 37, indicia may be provided on the housing 302 to aid the user in the setting of the appropriate configuration of the OPEP device 300.

Figure 51:
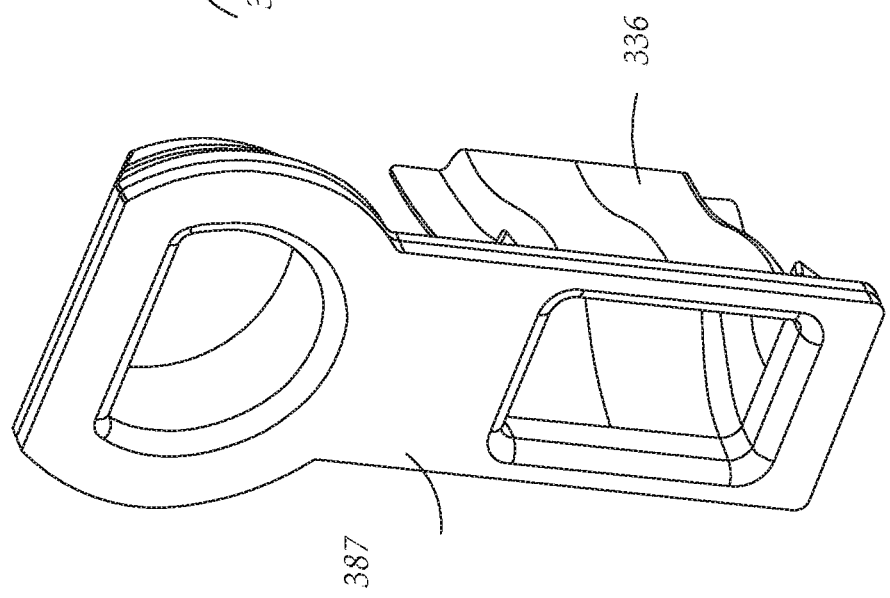
FIG. 51 is a rear perspective view of the variable nozzle of FIG. 50.
Figure 50:
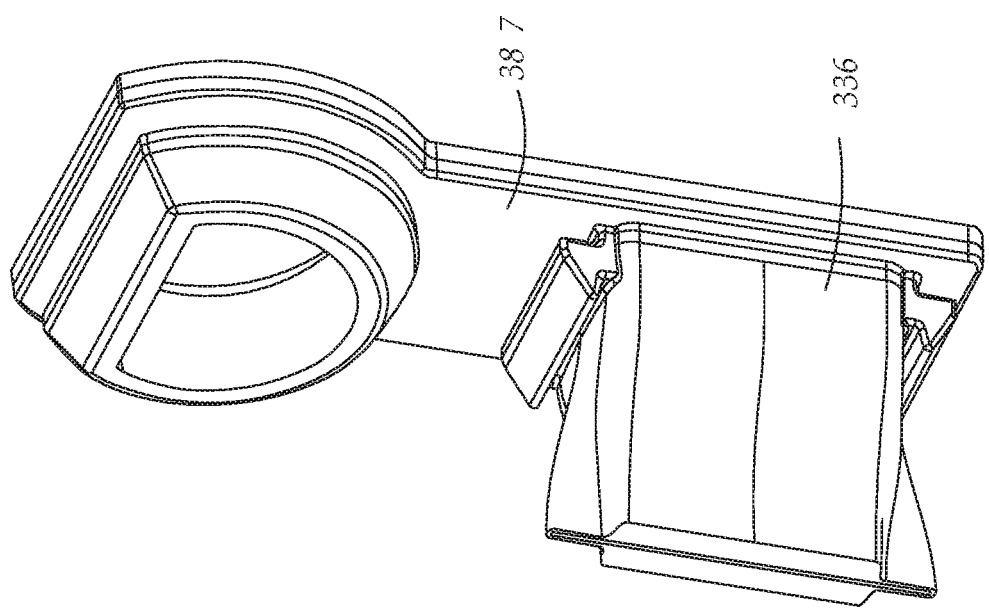
FIG. 50 is a front perspective view of a variable nozzle of the OPEP device of FIG. 35.

The variable nozzle 336 is shown in further detail in the front and rear perspective views of FIGS. 50 and 51. The variable nozzle 336 in the OPEP device 300 is similar to the variable nozzle 236 described above with regards to the OPEP device 200, except that the variable nozzle 336 also includes a base plate 387 configured to fit within one end 385 (see FIGS. 41-42) of the inner casing 303 and maintain the variable nozzle 336 between the rear section 305 and the inner casing 303. Like the variable nozzle 236, the variable nozzle 336 and base plate 387 may be made of silicone.

Figure 52:
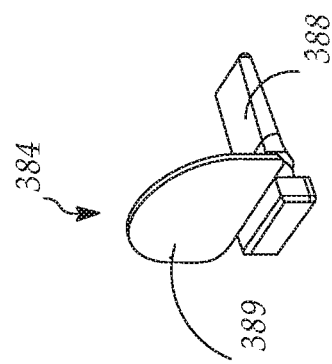
FIG. 52 is a front perspective view of the one-way valve of the OPEP device of FIG. 35.

The one-way valve 384 is shown in further detail in the front perspective view of FIG. 52. In general, the one-way valve 384 comprises a post 388 adapted for mounting in the front section 301 of the housing 302, and a flap 389 adapted to bend or pivot relative to the post 388 in response to a force or a pressure on the flap 389. Those skilled in the art will appreciate that other one-way valves may be used in this and other embodiments described herein without departing from the teachings of the present disclosure. As seen in FIGS. 39-40, the one-way valve 384 may be positioned in the housing 302 between the mouthpiece 309 and the inhalation port 311.

As discussed above in relation to the OPEP device 100, the OPEP device 300 may be adapted for use with other or additional interfaces, such as an aerosol delivery device. In this regard, the OPEP device 300 is equipped with an inhalation port 311 (best seen in FIGS. 35-36 and 38-40) in fluid communication with the mouthpiece 309. As noted above, the inhalation port may include a separate one-way valve 384 (best seen in FIGS. 39-40 and 52) configured to permit a user of the OPEP device 300 both to inhale the surrounding air through the one-way valve 384 and to exhale through the chamber inlet 304, without withdrawing the mouthpiece 309 of the OPEP device 300 between periods of inhalation and exhalation. In addition, the aforementioned commercially available aerosol delivery devices may be connected to the inhalation port 311 for the simultaneous administration of aerosol therapy (upon inhalation) and OPEP therapy (upon exhalation).

The OPEP device 300 and the components described above are further illustrated in the cross-sectional views shown in FIGS. 39-40. For purposes of illustration, the cross-sectional view of FIG. 39 is shown without all the internal components of the OPEP device 300.

The front section 301, the rear section 305, and the inner casing 303 are assembled to form a first chamber 314 and a second chamber 318. As with the OPEP device 100, an exhalation flow path 310, identified by a dashed line, is defined between the mouthpiece 309 and at least one of the first chamber outlet 306 (best seen in FIGS. 39-40 and 42) and the second chamber outlet 308 (best seen in FIG. 41), both of which are formed within the inner casing 303. As a result of the inhalation port 311 and the one-way valve 348, the exhalation flow path 310 begins at the mouthpiece 309 and is directed toward the chamber inlet 304, which in operation may or may not be blocked by the restrictor member 330. After passing through the chamber inlet 304, the exhalation flow path 310 enters the first chamber 314 and makes a 180° turn toward the variable nozzle 336. After passing through an orifice 338 of the variable nozzle 336, the exhalation flow path 310 enters the second chamber 318. In the second chamber 318, the exhalation flow path 310 may exit the second chamber 318, and ultimately the housing 302, through at least one of the first chamber outlet 306 or the second chamber outlet 308. Those skilled in the art will appreciate that the exhalation flow path 310 identified by the dashed line is exemplary, and that air exhaled into the OPEP device 300 may flow in any number of directions or paths as it traverses from the mouthpiece 309 or chamber inlet 304 to the first chamber outlet 306 or the second chamber outlet 308. As previously noted, the administration of OPEP therapy using the OPEP device 300 is otherwise the same as described above with regards to the OPEP device 100.

Huff Cough Simulation Device

Described herein is an embodiment of a respiratory treatment device that replicates or simulates a Huff Cough. In general, this treatment device prevents the flow of exhaled air through the device until a threshold pressure is reached at a user interface. Once a threshold pressure is reached, the device releases the exhaled air, causing a rapid increase in the flow of exhaled air through the device. This sharp increase in airflow translates directly to high air velocities in the user's airways, and therefore higher shear forces on secretions lining the airways, similar to that experienced during a Huff Cough.

The embodiment described herein is notable in that the threshold pressure at which exhaled air is released is selectively adjustable. This embodiment is also notable in that the release of exhaled air at a threshold pressure is dependent on a user's exhalation and easily repeatable by a user without coaching or supervision from a respiratory professional. Moreover, this embodiment is notable in that it does not include any metallic components (e.g., magnets, springs, etc.), which tend to increase production costs, and may be susceptible to corrosion.

Figure 53:
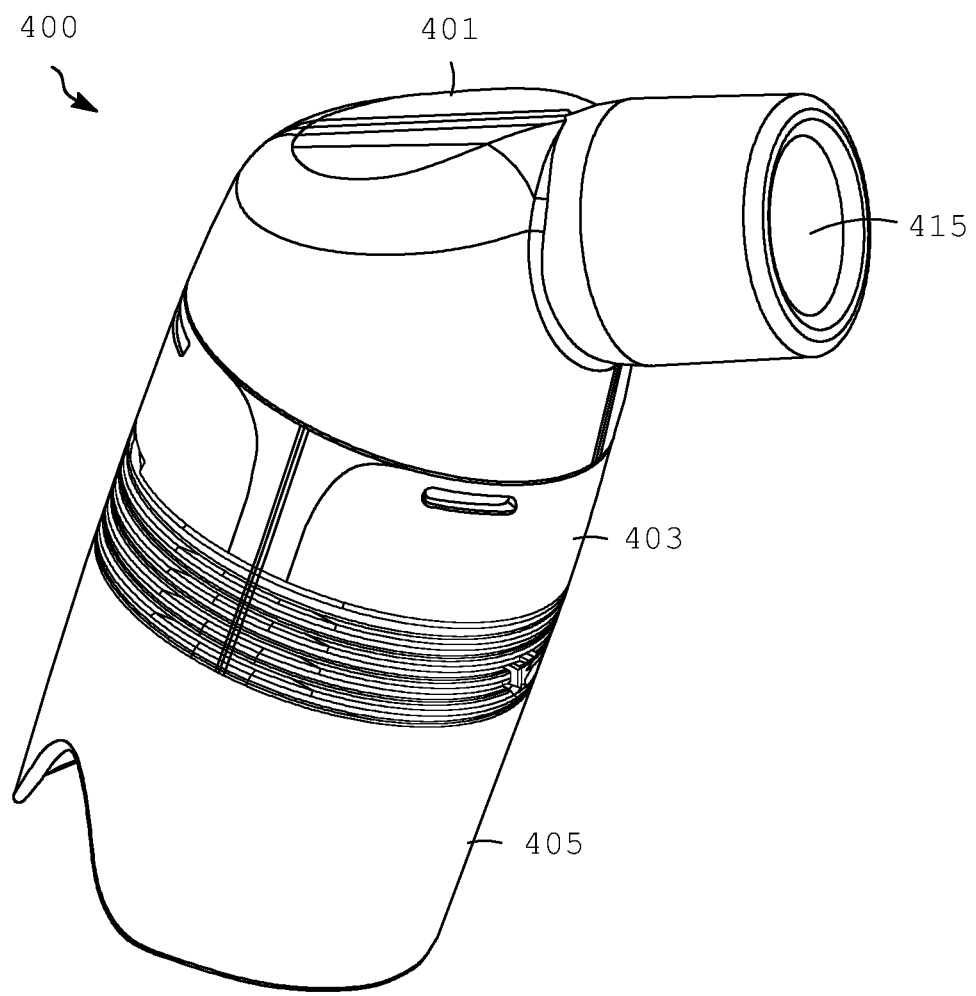
FIG. 53 is a perspective view of a Huff Cough simulation device.
Figure 54:
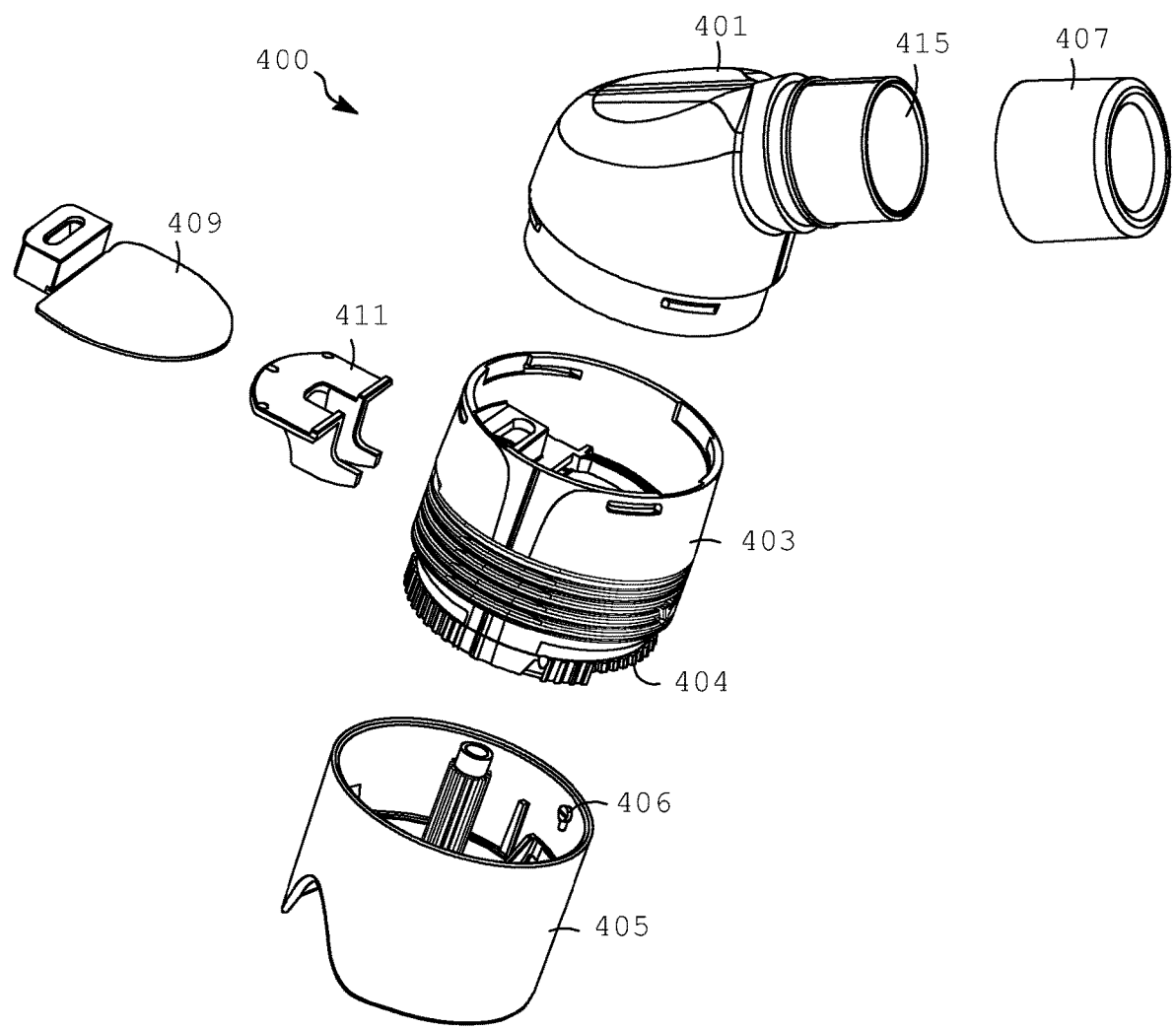
FIG. 54 is an exploded view of the device of FIG. 53.
Figure 55:
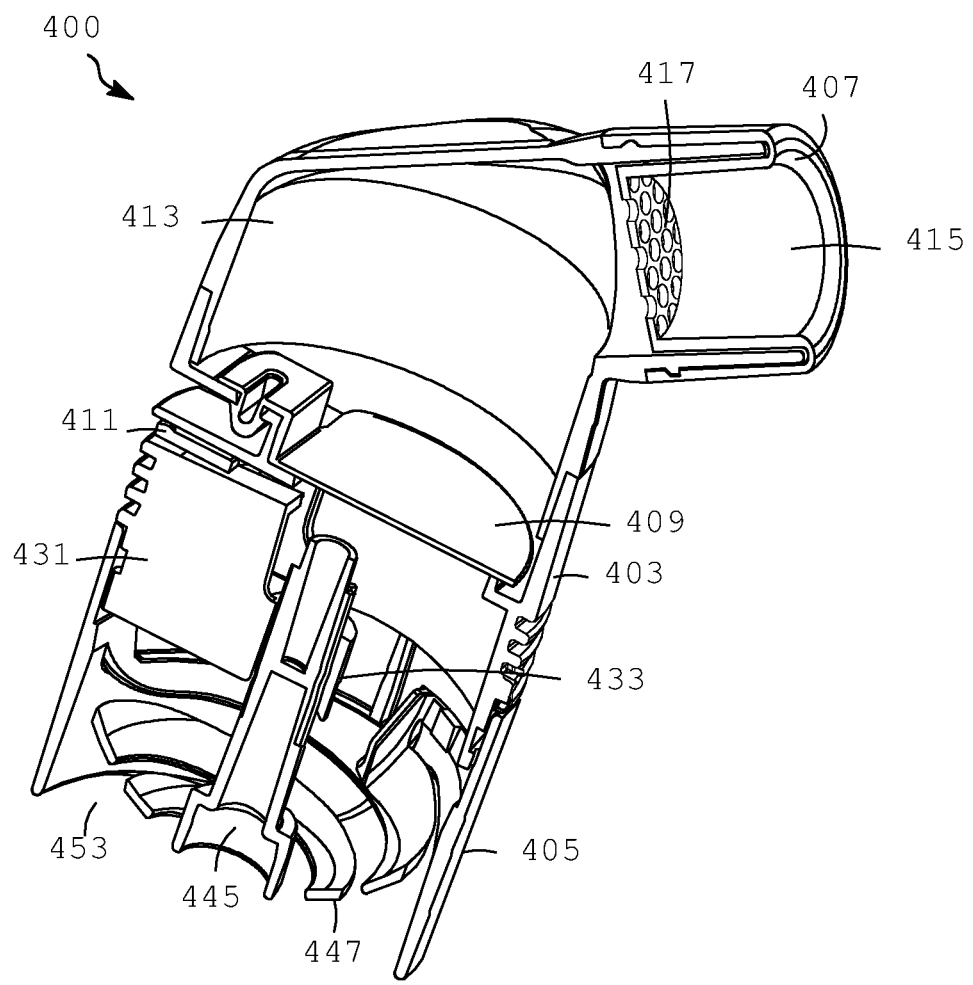
FIG. 55 is a cross-sectional perspective view of the device of FIG. 53.

FIGS. 53-55 show a Huff Cough simulation device 400. FIG. 53 is a perspective view of the device 400. FIG. 54. Is an exploded view of the device 400. FIG. 55 is a cross-sectional view of the device 400. In general, the device 400 includes a top housing portion 401, a middle housing portion 403, a bottom housing portion 405, a mucus trap 407, a valve 409, and a valve brace 411.

As seen in FIGS. 53-55, the top housing portion 401, the middle housing portion 403, and the bottom housing portion 405 are removably connectable such that the components of the device 400 may be periodically accessed for cleaning and/or replacement. The housing portions may be removably connectable by any suitable means, including for example, threading, compression fit, or snap fit. When connected, the top housing portion 401 and the middle housing portion 403 form an interior chamber 413.

Figure 56:
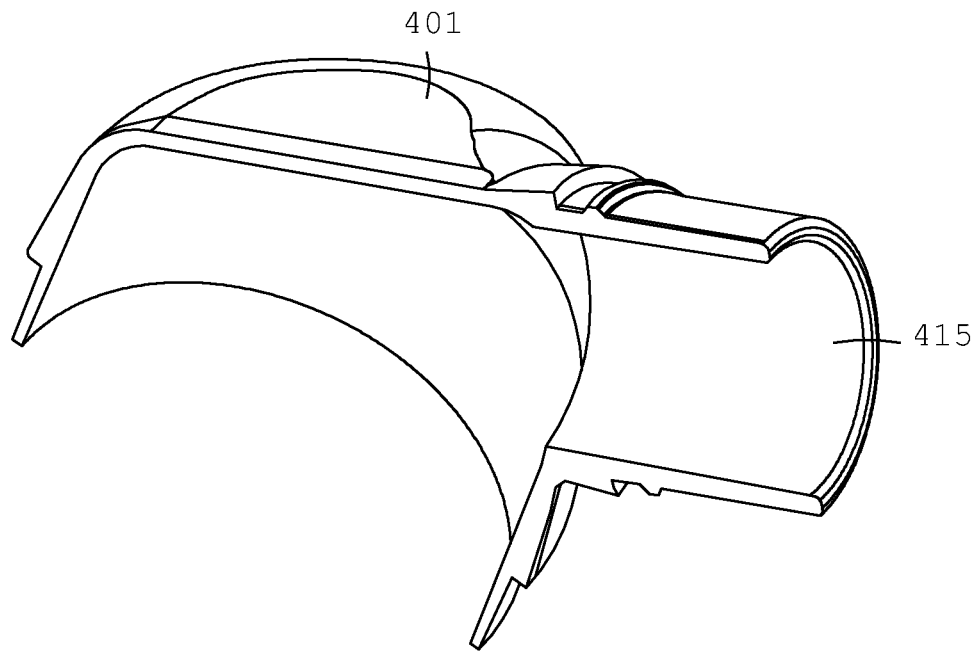
FIG. 56 is a cross-sectional perspective view of a top portion of the housing of the device of FIG. 53.

FIG. 56 is a cross-sectional view of the top housing portion 401. The top housing portion may be made of any suitable plastic material, including for example, a high-temperature polypropylene (PP). The top housing portion 401 includes an inlet or mouthpiece 415 for receiving exhaled air from a user. Preferably, the mouthpiece is circular and roughly 1 inch in diameter in order to promote glottal patency throughout a user's exhalation. However, it should be appreciated that other user interfaces may form, or may be in fluid communication with the inlet or mouthpiece 415, including for example, gas masks, breathing tubes, or the like. Moreover, it should be appreciated that the device 400 may be used in conjunction or combination with other respiratory treatment devices that administer therapy upon inhalation, including for example, a nebulizer, a metered dose inhaler with a valved holding chamber, or a dry powder inhaler. In this way, the device 400 may administer therapy upon a user's exhalation, while the aforementioned devices may administer therapy upon a user's inhalation.

Figure 57:
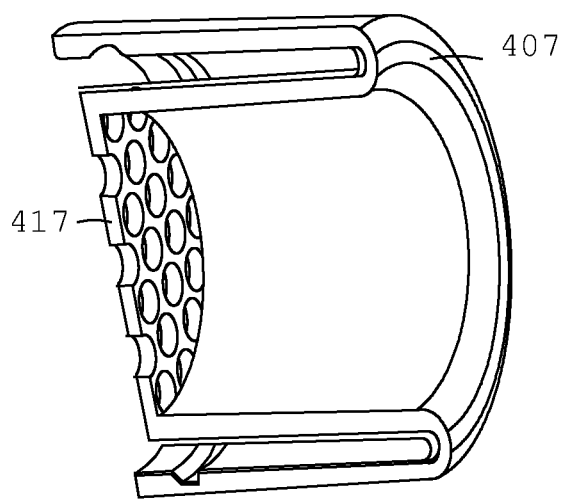
FIG. 57 is a cross-sectional perspective view of a mucus trap of the device of FIG. 53.

FIG. 57 is a cross-sectional view of the mucus trap 407. The mucus trap 407 may also be made of any suitable plastic material, such as a high-temperature polypropylene (PP). The mucus trap 407 is sized and shaped to fit around and within the mouthpiece 415, as shown in FIG. 55. The mucus trap 407 and the mouthpiece 415 may be removably connectable by any suitable means, including for example, snap fit (as shown in FIG. 55), compression fit, or threading. The mucus trap 407 includes a grate 417 having plurality of small openings, and is configured to capture any secretions expelled out of a user's mouth during exhalation, while permitting exhaled air to pass through the grate into the device 400.

Figure 58:
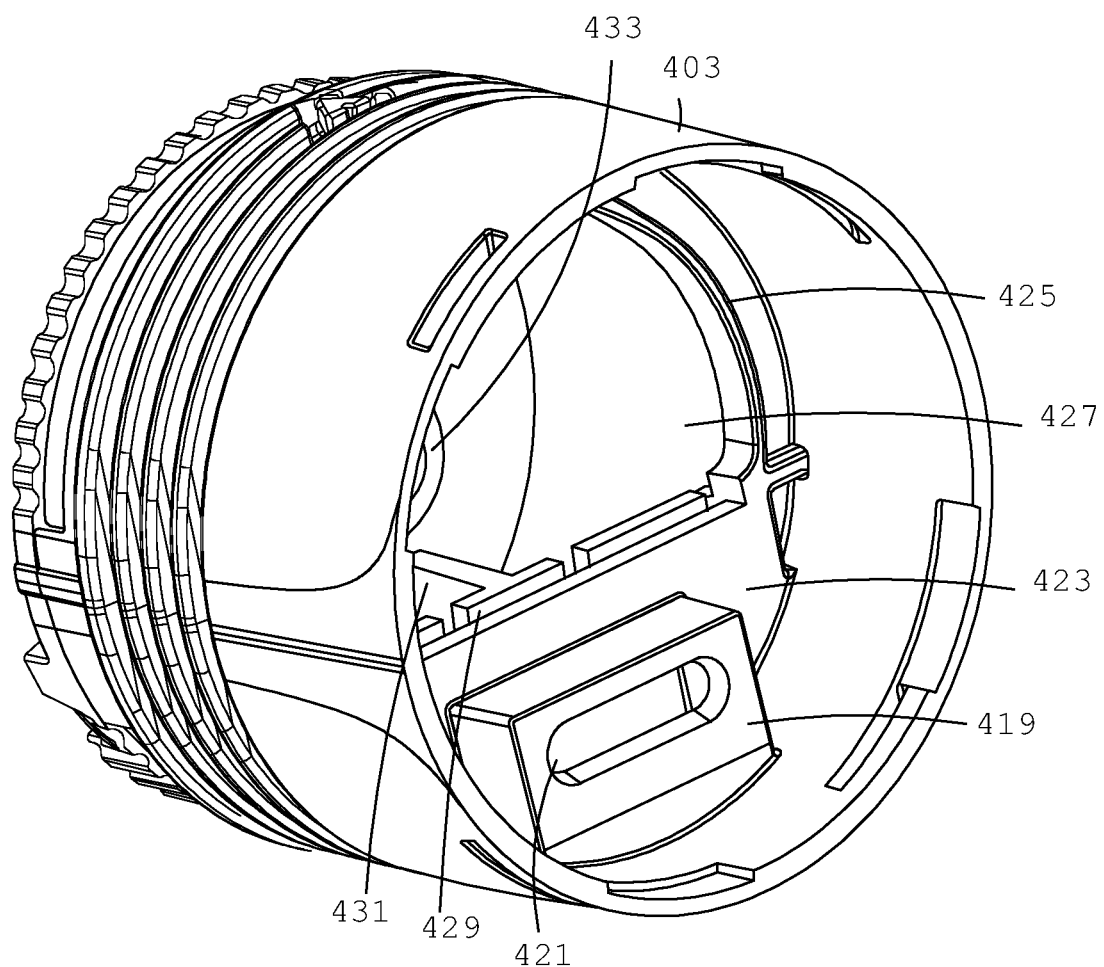
FIG. 58 is a perspective view of a middle portion of the housing of the device of FIG. 53.
Figure 59:
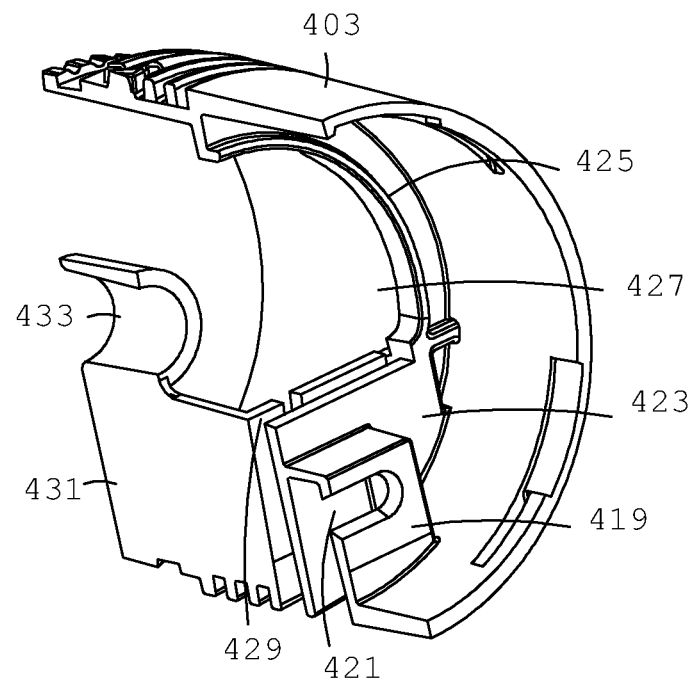
FIG. 59 is a cross-sectional perspective view of the middle portion of the housing of FIG. 53.

FIGS. 58-59 are perspective and cross-sectional views of the middle housing portion 403. The middle housing portion 403 may also be made of a suitable plastic material, such as high-temperature polypropylene (PP). The middle housing portion 403 includes a mount 419 having an opening 421 for receiving a barb 439 molded with the valve 409, a ledge 423 extending into the interior of the middle housing portion 403, and a rim 425 formed around the periphery of the middle housing portion 403. Together, the ledge 423 and the rim 425 form a valve seat for the valve 409 and define an opening 427 through which exhaled air passes through the middle housing portion 403 when the valve 409 is in an open position, as discussed below. The middle housing portion 403 also includes a slot 429 for receiving the valve brace 411, and a support structure 431 extending into the interior of the middle housing portion 403, having a cylindrical support 433 adapted to receive a rod extending from the reset button, as discussed below.

Figure 60:
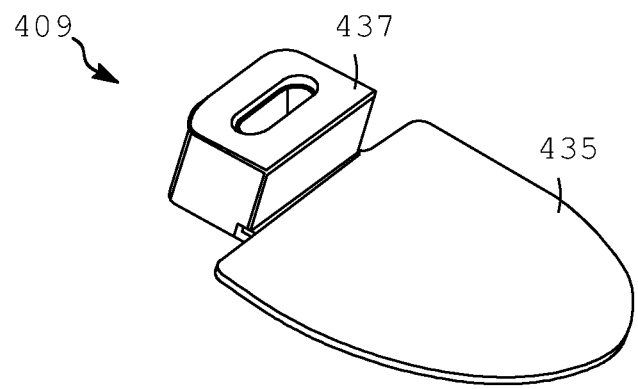
FIG. 60 is a perspective view of the valve of the device of FIG. 53.
Figure 61:
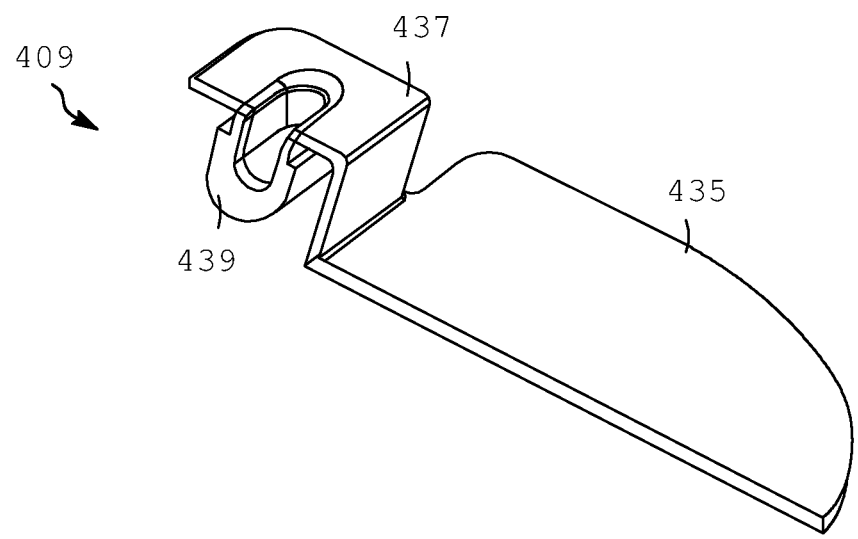
FIG. 61 is a cross-sectional perspective view of the valve of FIG. 60.
Figure 67:
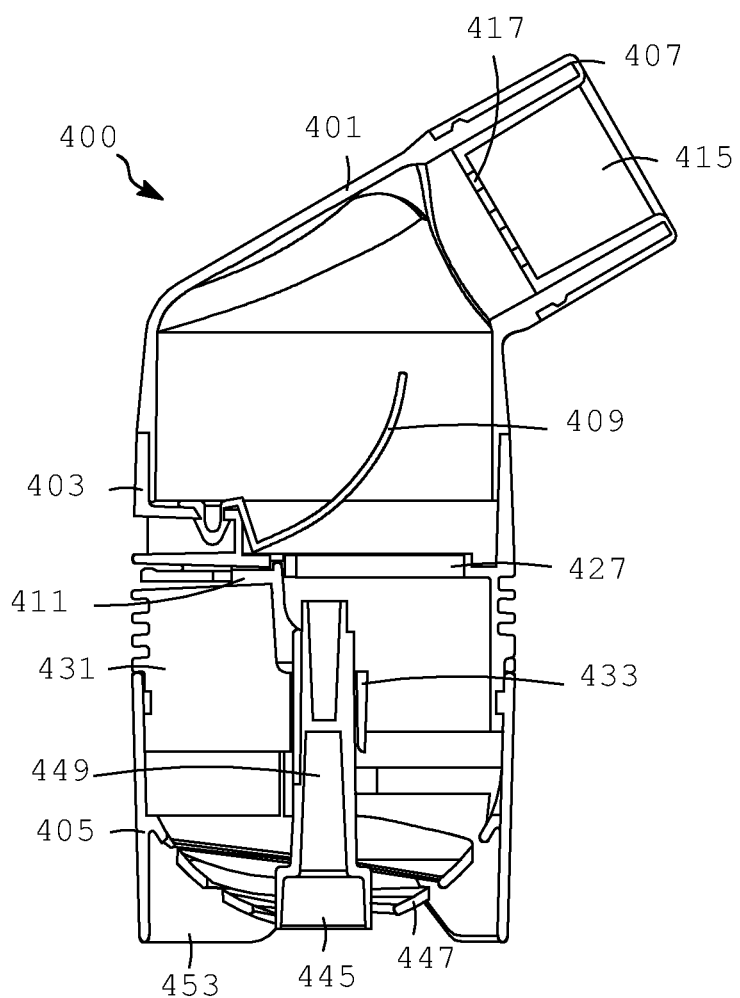
FIG. 67 is a cross-sectional view of the device of FIG. 53 after a period of exhalation, showing the valve of FIG. 60 being reset to the closed position shown in FIG. 65.

FIGS. 60-61 are perspective and cross-sectional views of the valve 409. In general, the valve 409 is configured as a flap valve having a flap 435 and a post 437 that includes a barb 439 for securing the valve 409 to the mount 419 in the middle housing portion 403. It should be appreciated that other means of securing the valve 409 to the middle housing portion 403 may be used, including for example, heat staking, living hinges, and other barb designs. The flap 435 is sized to cover the opening 421 and rest on the valve seat formed by the ledge 423 and rim 425 in the middle housing portion 403. The flap 435 is configured to bend relative to the post 437 between an open position (shown in FIG. 55) in a first direction, and during a valve reset, in the opposite direction (shown in FIG. 67). The flap 435 is also configured to open in the opposite direction toward an open inhalation position (e.g., as shown in FIG. 67) during a period of inhalation, or in response to an inhalation pressure at the inlet or mouthpiece 415. The valve may be made of a rubber material, for example, a silicone rubber, having a hardness of 40-50 Shore A durometer.

Figure 66:
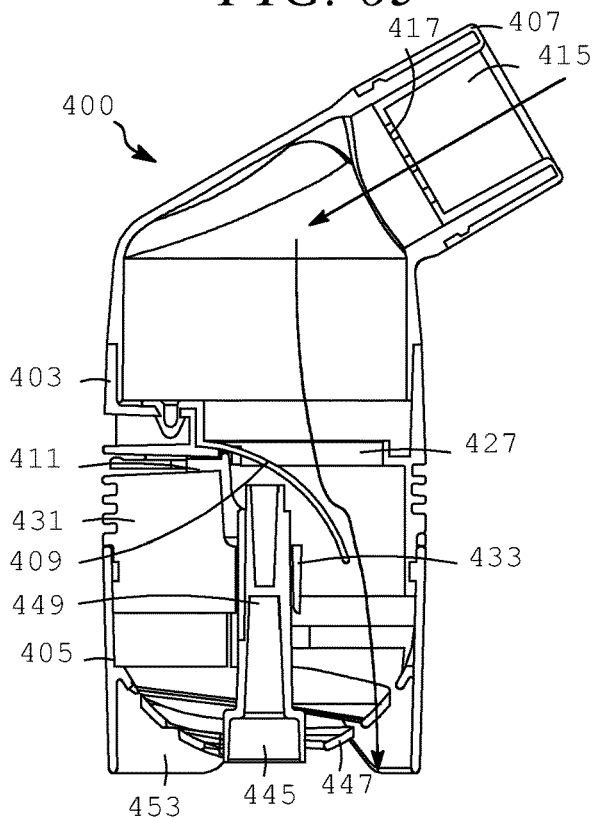
FIG. 66 is a cross-sectional view of the device of FIG. 53 during a period of exhalation, showing the valve of FIG. 60 in an open position.

The interaction of the valve 409 with the valve seat formed by the ledge 423 and the rim 425 affects the threshold pressure at which the valve will blow through the opening 421, and move from the closed position, shown in FIG. 43, to an open position, shown in FIG. 66. For example, the diameter of the flap 435, the diameter of the opening 421, the stiffness or hardness of the valve material, the valve thickness, and the friction between the valve and valve seat and/or the valve brace 411, all affect the threshold pressure at which the valve will blow through the opening 421. The valve 409 may be accessed and selectively replaced with a valve having different properties in order to increase or decrease the threshold pressure.

Figure 62:
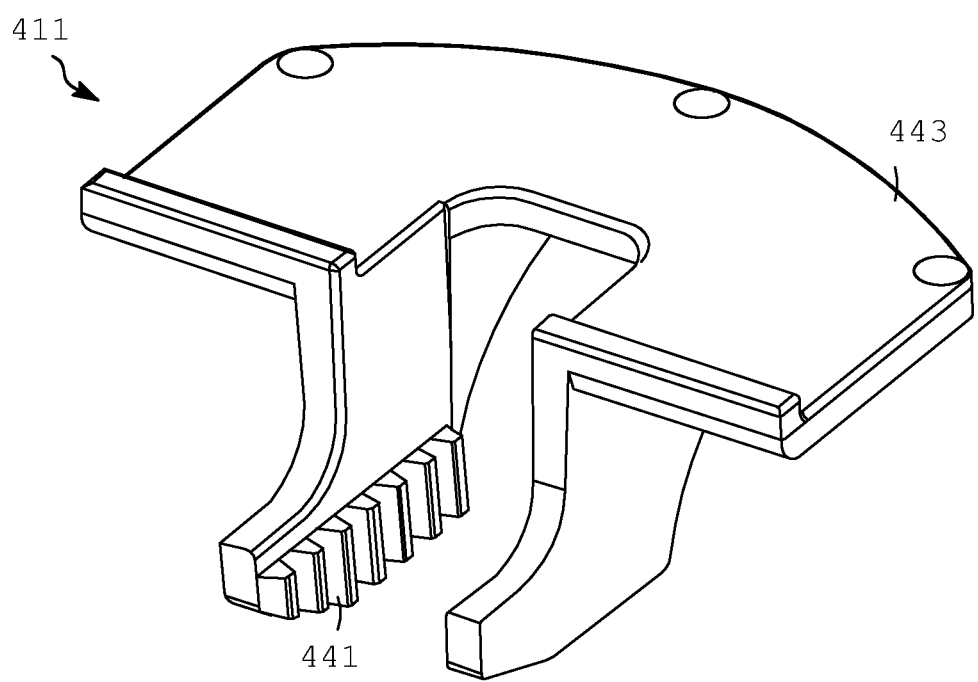
FIG. 62 is a perspective view of a valve brace of the device of FIG. 53.

FIG. 62 is a perspective view of the valve brace 411. The valve brace 411 is sized and shaped to fit in a sliding engagement within the slot 429 formed in the middle housing portion 403. The valve brace 411 further includes a support face 443 and series or a rack of teeth 441 extending therefrom configured to engage a corresponding series of gear teeth 451 (e.g., a pinion) on the lower housing portion 405. The valve brace 411 may also be made of a suitable plastic material, such as Acetal (POM) or poly (p-phylene oxide) (PPO).

Figure 63:
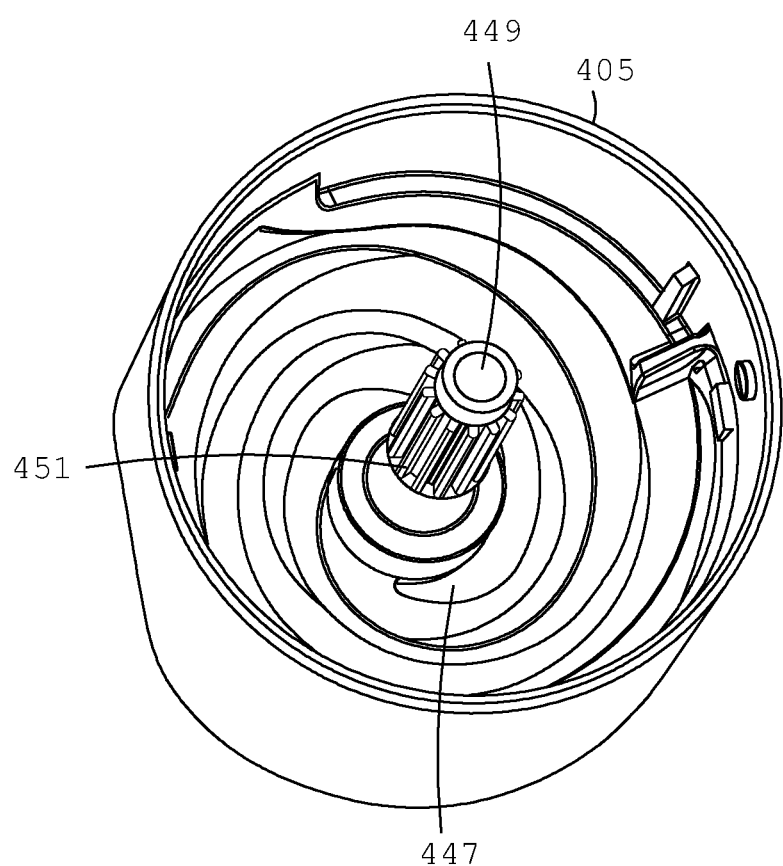
FIG. 63 is a perspective view of a lower portion of the housing of the device of FIG. 53, showing a reset button connected to the lower portion of the housing via a molded-in spring.
Figure 64:
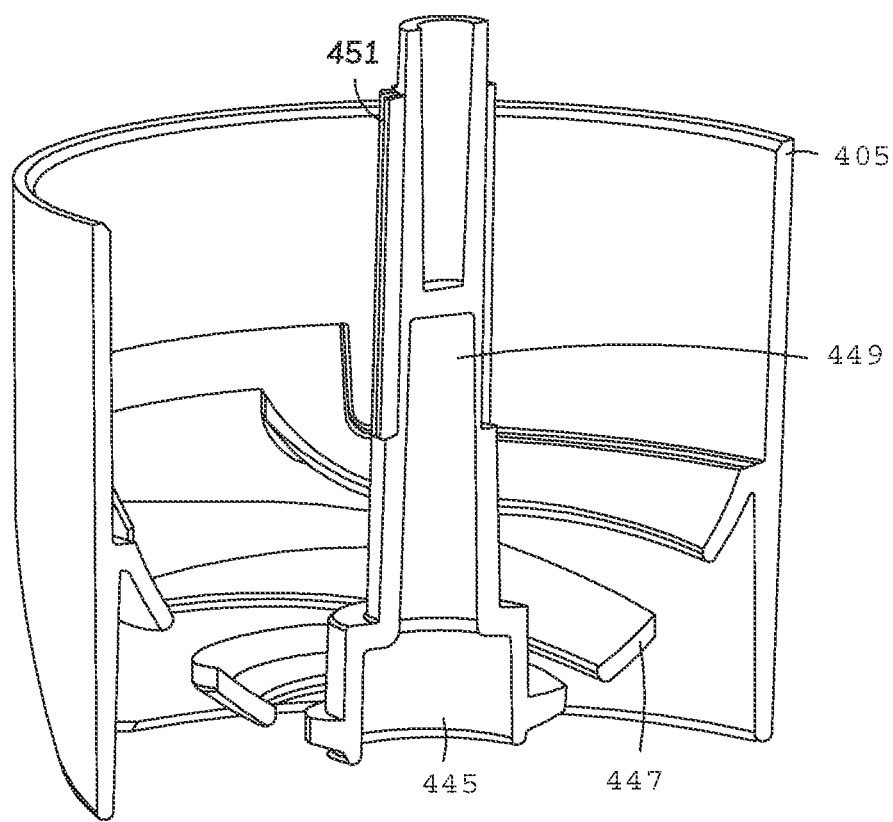
FIG. 64 is a cross-sectional perspective view of the lower portion of the housing of FIG. 63, showing the reset button connected to the lower portion via the molded-in spring.

FIGS. 63-64 are perspective and cross-sectional views of the lower housing portion 405. The lower housing portion 405 may also be made of a suitable plastic material, such as Acetal (POM). The lower housing portion 405 includes a reset button 445 connected to the lower housing portion 405 via a molded-in spring 447 comprised of a plurality of spiraling segments extending between the lower housing portion 405 and the reset button 445. An open end of the lower housing portion 405 functions as an outlet 453. Exhaled air is permitted to exit the device 400 through the openings formed between the spiraling segments of the molded-in spring 447, and ultimately, the outlet 153.

The reset button 445 further includes a rod 449 extending into the lower housing portion 405 that has a series of gear teeth 451 (e.g., a pinion) for engaging a corresponding series or a rack of teeth 441 on the valve brace 411. The reset button 445 may also include additional protrusions, wings, or markings (not shown) to aid a user in depressing and/or rotating the reset button 445. The molded-in spring 447 is configured to permit a user to push the reset button 145 and move the reset button 445 and rod 449 relative to the lower hosing portion 405 to reset the valve 409 to the closed position, as described further below. The series of gear teeth 451 on the rod 449 is configured to engage the rack of teeth 441 on the valve brace 411 such that rotation of the reset button 445 advances or retracts the valve brace 411 relative to the valve 409, as described further below.

Figure 65:
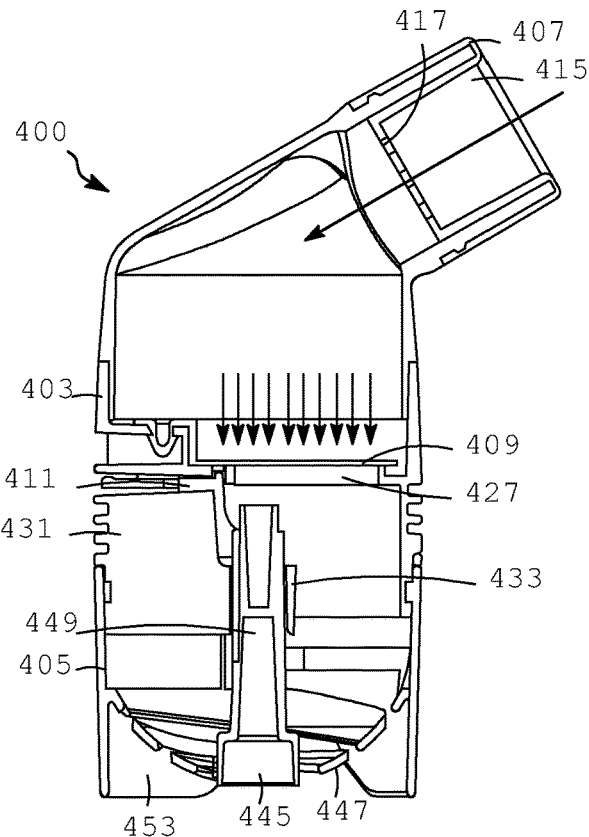
FIG. 65 is a cross-sectional view of the device of FIG. 53 during a period of exhalation, showing the valve of FIG. 60 in a closed position.

Operation of the device 400 will now be described. FIGS. 65-67 are cross-sectional side views illustrating simulation of a Huff cough during a period of exhalation, and reset of the valve 409. FIGS. 68A-B and 69A-B are side and perspective views of the lower portion of the housing 405, illustrating operation of the reset button 445 and the molded-in spring 447 to reset the valve 409.

Operation of the device 400 begins with the valve 409 in a closed position, as shown in FIG. 65, where the flow of air through the opening 427 is restricted. As a user begins to exhale into the device 400 through the inlet or mouthpiece 415, exhalation pressure begins to build within the device 400, and specifically, against the valve 409. As exhalation pressure builds, the flap 435 on the valve 409 begins to deform into a bowl shape, bringing the periphery of the flap 435 closer to the edges of the valve seat formed by the ledge 423 and the rim 425 that define the opening 427. As the exhalation pressure continues to build, the periphery of the flap 435 continues to move closer to the edges of the valve seat. When a threshold exhalation pressure is achieved, the periphery of the flap 435 is no longer supported by the valve seat, and the flap 435 is free to quickly blow through the opening 427, as shown in FIG. 66, thereby resulting in a rapid flow of air through the device 400, from the mouthpiece 415 to the outlet 453. The rapid flow of air through the device 400 also results in high air flow velocities in the user's airways. In the event that secretions are loosened within the user's respiratory system and expelled out of the user's mouth, the mucus trap 407 may capture the discharge and prevent it from entering the device 400.

Figure 68A:
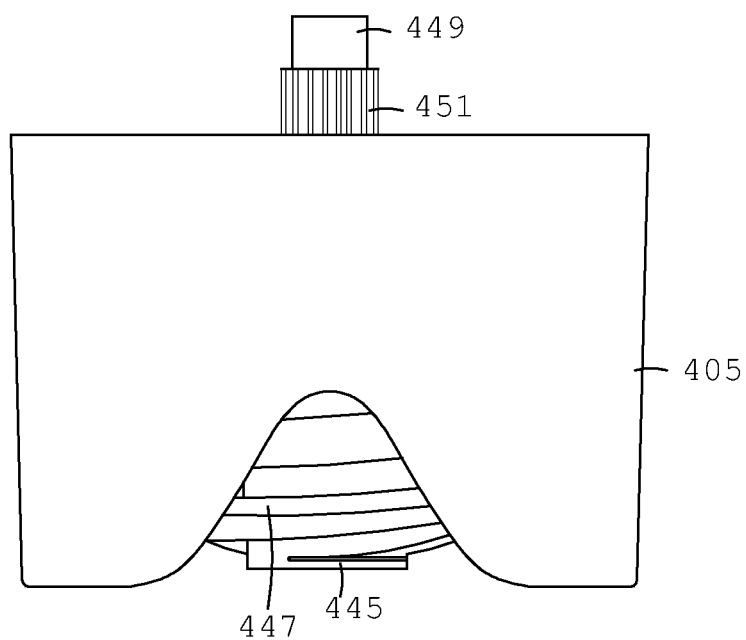
FIGS. 68A-B are side and perspective views of the of the lower portion of the housing of FIG. 63, showing the reset button in a default position.
Figure 68B:
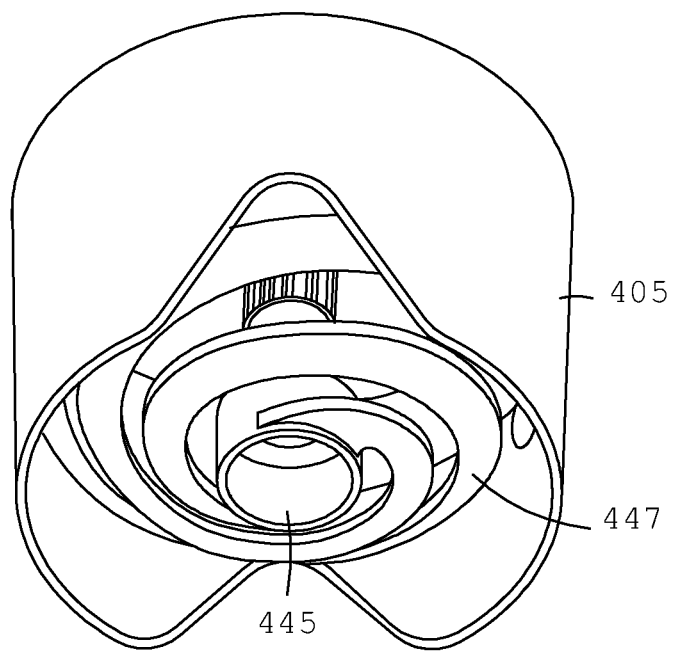
Figure 69A:
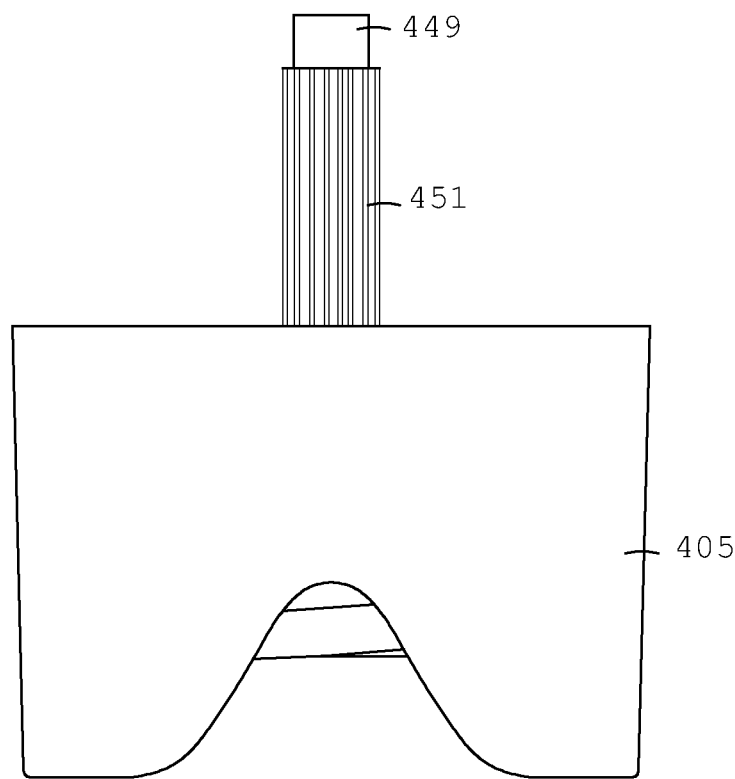
FIGS. 69A-B are side and perspective views of the of the lower portion of the housing of FIG. 63, showing the reset button in an extended position for resetting the valve of FIG. 60 to the closed position shown in FIG. 65.
Figure 69B:
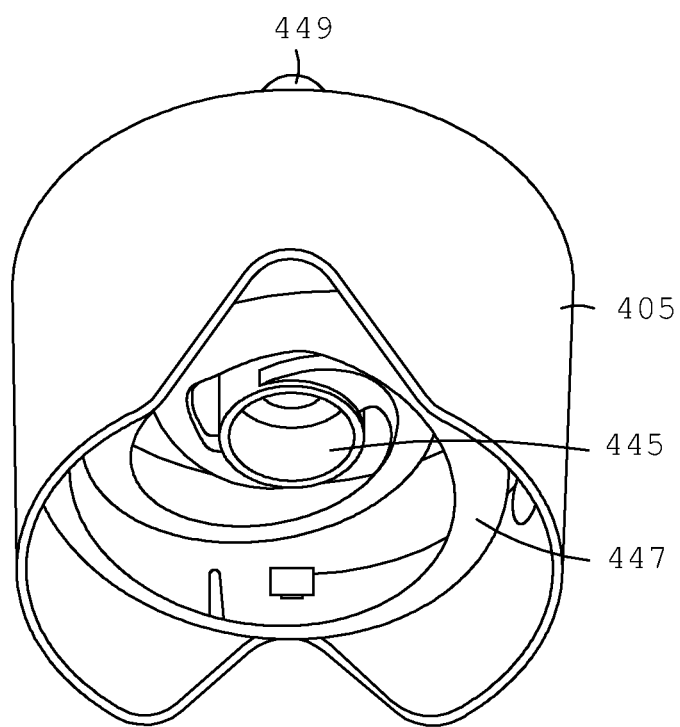

Upon completion of exhalation, the valve 409 may be reset to the closed position, shown in FIG. 65, by depressing the reset button 445, as shown in FIGS. 68A-B and 69A-B. FIGS. 68A-B show the reset button 445 and the molded-in spring 447 in a default, or "at-rest" position. In this position, the rod 449 is not in engagement with the valve 409, as seen in FIGS. 65-66. FIGS. 69A-B show the reset button 445 and the molded-in-spring 447 in a depressed position. In this position, the rod 449 is in an extended position, such that it may engage the flap 435 of the valve 409, pushing the flap 435 back through the opening 427, as shown in FIG. 67. Depression of the reset button 445 also creates a tension in the molded-in spring 447. When the reset button 445 is released in the depressed position, the tension in the molded-in spring 447 returns the reset button 445, the rod 449, and the molded-in spring 447 to the default or "at-rest" position, shown in FIG. 68-B, as well as FIG. 65. Similarly, pushing the flap 435 to the position shown in FIG. 66 creates a tension or a bias in the valve 409, such that when the rod 449 returns to the "at-rest" position, the flap 435 returns to the closed position, shown in FIG. 65. The aforementioned process may then be repeated by the user. A user may also inhale through the inlet or mouthpiece 415, causing the flap 435 of the valve 409 to move from the closed position, as shown in FIG. 65, to an open inhalation position, for example, as shown in FIG. 67.

Figure 70A:
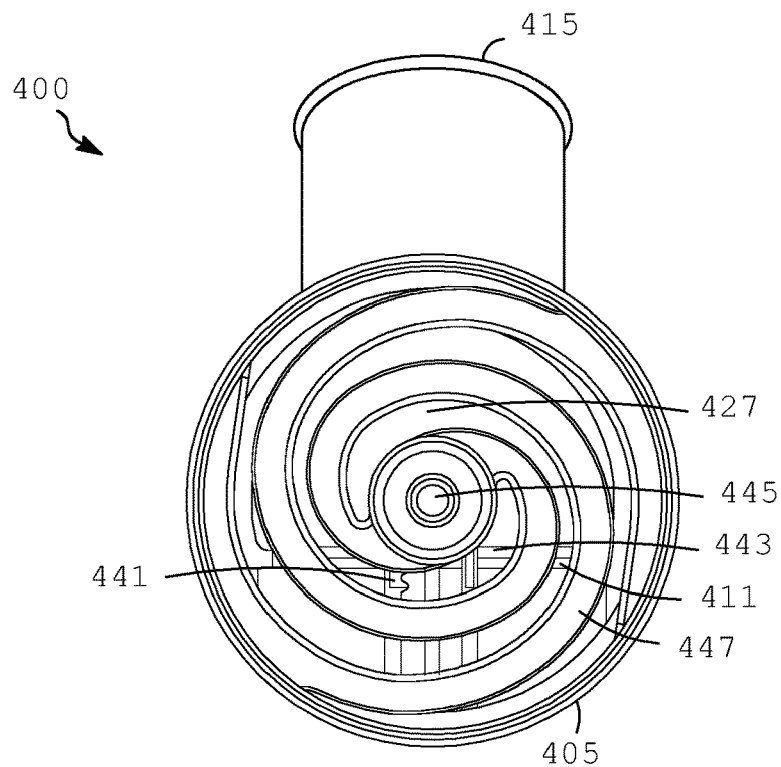
FIGS. 70A-C are bottom views of the device of FIG. 53, showing rotation of the reset button to selectively adjust the position of the valve brace relative to the valve of FIG. 60.
Figure 70B:
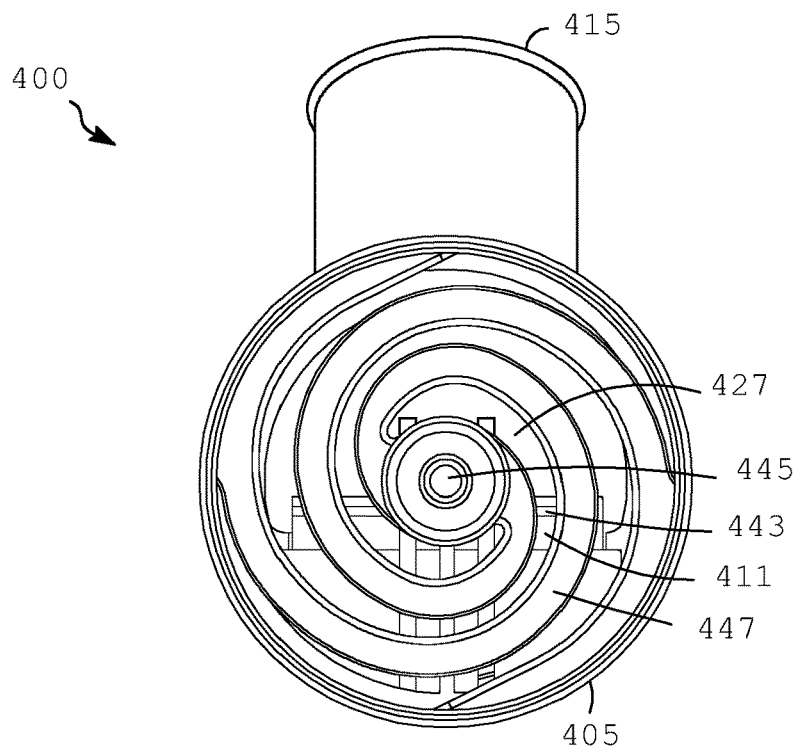
Figure 70C:
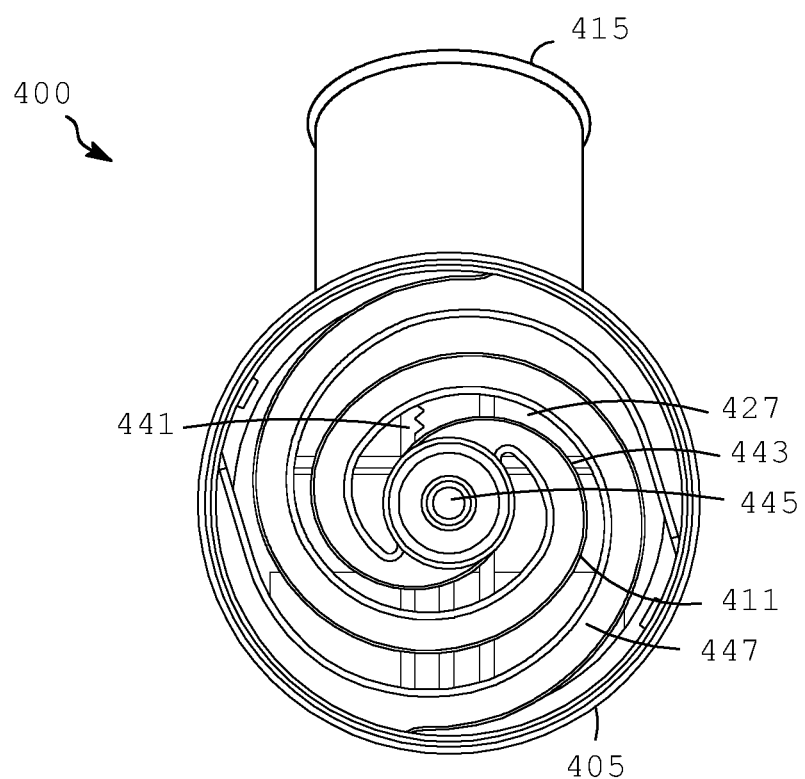

A user may selectively adjust the threshold exhalation pressure at which the valve 409 blows through the opening 427 by rotating the reset button 445, as illustrated in FIGS. 70A-C. Specifically, FIGS. 70A-C are bottom views of the device 400, illustrating rotation of the reset button 445 to selectively adjust the position of the valve brace 411 relative to the opening 427 and the valve 409. As noted above, the reset button 445 includes a rod 449 having a series of gear teeth 451 (e.g., a pinion) for engaging a corresponding series or a rack of teeth 441 on the valve brace 411. Therefore rotation of the reset button 445, and consequently the rod 449 and gear teeth 451, results in linear movement of the valve brace 411, as shown in FIGS. 70A-C. As shown in FIG. 54, a plurality of detents 404 on the middle housing portion 403 are configured to engage at least one detent 406 on the lower housing portion 405 to provide the user with tactile feedback as the user rotates the reset button 445 to adjust the threshold exhalation pressure in discrete intervals. The engagement of the at least one detent 406 with the plurality of detents 404 also operates to fix the reset button 445 to the extent the reset button 445 is rotationally biased by the molded-in spring 447 after rotation by a user.

FIG. 70A shows the valve brace 411, and therefore the support face 443, in a retracted position in which the support face 443 is not supporting the flap 435 of the valve 411, and the opening 427 remains unobstructed by the support face. FIG. 70B shows the valve brace 411 in a partially extended position in which the support face 443 is supporting a portion of the flap 435 and partially obstructing the opening 427. FIG. 70C shows the valve brace 411 in a further extended position in which the support face 443 is supporting a larger portion of the flap 435, and obstructing a larger portion of the opening 427. By rotating the reset button 445 to advance the position of the valve brace 411 relative to the opening 427 and the valve 409, the user is able to selectively increase the portion of the valve brace supporting the flap 435, and also reduce the area of the flap 435 exposed to the exhalation pressure that is subject to blow through the opening 427. Likewise, by rotating the reset button 445 in the opposite direction to retract the position of the valve brace 411 relative to the opening 427 and the valve 409, the user is able to selectively decrease the portion of the valve brace supporting the flap 435, and also increase the area of the flap 435 exposed to the exhalation pressure that is subject to blow through the opening 427. In this way, the use may selectively increase or decrease the threshold exhalation pressure.

Combined OPEP and Huff Cough—Embodiment One

Figure 71A:
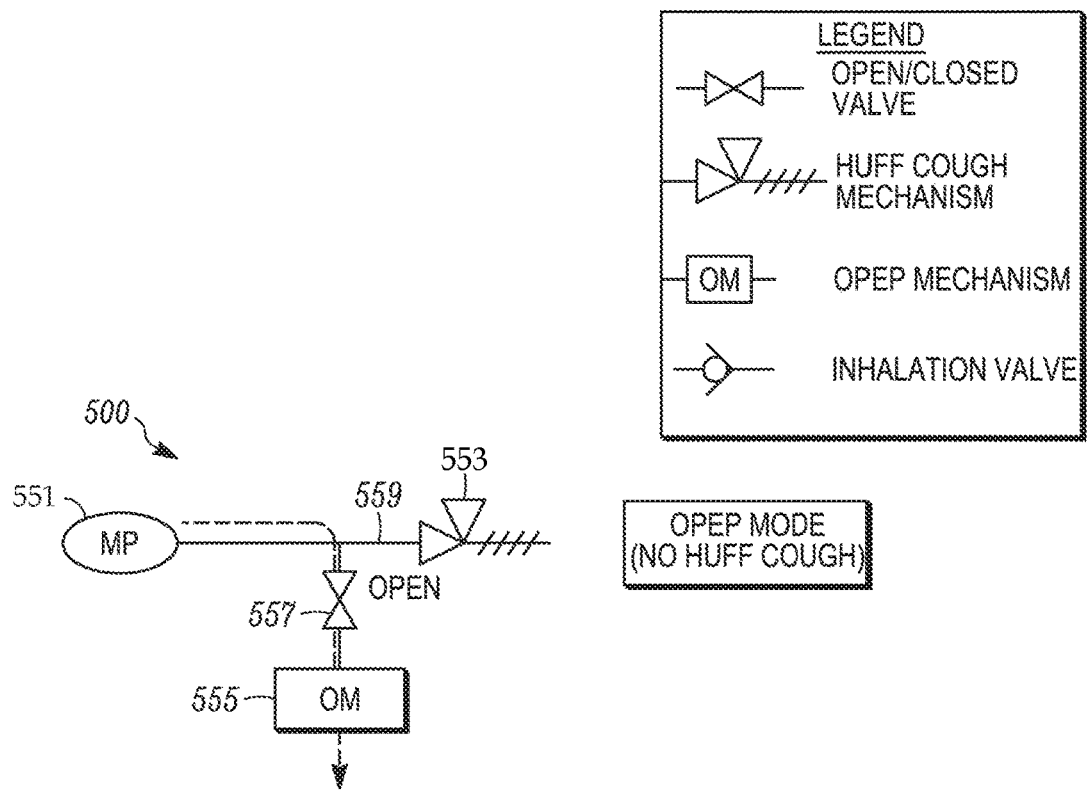
FIGS. 71A and 72A are schematics illustrating the primary components of a combined OPEP and Huff Cough simulation device according to an embodiment of the present disclosure.
Figure 71B:
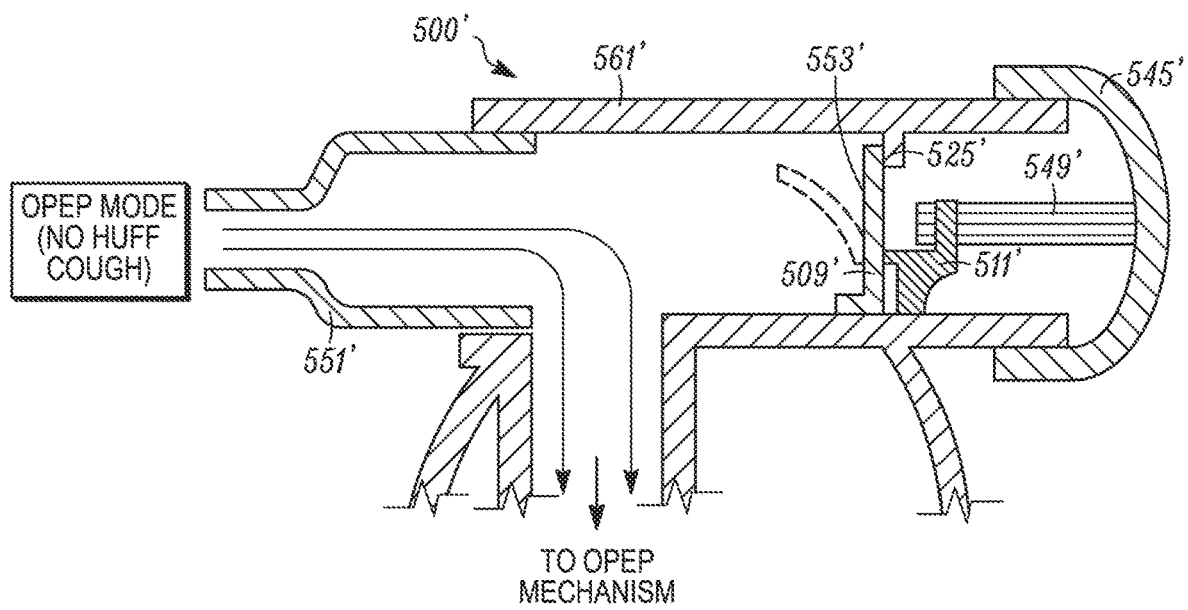
FIGS. 71B and 72B are partial cross-sectional views illustrating an exemplary combined OPEP and Huff Cough simulation device according to the embodiment of FIGS. 71A and 72A.
Figure 72A:
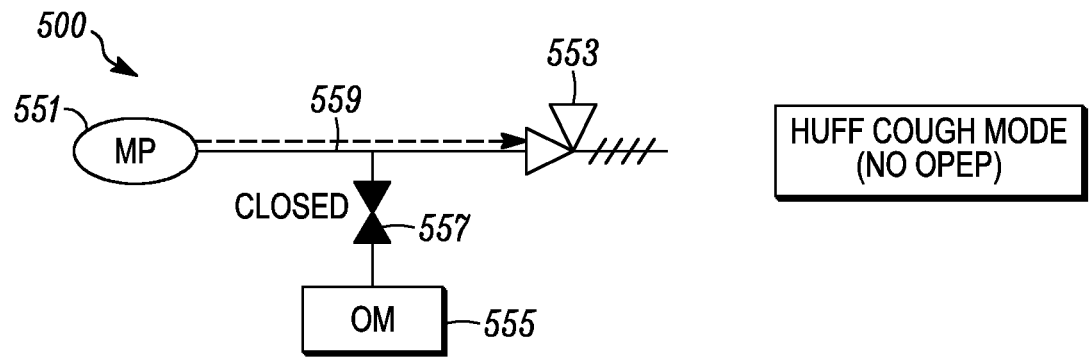
Figure 72B:
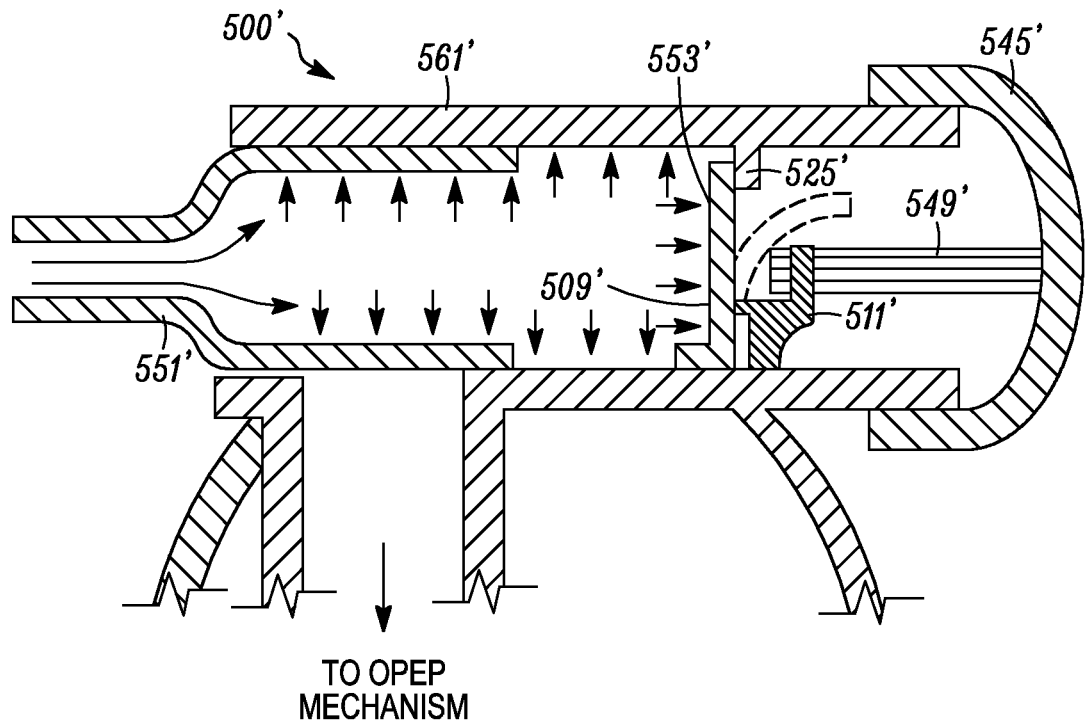

FIGS. 71A and 72A are schematics illustrating the primary components of a combined OPEP and Huff Cough simulation device 500. FIGS. 71B and 72B are partial cross-sectional views illustrating an exemplary combined OPEP and Huff Cough device 500' according to this embodiment. In this embodiment, the device 500 and 500' is configured to selectively provide OPEP therapy without any Huff Cough simulations (illustrated in FIGS. 71A and 71B), or Huff Cough simulation without OPEP therapy (illustrated in FIGS. 72A and 72B).

As shown in FIGS. 71A and 72A, a device 500 according to this embodiment generally includes a mouthpiece 551, a Huff Cough mechanism 553 or simulation device, an OPEP mechanism 555 or OPEP device, and a valve 557. The mouthpiece 551, the Huff Cough mechanism 553, the OPEP mechanism 555, and the valve 557 are interconnected via a conduit 559 in the configuration shown in FIGS. 71A and 72A. That is, the conduit 559 from the mouthpiece 551 branches into one segment leading to the valve 557, followed by the OPEP mechanism 555, while another segment leads to the Huff cough mechanism 553.

The OPEP mechanism 555 may comprise any suitable OPEP device, including any of the previously described or identified OPEP devices. Likewise, the Huff Cough mechanism 553 may comprise any suitable Huff Cough simulation device, including any of the previously described or identified Huff Cough simulation devices. The valve 557 may comprise any suitable means for selectively opening and closing the flow of air through the conduit segment leading to the OPEP mechanism, including for example, a gate valve, a ball valve, or a butterfly valve. The valve may be selectively opened and closed by the user, for example, via a thumb screw, a lever, a switch, or the like. Alternatively, the valve 557 may be achieved by selective movement of the mouthpiece 551, as shown and described below with regard to FIGS. 71B and 72B. A user may inhale air through the Huff Cough mechanism 553.

In FIG. 71A, the valve 557 is open, such that exhaled air is free to flow past the valve 557 into the OPEP mechanism 555 for the administration of OPEP therapy. In this configuration, air exhaled by a user into the mouthpiece 551 flows into the OPEP mechanism 555, rather than the Huff Cough mechanism 553, because the Huff Cough mechanism 553 is designed to remain closed, or prevent the flow of air therethrough, until a threshold pressure is met. Typically, the oscillating pressures generated by the OPEP mechanism 555 will remain below the threshold pressure of the Huff Cough mechanism 553, such that the flow of exhaled air through the Huff Cough mechanism 553 will be prevented.

In FIG. 72A, the valve 557 is closed, such that exhaled air is blocked from flowing past the valve 557 into the OPEP mechanism 555, forcing the exhaled air into the Huff Cough mechanism 553 for simulating a Huff Cough. In this configuration, as air is exhaled by a user into the mouthpiece 551, pressure increases within the conduit 559 and the Huff Cough mechanism 553, until a threshold pressure is reached, at which point a valve or blocking member within the Huff Cough mechanism 553 opens, thereby allowing the flow of air through the Huff Cough mechanism 553.

FIGS. 71B and 72B are partial cross-sectional views illustrating an exemplary combined OPEP and Huff Cough simulation device 500' according to the configuration of FIGS. 71A and 72A. The device includes an OPEP mechanism (not shown), a Huff Cough mechanism 553', a housing 561', and a mouthpiece 551'. The OPEP mechanism may function in the same manner as shown and described above with regard to the OPEP device 300. Similarly, the Huff Cough mechanism 553' functions in the same manner as shown and described above with regard to the Huff Cough device 400. Like the Huff Cough device 400, the Huff Cough mechanism 553' of device 500' includes a valve 509', a valve brace 511', a rim 525', a reset button 545', and a rod 549'. Unlike in the Huff Cough device 400, the reset button 545' of the Huff Cough mechanism 553' is shaped and sized to fit in sliding engagement within the housing 561', such that a user may selectively move the reset button 545' relative to the housing 551' to reset the valve 509' to a closed position. Like in the Huff Cough device 400, the reset button 545' may also be rotated relative to the housing 561' in order to selectively adjust a position of the valve brace 511' relative to the valve 509', thereby selectively increasing or decreasing the threshold exhalation pressure at which the Huff Cough mechanism 553' opens.

As previously noted the mouthpiece 551' may serve as the valve 557. That is the mouthpiece 551' may be shaped and sized to fit in sliding engagement within the housing 561', such that a user may selectively move the mouthpiece 551' between open and closed positions (e.g. by sliding into and out of the housing 561', as shown in FIGS. 71B and 72B, or by rotation of an opening in the mouthpiece 551' relative to the conduit segment leading to the OPEP mechanism). In FIG. 71B, the mouthpiece 551' is in an open position, such that exhaled air is free to flow from the mouthpiece 551' into the OPEP mechanism for the administration of OPEP therapy. In this configuration, air exhaled by a user into the mouthpiece 551' flows into the OPEP mechanism, rather than the Huff Cough mechanism 553', because the valve 509' of the Huff Cough mechanism 553' remains closed, preventing the flow of air therethrough. However, the valve 509' of the Huff Cough mechanism 553' may serve as an inhalation valve, permitting inhalation at the mouthpiece 551' through the Huff Cough mechanism 553'. In FIG. 72B, the mouthpiece 551' is in a closed position, such that exhaled air is blocked from flowing into the OPEP mechanism, forcing the exhaled air into the Huff Cough mechanism 553' for simulating a Huff Cough. In this configuration, as air is exhaled by a user into the mouthpiece 551', pressure increases within the housing 561' and the Huff Cough mechanism 553', until a threshold pressure is reached, at which point the valve 509' of the Huff Cough mechanism 553' blows open, thereby allowing the flow of air through the Huff Cough mechanism 553'. Upon completion of exhalation, the valve 509' may be reset to the closed position by pressing the reset button 545' and extending the rod 549', for performing subsequent Huff Cough simulations.

Combined OPEP and Huff Cough—Embodiment Two

Figure 73A:
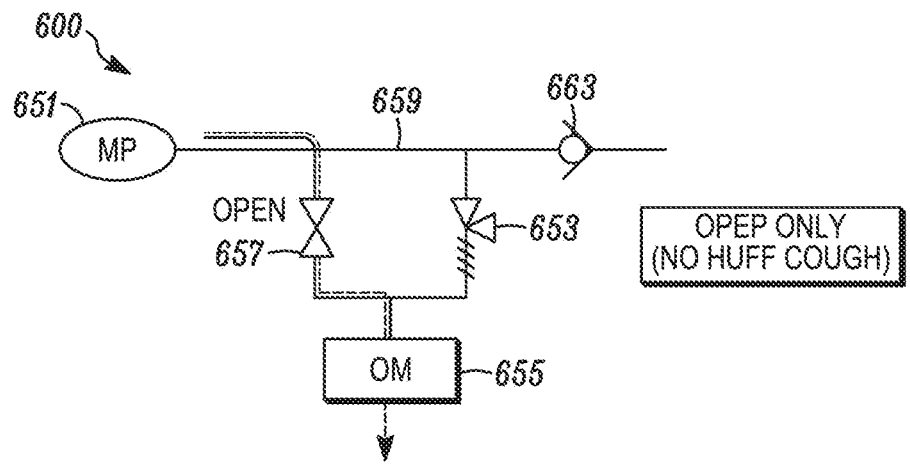
FIGS. 73A and 74A are schematics illustrating the primary components of a combined OPEP and Huff Cough simulation device according to another embodiment of the present disclosure.
Figure 73B:
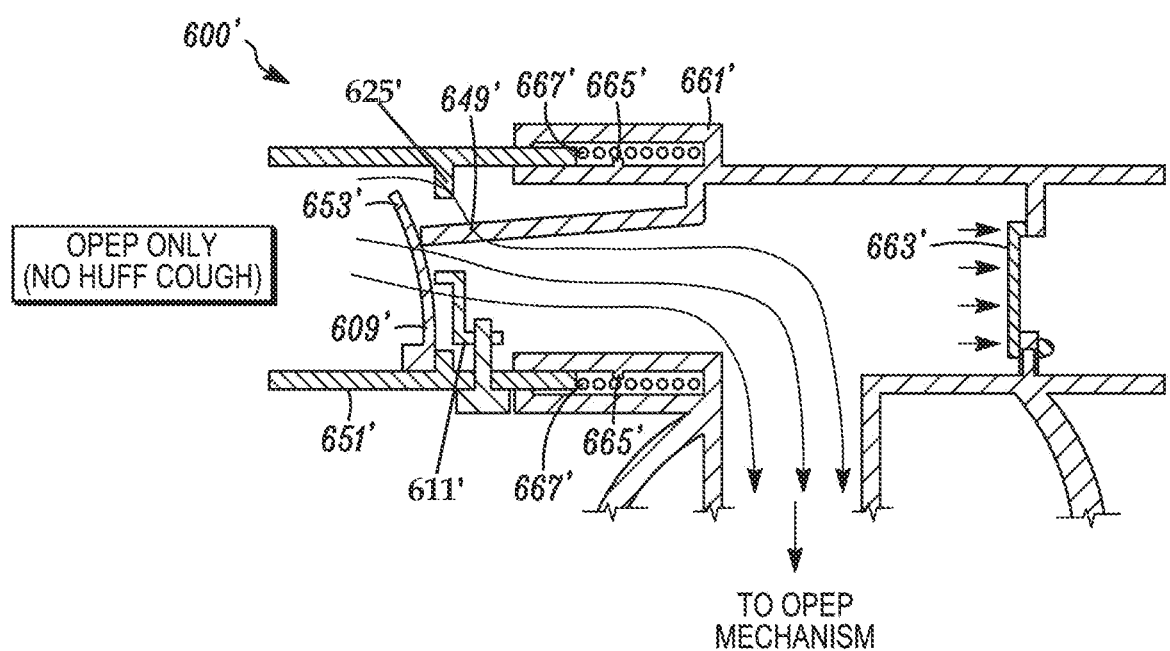
FIGS. 73B and 74B are partial cross-sectional views illustrating an exemplary combined OPEP and Huff Cough simulation device according to the embodiment of FIGS. 73A and 74A.
Figure 74A:
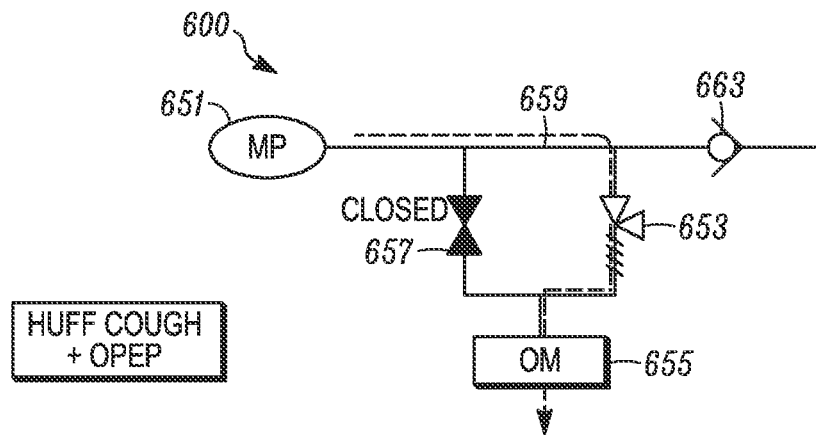
Figure 74B:
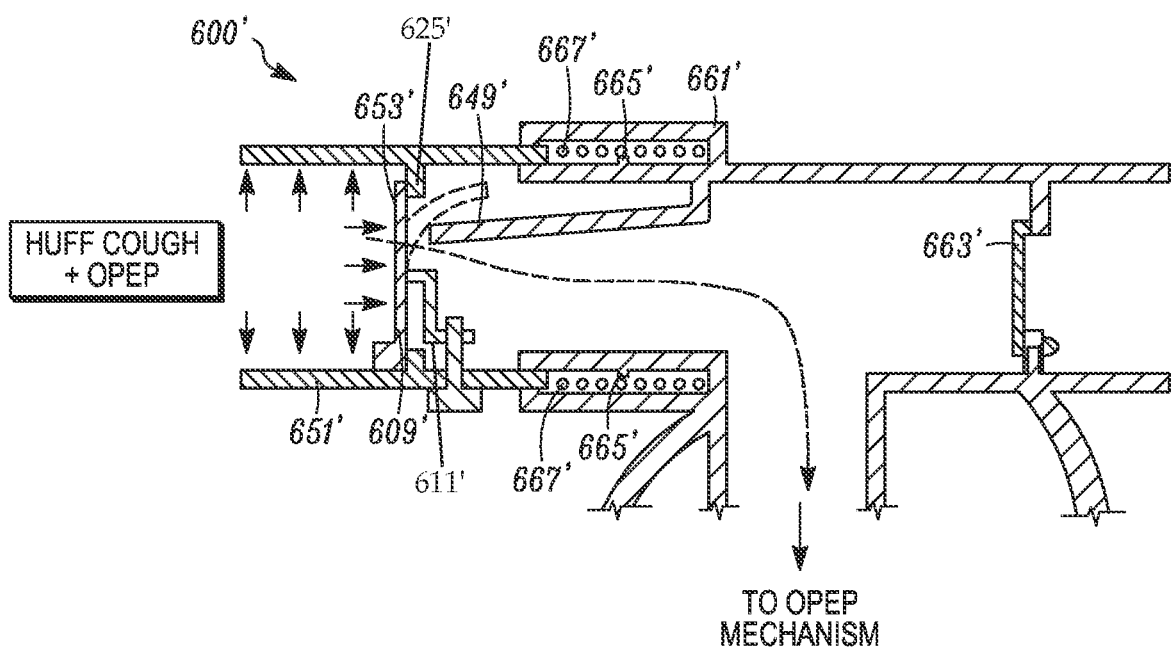

FIGS. 73A and 74A are schematics illustrating the primary components of a combined OPEP and Huff Cough simulation device 600. FIGS. 73B and 74B are partial cross-sectional views illustrating an exemplary combined OPEP and Huff Cough device 600' according to this embodiment. In this embodiment, the device 600 and 600' is configured to selectively provide OPEP therapy without any Huff Cough simulation (illustrated in FIGS. 73A and 73B), or a Huff Cough simulation followed by OPEP therapy (illustrated in FIGS. 74A and 74B).

As shown in FIGS. 73A and 74A, a device 600 according to this embodiment generally includes a mouthpiece 651, a Huff Cough mechanism 653 or simulation device, an OPEP mechanism 655 or OPEP device, a valve 657, and an inhalation valve 663. The mouthpiece 651, the Huff Cough mechanism 653, the OPEP mechanism 655, the valve 657, and the inhalation valve 663 are interconnected via a conduit 659 in the configuration shown in FIGS. 73A and 74A. That is, the conduit 659 leading from the mouthpiece 651 branches into a segment having the valve 657 in parallel with a segment having the Huff Cough mechanism 653. The parallel segments then reconnect and feed into the OPEP mechanism 655. The conduit leading from the mouthpiece 651 also leads to the inhalation valve 663.

The OPEP mechanism 655 may comprise any suitable OPEP device, including any of the previously described or identified OPEP devices. Likewise, the Huff Cough mechanism 653 may comprise any suitable Huff Cough simulation device, including any of the previously described or identified Huff Cough simulation devices. The valve 657 may comprise any suitable means for selectively opening and closing the flow of air through the conduit segment having the valve, including for example, a gate valve, a ball valve, or a butterfly valve. The valve 657 may be selectively opened and closed by the user, for example, via a thumb screw, a lever, a switch, or the like. A suitable inhalation vale 663, for example, is shown and described with reference to FIG. 52. Alternatively, the valve 657 may be achieved by selectively opening and closing the valve or blocking member of the Huff Cough mechanism, as shown an described below with regard to FIGS. 73B and 74B.

In FIG. 73A, the valve 657 is open, such that exhaled air is free to flow past the valve 657 into the OPEP mechanism 655 for the administration of OPEP therapy (without Huff Cough). In this configuration, the air exhaled by a user into the mouthpiece 651 flows into the OPEP mechanism 655, rather than the Huff Cough mechanism 653, because the Huff Cough mechanism 653 is designed to remain closed, or prevent the flow of air therethrough, until a threshold pressure is met. Typically, the oscillating pressures generated by the OPEP mechanism 655 will remain below the threshold pressure of the Huff Cough mechanism 653, such that the flow of exhaled air through the Huff Cough mechanism 653 will be prevented. Similarly, the inhalation valve 663 is configured to remain closed during a period of exhalation, opening only during a period of inhalation.

In FIG. 74A, the valve 657 is closed, such that exhaled air is blocked from flowing past the valve 657 into the OPEP mechanism 655, forcing the exhaled air into the Huff cough mechanism 653 for simulating a Huff Cough (without OPEP). Similarly, the inhalation valve 663 is configured to remain closed during a period of exhalation, opening only during a period of inhalation. In this configuration, as air is exhaled by a user into the mouthpiece 651, pressure increases within the conduit 659 and the Huff Cough mechanism 653, until a threshold pressure is reached, at which point a valve or blocking member within the Huff Cough mechanism 653 opens, thereby allowing the flow of air through the Huff Cough mechanism 653.

FIGS. 73B and 74B are partial cross-sectional views illustrating an exemplary combined OPEP and Huff Cough simulation device 600' according to the configuration of FIGS. 73A and 74A. The device 600' includes an OPEP mechanism (not shown), a Huff Cough mechanism 653', a housing 661', a mouthpiece 651', and an inhalation valve 663'. The OPEP mechanism may function in the same manner as shown and described above with regard to OPEP device 300. Similarly, the Huff Cough mechanism 653' functions in the same manner as shown and described above with regard to the Huff Cough device 400. Like the Huff Cough device 400, the Huff Cough mechanism 653' of device 600' includes a valve 609', a valve brace 611', and a rim 625'. Like in the Huff Cough device 400, a position of the valve brace 611' relative to the valve 609' may be adjusted to selectively increase or decrease the threshold exhalation pressure of the Huff Cough mechanism 653'.

Similar to the reset button 445 and the rod 449 of the Huff Cough device 400, the Huff Cough mechanism 653' includes a reset finger 649' extending from the housing 661' toward the valve 609'. The mouthpiece 651' may be shaped and sized to fit in sliding engagement within the housing 661' or a portion of the housing, such that a user may selectively move the mouthpiece 651' between a first position (shown in FIG. 73B), where the valve 609' is opened by the finger 649', and a second position (shown in FIG. 74B), where the finger 649' is retracted and the valve 609' is closed. The mouthpiece 651' may be biased toward the second position (shown in FIG. 74B), for example, by a spring 667'. In this way, after performing a Huff Cough simulation, when the valve 609' is in an open position, as illustrated by the dashed line in FIG. 74B, a user may selectively move the mouthpiece 651' relative to the housing 661' from the second position (shown in FIG. 74B) to the first position (shown in FIG. 73B), thereby moving the valve 609' to the position illustrated by the dashed line in FIG. 73B. As the mouthpiece 651' returns to the position shown in FIG. 74B under the biasing force of the spring 667', the valve 609' returns to a closed position (shown in FIG. 74B), for performing another Huff Cough simulation. Moreover, the inhalation valve 663' and the valve 609' of the Huff Cough mechanism 653' are configured to open upon inhalation at the mouthpiece.

As explained above, the valve 657 of the device 600 may be achieved by selectively opening and closing the valve 609' of the Huff Cough mechanism 653'. In this regard, the mouthpiece 651' and/or the housing 661' may also include a detent 665' configured to retain the mouthpiece 651' in the first position (shown in FIG. 73B) when the mouthpiece 651' is depressed beyond the detent 665', thereby also maintaining the valve 609' of the Huff Cough mechanism 653' in the open position shown in FIG. 73B. In this way, when the valve 609' of the Huff Cough mechanism 653' is maintained in the open position shown in FIG. 73B, exhaled air flows freely through the Huff Cough mechanism 653' and into the OPEP mechanism for the administration of OPEP therapy. When the valve 609' of the Huff Cough mechanism 653' is in the closed position shown in FIG. 74B, exhaled air is prevented from flowing through the Huff Cough mechanism 653' until a threshold pressure is reached, at which point the valve 609' opens, permitting the flow of air through the Huff Cough mechanism 653' and into the OPEP mechanism for the administration of OPEP therapy.

Combined OPEP and Huff Cough—Embodiment Three

Figure 75A:
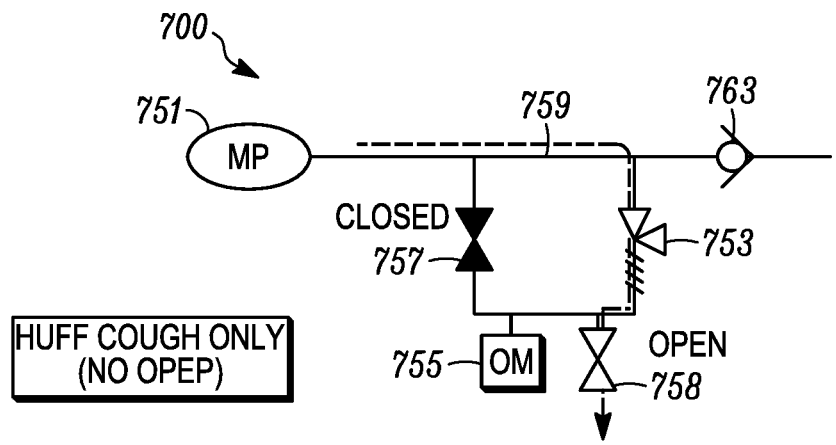
FIGS. 75A, 76A, and 77 are schematics illustrating the primary components of a combined OPEP and Huff Cough simulation device according to another embodiment of the present disclosure; and, FIGS. 75B and 76B are partial cross-sectional views illustrating modifications to the combined OPEP and Huff Cough simulation device of FIGS. 73B and 74B, showing selective opening and closing of an inhalation valve.
Figure 75B:
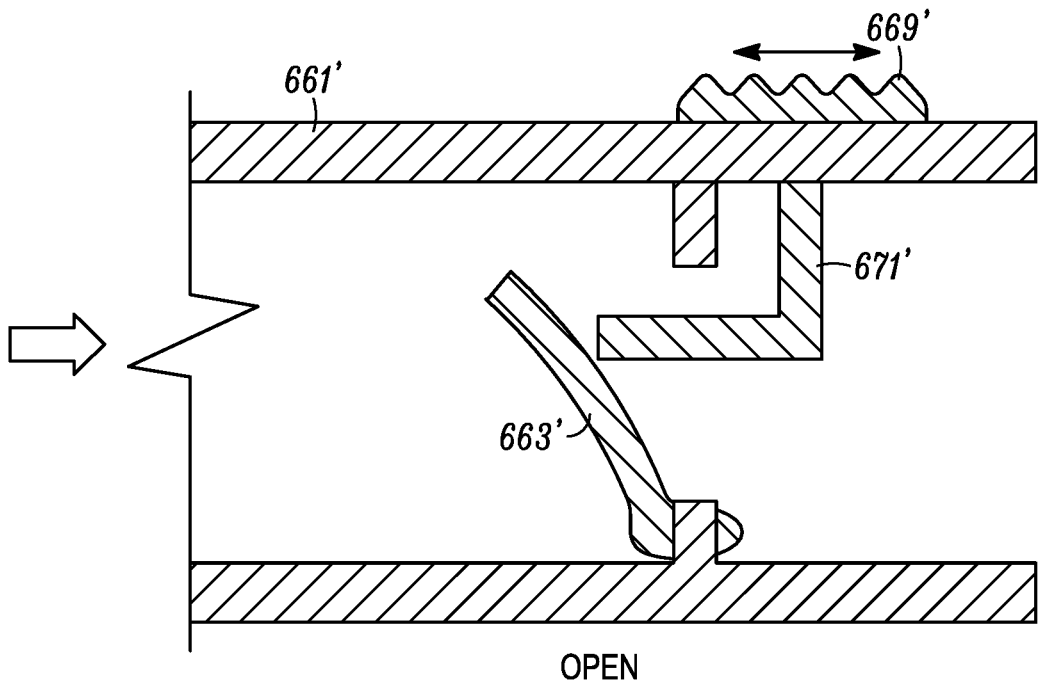
Figure 76A:
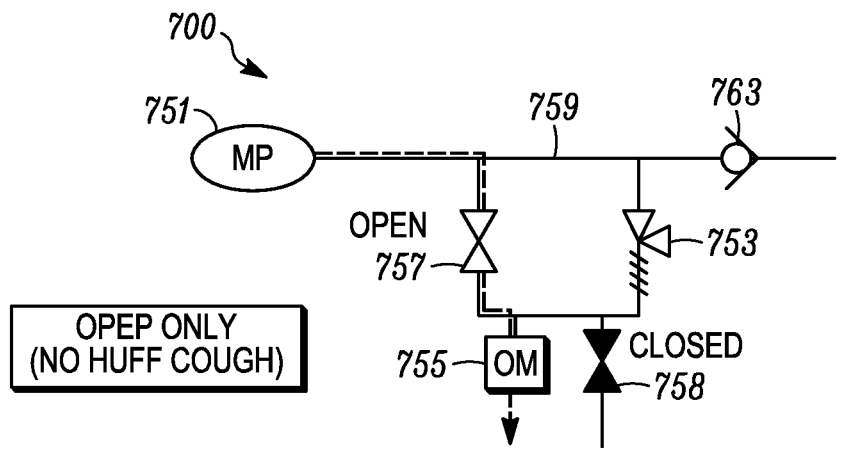
Figure 76B:
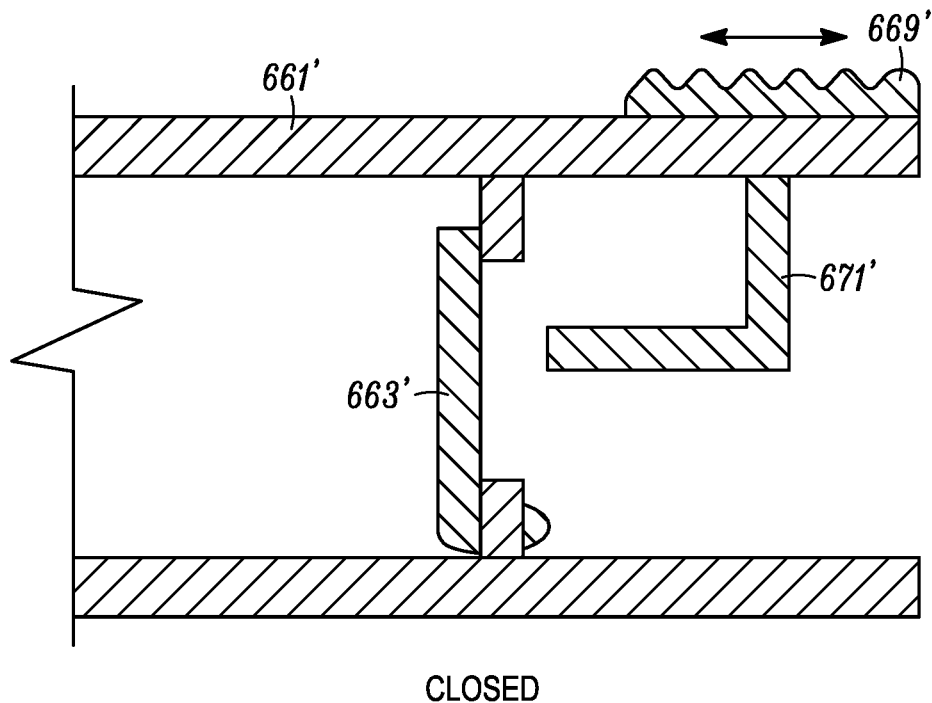
Figure 77:
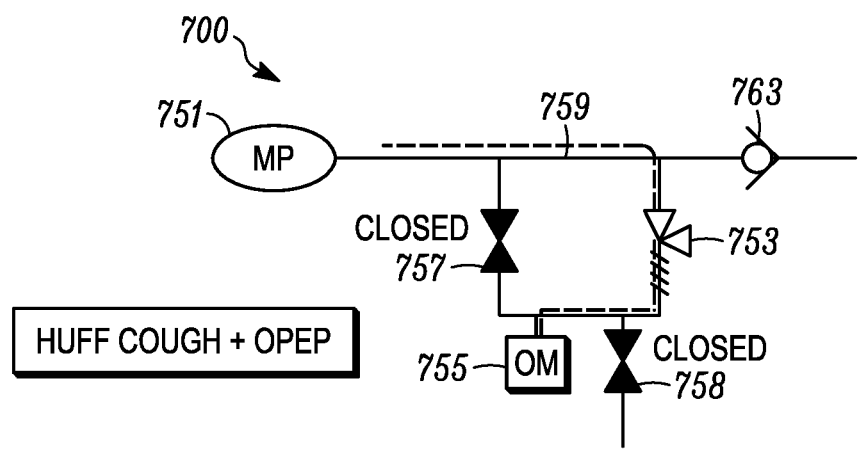

FIGS. 75A, 76A, and 77 are schematics illustrating the primary components of a combined OPEP and Huff Cough simulation device 700. FIGS. 75B and 76B are partial cross-sectional views illustrating modifications to the combined OPEP and Huff Cough simulation device 600' shown and described with reference to FIGS. 73B and 74B, showing selective opening and closing of the inhalation valve 663'. In this embodiment, the device 700 is configured to selectively provide Huff Cough simulations without OPEP therapy (illustrated in FIGS. 75A and 75B), OPEP therapy without any Huff Cough simulation (illustrated in FIGS. 76A and 76B), or a Huff Cough simulation followed by OPEP therapy (illustrated in FIGS. 77 and 76B).

As shown in FIGS. 75A, 76A, and 77, a device 700 according to this embodiment generally includes a mouthpiece 751, a Huff Cough mechanism 753 or simulation device, an OPEP mechanism 755 or OPEP device, a first valve 757, a second valve 758, and an inhalation valve 763. The mouthpiece 751, the Huff Cough mechanism 753, the OPEP mechanism 755, the first valve 757, the second valve 758, and the inhalation valve 763 are interconnected via a conduit 759 in the configuration shown in FIGS. 75A, 76A, and 77. That is the conduit 759 leading from the mouthpiece 751 branches into a segment having the first valve 757 in parallel with a segment having the Huff Cough mechanism 753. The parallel segments then reconnect and feed into either the OPEP mechanism 755 or the second valve 758, which are also arranged in parallel segments. The conduit 759 leading from the mouthpiece also leads to the inhalation valve 763.

As with the prior embodiment, the OPEP mechanism 755 may comprise any suitable OPEP device, including any of the previously described or identified OPEP devices. Likewise, the Huff Cough mechanism 753 may comprise any suitable Huff Cough simulation device, including any of the previously described or identified Huff Cough simulation devices. The first valve 757 and the second valve 758 may comprise any suitable means for selectively opening and closing the flow of air through the conduit segments having the valves 757 and 758, including for example, a gate valve, a ball valve, or a butterfly valve. The valves 757 and 758 may be selectively opened and closed by the user, for example, via a thumb screw, a lever, a switch, or the like. A suitable inhalation vale 763, for example, is shown and described with reference to FIG. 52. Alternatively, the first valve 757 may be achieved by selectively opening and closing the valve or blocking member of the Huff Cough mechanism 753, as shown and described above with regard to FIGS. 73B and 74B. The second valve 758 may alternatively be achieved by selectively opening and closing the inhalation valve 763, as shown and described below with regard to FIGS. 75B and 76B.

In FIG. 75A, the first valve 757 is closed, such that exhaled air is blocked from flowing past the first valve 757 into the OPEP mechanism 755, forcing the exhaled air into the Huff Cough mechanism 753 for simulating a Huff Cough (without OPEP). Similarly, the inhalation valve 763 is configured to remain closed during a period of exhalation, opening only during a period of inhalation. In this configuration, as air is exhaled by a user into the mouthpiece 751, pressure increases within the conduit 759 and the Huff Cough mechanism 753, until a threshold pressure is reached, at which point a valve or blocking member within the Huff Cough mechanism 753 opens, thereby allowing the flow of air through the Huff Cough mechanism 753. In FIG. 75A, the second valve 758 is open, such that air flowing through the Huff Cough mechanism 753 is free to flow past the second valve 758 and exit the device 700, rather than into the OPEP mechanism 755.

In FIG. 76A, the first valve 757 is open while the second valve 758 is closed, such that exhaled air is free to flow past the first valve 757 into the OPEP mechanism 755 for the administration of OPEP therapy (without Huff Cough). In this configuration, air exhaled by a user into the mouthpiece 751 flows into the OPEP mechanism 755, rather than through the Huff Cough mechanism 753, because the Huff Cough mechanism 753 is designed to remain closed, or prevent the flow of air therethrough, until a threshold pressure is met. Typically, the oscillating pressures generated by the OPEP mechanism 755 will remain below the threshold pressure of the Huff Cough mechanism 753, such that the flow of exhaled air through the Huff Cough mechanism will be prevented. Similarly, the inhalation valve 763 is configured to remain closed during a period of exhalation, opening only during a period of inhalation.

In FIG. 77, the first valve 757 is closed, such that exhaled air is blocked from flowing past the first valve 757 into the OPEP mechanism 755, forcing the exhaled air into the Huff Cough mechanism 755 for simulating a Huff Cough. Similarly, the inhalation valve 763 is configured to remain closed during a period of exhalation, opening only during a period of inhalation. In this configuration, as air is exhaled by a user into the mouthpiece 751, pressure increases within the conduit 759 and the Huff Cough mechanism 753, until a threshold pressure is reached, at which point a valve or blocking member within the Huff Cough mechanism 753 opens, thereby allowing the flow of air through the Huff Cough mechanism 753. In FIG. 77, the second valve 758 is closed, such that air flowing through the Huff Cough mechanism 753 is blocked from flowing past the second valve 758, instead flowing into the OPEP mechanism 755 for administration of OPEP therapy.

FIGS. 75B and 76B are partial cross-sectional views illustrating modifications to the combined OPEP and Huff Cough simulation device 600' shown and described with reference to FIGS. 73B and 74B. That is, an exemplary device according to the configuration of FIGS. 75A, 76A, and 77 may include the combined OPEP and Huff Cough simulation device 600', modified as described below with reference to FIGS. 75B and 76B.

Specifically, as noted above, the second valve 758 may be achieved by selectively opening and closing the inhalation valve 763. As shown in FIGS. 75B and 76B, a switch 669' located on the outside of the housing 661' may be positioned relative to the inhalation valve 663' such that a finger 671' extending from the switch 669' toward the inhalation valve 663' may be selectively moved between a first position (shown in FIG. 75B), where the finger 671' holds the inhalation valve 663' in an open position, and a second position (shown in FIG. 76B), where the finger 671' is retracted from the inhalation valve 663', allowing the inhalation valve 663' to remain closed, opening only during a period of inhalation.

In this regard, the device 600' may be used to simulate a Huff Cough (without OPEP therapy) by selectively positioning the mouthpiece 651' in the second position (illustrated in FIG. 74B), while the switch 669' is positioned in the first position (illustrated in FIG. 75B). Likewise, the device 600' may be used to administer OPEP therapy (without Huff Cough) by selectively positioning the mouthpiece 651' in the first position (illustrated in FIG. 73B), while the switch 669' is positioned in the second position (illustrated in FIG. 76B). Finally, the device 600' may be used to simulate a Huff Cough followed by administration of OPEP therapy, by selectively positioning the mouthpiece 651' in the second position (illustrated in FIG. 74B), while the switch 669' is positioned in the second position (illustrated in FIG. 76B).

The invention claimed is:

1. A respiratory treatment device comprising:
   an oscillating positive expiratory pressure ("OPEP") valve moveable repeatedly in response to air flow through the OPEP valve between a closed position where air flow through the OPEP valve is restricted, and an open position where air flow through the OPEP valve is less restricted;
   a Huff Cough valve moveable in response to a threshold exhalation pressure from a closed position where air flow through the Huff Cough valve is restricted, to an open position where air flow through the Huff Cough valve is less restricted;
   a user interface; and,
   a conduit leading from the user interface to the OPEP valve and the Huff Cough valve.

2. The respiratory treatment device of claim 1, wherein air flow through the conduit is selectively directed to the OPEP valve and the Huff Cough valve.

3. The respiratory treatment device of claim 1, wherein air flow through the conduit is selectively directed to the OPEP valve, the Huff Cough valve, or both the OPEP valve and the Huff Cough valve.

4. The respiratory treatment device of claim 1, wherein airflow through the conduit passes through the Huff Cough valve, followed by the OPEP valve.

5. The respiratory treatment device of claim 1, further comprising a flow valve positioned in the conduit to selectively direct air flow to at least one of the OPEP valve and the Huff Cough valve.

6. The respiratory treatment device of claim 5, wherein the flow valve is positioned along a first segment of the conduit and the Huff Cough valve is positioned along a second segment of the conduit, where airflow along the first segment does not traverse the second segment, and airflow along the second segment does not traverse the first segment.

7. The respiratory treatment device of claim 6, wherein the OPEP valve is positioned along a third segment of the conduit where the first segment and the second segment are joined.

8. The respiratory treatment device of claim 7, wherein the flow valve is selectively moveable between an open position where air flow along the first segment is permitted, and a closed position where airflow along the first segment is not permitted.

9. The respiratory treatment device of claim 8, wherein the flow valve is selectively moveable between the open position to provide OPEP therapy, and the closed position to provide a Huff Cough simulation followed by OPEP therapy.

10. The respiratory treatment device of claim 6, wherein the OPEP valve is positioned along a third segment of the conduit where the first segment and the second segment are joined, and a second flow valve is positioned along a fourth segment of the conduit where the first segment and the second segment are joined, where airflow along the third segment does not traverse the fourth segment, and airflow along the fourth segment does not traverse the third segment.

11. The respiratory treatment device of claim 10, wherein the flow valve is selectively moveable between an open position where air flow along the first segment is permitted, and a closed position where airflow along the first segment is not permitted, and wherein the second flow valve is selectively moveable between an open position where air flow along the fourth segment is permitted, and a closed position where airflow along the fourth segment is not permitted.

12. The respiratory treatment device of claim 11, wherein the device is configured to provide a Huff Cough simulation without OPEP therapy when the flow valve is in the closed position and the second flow valve is in the open position.

13. The respiratory treatment device of claim 11, wherein the device is configured to provide OPEP therapy without any Huff Cough simulation when the flow valve is in the open position and the second flow valve is in the closed position.

14. The respiratory treatment device of claim 11, wherein the device is configured to provide a Huff Cough simulation followed by OPEP therapy when the flow valve is in the closed position and the second flow valve is in the closed position.

15. The respiratory treatment device of claim 1, wherein the OPEP valve is positioned along a first segment of the conduit and the Huff Cough valve is positioned along a second segment of the conduit, where air flow through the first segment does not traverse the second segment, and air flow through the second segment does not traverse the first segment.

16. The respiratory treatment device of claim 15, further comprising a flow valve positioned in the first segment, wherein the flow valve is selectively moveable between an open position where air flow through the first segment to the OPEP valve is permitted, and a closed position where air flow through the first segment to the OPEP valve is not permitted.

17. The respiratory treatment device of claim 16, wherein the flow valve is selectively moveable between the open position to provide OPEP therapy, and the closed position to provide a Huff Cough simulation.

18. The respiratory treatment device of claim 1, wherein the Huff Cough valve is configured to open in response to inhalation at the user interface.

19. The respiratory treatment device of claim 1, wherein the user interface is moveable relative to the conduit between a first position, where the flow of air through the conduit to the OPEP valve is permitted, and a second position where the flow of air to the OPEP valve is not permitted.

20. The respiratory treatment device of claim 1, wherein the Huff Cough valve and a finger within the device are selectively moveable relative to one another to open the Huff Cough valve.

21. The respiratory treatment device of claim 1, further comprising an inhalation valve positioned along the conduit.

22. The respiratory treatment device of claim 21, wherein airflow between the inhalation valve and the user interface does not pass through the OPEP valve or the Huff Cough valve.

23. The respiratory treatment device of claim 21, further comprising a switch moveable relative to the inhalation valve between a first position where the switch engages and maintains the inhalation valve in an open position, and a second position where the switch is not engaged with the inhalation valve.

24. A respiratory treatment device comprising:
a user interface;
a Hugh Cough valve moveable in response to a threshold exhalation pressure from a closed position where air flow through the Huff Cough valve is restricted, to an open position where air flow through the Huff Cough valve is less restricted;
an oscillating positive expiratory pressure ("OPEP") valve moveable repeatedly in response to air flow through the OPEP valve between a closed position where air flow through the OPEP valve is restricted, and an open position where air flow through the OPEP valve is less restricted;
a conduit leading from the user interface to the Huff Cough valve, and from the Huff Cough valve to OPEP valve, wherein airflow through the conduit passes through the Huff Cough valve, followed by the OPEP valve; and,
an inhalation valve positioned along the conduit, wherein airflow between the inhalation valve and the user interface does not pass through the Huff Cough valve or the OPEP valve.

25. A respiratory treatment device comprising:
a user interface;
a Hugh Cough valve moveable in response to a threshold exhalation pressure from a closed position where air flow through the Huff Cough valve is restricted, to an open position where air flow through the Huff Cough valve is less restricted;
an oscillating positive expiratory pressure ("OPEP") valve moveable repeatedly in response to air flow through the OPEP valve between a closed position where air flow through the OPEP valve is restricted, and an open position where air flow through the OPEP valve is less restricted; and,
a conduit leading from the user interface to the Huff Cough valve and the OPEP valve, wherein at least one flow valve positioned in the conduit selectively directs airflow through the conduit to the Huff Cough valve, the OPEP valve, or both the Huff Cough valve and the OPEP valve.

* * * * *